(12) United States Patent
Tao et al.

(10) Patent No.: US 11,480,541 B2
(45) Date of Patent: Oct. 25, 2022

(54) OPTICAL IMAGING OF SINGLE MOLECULE SIZE, CHARGE, MOBILITY, BINDING AND CONFORMATIONAL CHANGE

(71) Applicant: Arizona Board of Regents on behalf of Arizona State University, Scottsdale, AZ (US)

(72) Inventors: Nongjian Tao, Fountain Hills, AZ (US); Guanzhong Ma, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 501 days.

(21) Appl. No.: 16/584,120

(22) Filed: Sep. 26, 2019

(65) Prior Publication Data

US 2020/0096472 A1    Mar. 26, 2020

Related U.S. Application Data

(60) Provisional application No. 62/736,988, filed on Sep. 26, 2018.

(51) Int. Cl.
*G01N 27/327* (2006.01)
*G01N 21/47* (2006.01)
(Continued)

(52) U.S. Cl.
CPC ......... *G01N 27/3275* (2013.01); *C03C 17/36* (2013.01); *G01N 15/1475* (2013.01);
(Continued)

(58) Field of Classification Search
CPC ........... G01N 27/3275; G01N 15/1475; G01N 21/47; C03C 17/36; G06T 7/0012
See application file for complete search history.

(56) References Cited

U.S. PATENT DOCUMENTS 7,132,837 B1    11/2006  Tao
8,416,417 B2    4/2013   Foley et al.
(Continued)

FOREIGN PATENT DOCUMENTS

WO    2008021614 A2    2/2008
WO    2008148025 A1    12/2008
(Continued)

OTHER PUBLICATIONS

Armstrong, J. et al., "The Hydrodynamic Radii of Macromolecules and Their Effect on Red Blood Cell Aggregation", Biophysical Journal, Dec. 2004, vol. 87, No. 6, pp. 4259-4270 <DOI:10.1529/biophysj.104.047746>.
(Continued)

*Primary Examiner* — Edward Park
(74) *Attorney, Agent, or Firm* — Withrow & Terranova, P.L.L.C; Vincent K. Gustafson

(57) ABSTRACT

A method for optical imaging of single protein molecules including tethering single protein molecules via a flexible polymer linker to a glass slide having a surface coated with an indium tin oxide (ITO) so that the single protein molecules are tethered to the coated surface. The single protein molecules are driven into oscillation by applying an alternating electric field to the coated surface and the glass slide is located in the field of view of an objective lens. Incident light is directed onto the coated surface from an angle to generate an evanescent field and produce scattered light. The scattered light is collected and imaged by a CMOS imager to record a sequence of images of the scattered light. A Fast Fourier Transform (FFT) filter is applied to each pixel of the recorded image sequence to produce an oscillation amplitude image from which size, charge, and mobility of the plurality of single protein molecules can be determined.

21 Claims, 38 Drawing Sheets

(51) Int. Cl.
| | |
|---|---|
| *G06T 7/00* | (2017.01) |
| *C03C 17/36* | (2006.01) |
| *G01N 33/487* | (2006.01) |
| *G01N 33/68* | (2006.01) |
| *G01N 33/543* | (2006.01) |
| *G01N 15/14* | (2006.01) |
| *G01N 21/17* | (2006.01) |

(52) U.S. Cl.
CPC ....... *G01N 21/47* (2013.01); *G01N 33/48721* (2013.01); *G01N 33/54353* (2013.01); *G01N 33/6854* (2013.01); *G06T 7/0012* (2013.01); *C03C 2217/948* (2013.01); *G01N 2015/1493* (2013.01); *G01N 2021/1765* (2013.01); *G06T 2207/20056* (2013.01)

(56) References Cited

U.S. PATENT DOCUMENTS

| | | | |
|---|---|---|---|
| 8,465,634 | B2 | 6/2013 | Tao et al. |
| 8,545,683 | B2 | 10/2013 | Tao et al. |
| 8,668,874 | B2 | 3/2014 | Tao et al. |
| 8,926,822 | B2 | 1/2015 | Tao et al. |
| 9,581,561 | B2 | 2/2017 | Tao et al. |
| 9,772,305 | B2 | 9/2017 | Tao |
| 9,909,993 | B2 | 3/2018 | Tao et al. |
| 10,222,372 | B2 | 3/2019 | Tao et al. |
| 10,401,298 | B2 | 9/2019 | Tao et al. |
| 10,408,757 | B2 | 9/2019 | Tao et al. |
| 10,413,226 | B2 | 9/2019 | Tao et al. |
| 10,539,530 | B2 | 1/2020 | Tao |
| 2003/0036067 | A1* | 2/2003 | Schwartz ......... G01N 27/44773 435/6.12 |
| 2007/0235348 | A1 | 10/2007 | Nagahara et al. |
| 2012/0270330 | A1 | 10/2012 | Tao et al. |
| 2016/0123924 | A1* | 5/2016 | Mason ............. G01N 27/44747 204/461 |
| 2017/0038380 | A1 | 2/2017 | Tao et al. |
| 2019/0082972 | A1 | 3/2019 | Tao et al. |
| 2019/0094146 | A1 | 3/2019 | Tao et al. |
| 2019/0170748 | A1 | 6/2019 | Tao et al. |
| 2019/0239761 | A1 | 8/2019 | Tao et al. |
| 2020/0000370 | A1 | 1/2020 | Tao et al. |
| 2020/0022628 | A1 | 1/2020 | Tao et al. |
| 2020/0156074 | A1 | 5/2020 | Tao et al. |
| 2020/0172951 | A1 | 6/2020 | Tao et al. |

FOREIGN PATENT DOCUMENTS

| | | |
|---|---|---|
| WO | 2009132262 A1 | 10/2009 |
| WO | 2010030874 A1 | 3/2010 |
| WO | 2010141610 A1 | 12/2010 |
| WO | 2011031500 A2 | 3/2011 |
| WO | 2015103459 A1 | 7/2015 |
| WO | 2017156084 A2 | 9/2017 |
| WO | 2018057753 A1 | 3/2018 |
| WO | 2018170009 A1 | 9/2018 |
| WO | 2018187548 A2 | 10/2018 |
| WO | 2018213790 A2 | 11/2018 |
| WO | 2018213790 A8 | 11/2018 |
| WO | 2019023320 A1 | 1/2019 |
| WO | 2019050847 A1 | 3/2019 |

OTHER PUBLICATIONS

Berger, C. et al., "Surface plasmon propagation near an index step", Optics Communications, Aug. 1999, vol. 167, No. 1-6, pp. 183-189 <DOI:10.1016/S0030-4018(99)00309-0>.

Bermudez, O. et al., "Aggregation and denaturation of antibodies: a capillary electrophoresis, dynamic light scattering, and aqueous two-phase partitioning study", Journal of Chromatography B, Jul. 2004 (available online Feb. 2004), vol. 807, No. 1, pp. 17-24 <DOI:10.1016/j.jchromb.2004.01.029>.

Beuwer, M. et al., "Stochastic Protein Interactions Monitored by Hundreds of Single-Molecule Plasmonic Biosensors", Nano Letters, May 2015 (available online Apr. 2015), vol. 15, No. 5, pp. 3507-3511 <DOI:10.1021/acs.nanolett.5b00872>.

Bjerneld, E. et al., "Single-Molecule Surface-Enhanced Raman and Fluorescence Correlation Spectroscopy of Horseradish Peroxidase", Journal of Physical Chemistry B, Feb. 2002 (available online Jan. 2002), vol. 106, No. 6, pp. 1213-1218 <DOI:10.1021/jp012268y>.

Borrebaeck, C., "Precision diagnostics: moving towards protein biomarker signatures of clinical utility in cancer", Nature Reviews Cancer, Mar. 2017 (available online Feb. 2017), vol. 17, pp. 199-204 <DOI:10.1038/nrc.2016.153>.

Brouhard, G. et al., "Microtubule dynamics: an interplay of biochemistry and mechanics", Nature Reviews Molecular Cell Biology, Jul. 2018 (available online Apr. 2018), vol. 19, pp. 451-463 <DOI:10.1038/s41580-018-0009-y>.

Cairns, R. et al., "Regulation of cancer cell metabolism", Nature Reviews Cancer, Feb. 2011 (available online Jan. 2011), vol. 11, pp. 85-95 <DOI:10.1038/nrc2981>.

Cao, S-H. et al., "Surface Plasmon-Coupled Emission: What Can Directional Fluorescence Bring to the Analytical Sciences?", Annual Review of Analytical Chemistry, Jul. 2012 (available online Apr. 2012), vol. 5, pp. 317-336 <DOI:10.1146/annurev-anchem-062011-143208>.

Cao, Y. et al., "A functional single-molecule binding assay via force spectroscopy", Proceedings of the National Academy of Sciences, Oct. 2007 (available online Sep. 2007), vol. 104, No. 40, pp. 15677-15681 <DOI:10.1073/pnas.0705367104>.

Chang, L. et al., "Identification of protein biomarkers and signaling pathways associated with prostate cancer radioresistance using label-free LC-MS/MS proteomic approach", Scientific Reports, Feb. 2017, vol. 7, No. 41834, 15 pages <DOI:10.1038/srep41834>.

Clery, A. et al., "switchSENSE: A new technology to study protein-RNA interactions", Methods, Apr. 2017 (available online Mar. 2017), vol. 118-119, pp. 137-145 <DOI:10.1016/j.ymeth.2017.03.004>.

Cole, D. et al., "Label-Free Single-Molecule Imaging with Numerical-Aperture-Shaped Interferometric Scattering Microscopy", ACS Photonics, Feb. 2017 (available online Jan. 2017), vol. 4, No. 2, pp. 211-216 <DOI: 10.1021/acsphotonics.6b00912>.

Cournia, Z. et al., "Membrane Protein Structure, Function, and Dynamics: a Perspective from Experiments and Theory", The Journal of Membrance Biology, Aug. 2015 (available online Jun. 2015), vol. 268, pp. 611-640 <Doi:10.1007/s00232-015-9802-0>.

Cugia, F. et al., "Interplay of ion specificity, pH and buffers: insights from electrophoretic mobility and pH measurements of lysozyme solutions", RCS Advances, Feb. 2013, vol. 3, pp. 5882-5888 <DOI:10.1039/C3RA00063J>.

Fang, Y. et al., "Real-Time Monitoring of Phosphorylation Kinetics with Self-Assembled Nano-oscillators", Angewandte Chemie International Edition, Feb. 2015 (available online Jan. 2015), vol. 54, No. 8, pp. 2539-2542 <DOI:10.1002/anie.201411040>.

Gaiduk, A. et al., "Room-Temperature Detection of a Single Molecule's Absorption by Photothermal Contrast", Science, Oct. 2010, vol. 330, No. 6002, pp. 353-356 <DOI:10.1126/science.1195475>.

Grigsby, J. et al., "Diffusivities of Lysozyme in Aqueous MgCl2 Solutions from Dynamic Light-Scattering Data: Effect of Protein and Salt Concentrations", The Journal of Physical Chemsitry B, Apr. 2000 (available online Mar. 2000), vol. 104, No. 15, pp. 3645-3650 <DOI:10.1021/jp993177s>.

Habuchi, S. et al., "Single-Molecule Surface Enhanced Resonance Raman Spectroscopy of the Enhanced Green Fluorescent Protein", Journal of the American Chemical Society, Jul. 2003 (available online Jun. 2003), vol. 125, No. 28, pp. 8446-8447 <DOI:10.1021/ja0353311>.

Hall, P. et al., "A Conformation- and Ion-Sensitive Plasmonic Biosensor", Nano Letters, Mar. 2011 (available online Jan. 2011), vol. 11, No. 3, pp. 1098-1105 <DOI:10.1021/nl103994w>.

Harder, P. et al., "Molecular Conformation in Oligo(ethylene glycol)-Terminated Self-Assembled Monolayers on Gold and Silver Surfaces Determines Their Ability to Resist Protein Adsorption", The Journal of Physical Chemistry B, Jan. 1998, vol. 102, No. 2, pp. 426-436 <DOI:10.1021/jp972635z>.

(56) References Cited

OTHER PUBLICATIONS

Hathout, Y. et al., "Large-scale serum protein biomarker discovery in Duchenne muscular dystrophy", Proceedings of the National Academy of Sciences, Jun. 2015 (available online May 2015, vol. 112, No. 23, pp. 7153-7158 <DOI:10.1073/pnas.1507719112>.

Hoeflich, K. et al., "Calmodulin in Action: Diversity in Target Recognition and Activation Mechanisms", Cell, Mar. 2002, vol. 108, No. 6, pp. 739-742 <DOI:10.1016/S0092-8674(02)00682-7>.

Hu, Y. et al., "Study of fibrinogen adsorption on poly (ethylene glycol)-modified surfaces using a quartz crystal microbalance with dissipation and a dual polarization interferometry", RSC Advances, Jan. 2014, vol. 4, pp. 7716-7724 <DOI:10.1039/C3RA46934D>.

Hughes, A. et al., "Single-cell western blotting", Nature Methods, Jul. 2014 (available online Jun. 2014), vol. 11, pp. 749-755 <DOI:10.1038/nmeth.2992>.

Jachimska, B. et al., "Characterization of Globular Protein Solutions by Dynamic Light Scattering, Electrophoretic Mobility, and Viscosity Measurements", Langmuir, Jul. 2008 (available online May 2008), vol. 24, No. 13, pp. 3866-6872 <DOI:10.1021/la800548p>.

Kim, K. et al., "Pairwise detection of site-specific receptor phosphorylations using single-molecule blotting", Nature Communications, Mar. 2016, vol. 7, No. 11107, 10 pages <DOI10.1038/ncomms11107>.

Knezevic, J. et al., "Quantitation of Affinity, Avidity, and Binding Kinetics of Protein Analytes with a Dynamically Switchable Biosurface", Journal of the American Chemical Society, Sep. 2012, vol. 134, No. 37, pp. 15225-15228 <DOI: 10.1021/ja3061276>.

Lakowicz, J., "Radiative decay engineering 3. Surface plasmon-coupled directional emission", Analytical Biochemistry, Jan. 2004 (available online Nov. 2003), vol. 324, No. 2, pp. 153-169 <DOI:10.1016/j.ab.2003.09.039>.

Langer, A. et al., "Polymerase/DNA interactions and enzymatic activity: multi¬parameter analysis with electro-switchable biosurfaces", Scientific Reports, Jul. 2015, vol. 5, No. 12066, 15 pages <DOI: 10.1038/srep12066>.

Langer, A. et al., "Protein analysis by time-resolved measurements with an electro-switchable DNA chip", Nature Communications, Jul. 2013, vol. 4, No. 2099, 8 pages <DOI:10.1038/ncomms3099>.

Lee, H-W. et al., "Real-time single-molecule co-immunoprecipitation analyses reveal cancer-specific Ras signalling dynamics", Nature Communications, Feb. 2013, vol. 4, No. 1505, 9 pages <DOI:10.1038/ncomms2507>.

Leskova, T. et al., "Surface plasmon polariton propagation near an index step", Optics Communications, May 2005 (available online Jan. 2005), vol. 249, No. 1-3, pp. 23-35 <DOI:10.1016/j.optcom.2005.01.014>.

Li, Y. et al., "Spectroscopic and dynamic light scattering studies of the interaction between pterodontic acid and bovine serum albumin", Acta Pharmaceutica Sinica B, Feb. 2012 (available online Jan. 2012), vol. 2, No. 1, pp. 53-59 <DOI:10.1016/j.apsb.2011.12.001>.

Liebel, M. et al., "Ultrasensitive Label-Free Nanosensing and High-Speed Tracking of Single Proteins", Nano Letters, Feb. 2017 (available online Jan. 2017), vol. 17, No. 2, pp. 1277-1281 <DOI:10.1021/acs.nanolett.6b05040>.

Loeb, A. et al., "The Electrical Double Layer Around a Spherical Colloid Particle", The Electrochemical Society, 1961, vol. 108, No. 12, pp. 269C.

Ma, G. et al., "Measuring Ligand Binding Kinetics to Membrane Proteins Using Virion Nano-oscillators", Journal of the American Chemical Society, Sep. 2018 (available online Aug. 2018), vol. 140, No. 36, pp. 11495-11501 <DOI:10.1021/jacs.8b07461>.

Ma, G. et al., "Optical imaging of single protein size, charge, mobility, binding and conformational change", bioRxiv, Dec. 2018, Version 1, 19 pages <DOI:10.1101/505404>.

Ma, G. et al., "Optical imaging of single protein size, charge, mobility, binding and conformational change", bioRxiv, Mar. 2019, Version 2, 19 pages <DOI:10.1101/505404>.

Majava, V. et al., "Domain Swapping and Different Oligomeric States for the Complex Between Calmodulin and the CalmodulinBinding Domain of Calcineurin A", PLoS ONE, Apr. 2009, vol. 4, No. 4, article e5402, 8 pages <DOI:10.1371/journal.pone.0005402>.

Majava, V. et al., "Interaction between the C-terminal region of human myelin basic protein and calmodulin: analysis of complex formation and solution structure", BMC Structural Biology, Feb. 2008, vol. 8, No. 10, 18 pages <DOI:10.1186/1472-6807-8-10>.

Makino, K. et al., "Electrophoretic Mobility of a Colloidal Particle with Constant Surface Charge Density", Langmuir, Dec. 2010 (available online Nov. 2010), vol. 26, No. 23, pp. 18016-18019 <DOI:10.1021/la1035745>.

Martin, N. et al., "Prevention of Thermally Induced Aggregation of IgG Antibodies by Noncovalent Interaction with Poly(acrylate) Derivatives", Biomacromolecules, Aug. 2014 (available online Jul. 2014), vol. 15, No. 8, pp. 2952-2962 <DOI:10.1021/bm5005756>.

Matteini, P. et al., "Site-Selective Surface-Enhanced Raman Detection of Proteins", ACS Nano, Jan. 2017 (available online Dec. 2016), vol. 11, No. 1, pp. 918-926 <DOI:10.1021/acsnano.6b07523>.

Olsson, B. et al., "CSF and blood biomarkers for the diagnosis of Alzheimer's disease: a systematic review and meta-analysis", The Lancet Neurology, Jun. 2016 (available online Apr. 2016), vol. 15, No. 7, pp. 673-684 <DOI:10.1016/S1474-4422(16)00070-3>.

Papish, A. et al., "Dynamic Light Scattering Study of Calmodulin-Target Peptide Complexes", Biophysical Journal, Sep. 2002, vol. 83, No. 3, pp. 1455-1464 <DOI:10.1016/S0006-3495(02)73916-7>.

Parmar, A. et al., "Hydration and Hydrodynamic Interactions of Lysozyme: Effects of Chaotropic versus Kosmotropic Ions", Biophysical Journal, Jul. 2009, vol. 97, No. 2, pp. 590-598 <DOI:10.1016/j.bpj.2009.04.045>.

Polanski, M. et al., "A List of Candidate Cancer Biomarkers for Targeted Proteomics", Biomarker Inights, Jan. 2006, vol. 1, pp. 1-48 <DOI:10.1177/117727190600100001>.

Ruggeri, F. et al., "Single-molecule electrometry", Nature Nanotechnology, Mar. 2017, vol. 12, pp. 488-495 <DOI:10.1038/nnano.2017.26>.

Saleh, O., "Perspective: Single polymer mechanics across the force regimes", The Journal of Chemical Physics, May 2015, vol. 142, article 194902, 8 pages <DOI:10.1063/1.4921348>.

Raether "Surface-Plasmons on Smooth and Rough Surfaces and on Gratings" Modem Physics, vol. 111, Springer-Verlag, New York, 1988, 140 pages.

Samori "Scanning Probe Microscopies Beyond Imaging: Manipulation of Molecules and Nanostructures" Wiley-VCH Verlag GmbH & Co. KGaA, Weinheim, 2006, 559 pages.

Santos, R. et al., "A comprehensive map of molecular drug targets", Nature Reviews Drug Discovery, Jan. 2017 (available online Dec. 2016), vol. 16, pp. 19-34 <DOI:10.1038/nrd.2016.230.

Schubert, O. et al., "Quantitative proteomics: challenges and opportunities in basic and applied research", Nature Protocols, Jul. 2017 (available online Jun. 2017), vol. 12, pp. 1289-1294 <DOI:10.1038/nprot.2017.040>.

Seaton, B. et al., "Calcium-induced increase in the radius of gyration and maximum dimension of calmodulin measured by small-angle x-ray scattering", Biochemistry, Nov. 1985, vol. 24, No. 24, pp. 6740-6743 <DOI:10.1021/bi00345a002>.

Shan, X. et al., "Detection of Charges and Molecules with Self-Assembled Nano-Oscillators", Nano Letters, Jul. 2014 (available online Jun. 2014), vol. 14, No. 7, pp. 4151-4157 <DOI:10.1021/nl501805e>.

Sharma, U. et al., "Hydrodynamic radius ladders of proteins", Electrophoresis, Jun. 2005 (available online May 2005), vol. 26, No. 11, pp. 2086-2091 <DOI:10.1002/elps.200410334>.

Shi, T. et al., "Antibody-free, targeted mass-spectrometric approach for quantification of proteins at low picogram per milliliter levels in human plasma/serum", Proceedings of the National Academy of Sciences, Sep. 2012, vol. 109, No. 38, pp. 15395-15400 <DOI:10.1073/pnas.1204366109>.

Sorensen, B. et al., "Calcium binding decreases the stokes radius of calmodulin and mutants R74A, R90A, and R90G", Biophysical Journal, Dec. 1996, vol. 71, No. 6, pp. 3407-3420 <DOI:10.1016/S0006-3495(96)79535-8>.

Sukumar, M. et al., "Opalescent Appearance of an IgG1 Antibody at High Concentrations and its Relationship to Noncovalent Asso-

(56) References Cited

OTHER PUBLICATIONS ciation", Pharmaceutical Research, Jul. 2004, vol. 21, pp. 1087-1093 <DOI:10.1023/B:PHAM.0000032993.98705.73>.

Szymanski, J. et al., "Net Charge and Electrophoretic Mobility of Lysozyme Charge Ladders in Solutions of Nonionic Surfactant", The Journal of Physical Chemistry B, May 2007 (available online Apr. 2007), vol. 111, No. 19, pp. 5503-5510 <DOI:10.1021/jp067511d>.

Takeda, K. et al., "Size and mobility of sodium dodecyl sulfate—bovine serum albumin complex as studied by dynamic light scattering and electrophoretic light scattering", Journal of Colloid and Interface Science, Dec. 1992, vol. 154, No. 2, pp. 385-392 <DOI:10.1016/0021-9797(92)90153-D>.

Weljie, A. et al., "Protein conformational changes studied by diffusion NMR spectroscopy: Application to helix-loop-helix calcium binding proteins", Protein Science, Feb. 2003, vol. 12, No. 2, pp. 228-236 <DOI:10.1110/os.0226203>.

Wilhelm, M. et al., Mass-spectrometry-based draft of the human proteome, Nature, May 2014, vol. 509, pp. 582-587 <DOI:10.1038/nature13319>.

Yamaguchi, A. et al., "Quantitative evaluation of shift of slipping plane and counterion binding to lysozyme by electrophoresis method", Colloid and Polymer Science, Jun. 2016 (available online Mar. 2016), vol. 294, pp. 1019-1026 <DOI:10.1007/s00396-016-3852-4>.

Yang, D. et al., "IgG Charge", Preprints, Nov. 2018, 14 pages <DOI:10.20944/preprints201811.0052.v1>.

Young, G. et al., "Quantitative mass imaging of single biological macromolecules", Science, Apr. 2018, vol. 360, No. 5387, pp. 423-427 <DOI:10.1126/science.aar5839>.

Yu, H. et al., "Achieving High Spatial Resolution Surface Plasmon Resonance Microscopy with Image Reconstruction", Analytical Chemistry, Mar. 2017 (available online Feb. 2017), vol. 89, No. 5, pp. 2704-2707 <DOI:10.1021/acs.analchem.6b05049>.

Yu, S. et al., "Albumin-coated SPIONs: An experimental and theoretical evaluation of protein conformation, binding affinity and competition with serum proteins", Nanoscale, May 2016, vol. 8, pp. 14393-14405 <DOI:10.1039/C6NR01732K>.

Zijlstra, P. et al., "Optical detection of single non-absorbing molecules using the surface plasmon resonance of a gold nanorod", Nature Nanotechnology, Apr. 2012, vol. 7, pp. 379-382 <DOI:10.1038/nnano.2012.51>.

U.S. Appl. No. 16/500,370, Tao et al., filed Oct. 5, 2019.
U.S. Appl. No. 16/613,745, Tao, filed Nov. 14, 2019.
U.S. Appl. No. 16/644,453, Tao et al., filed Mar. 4, 2020.
U.S. Appl. No. 16/857,660, Tao et al., filed Apr. 24, 2020.

* cited by examiner

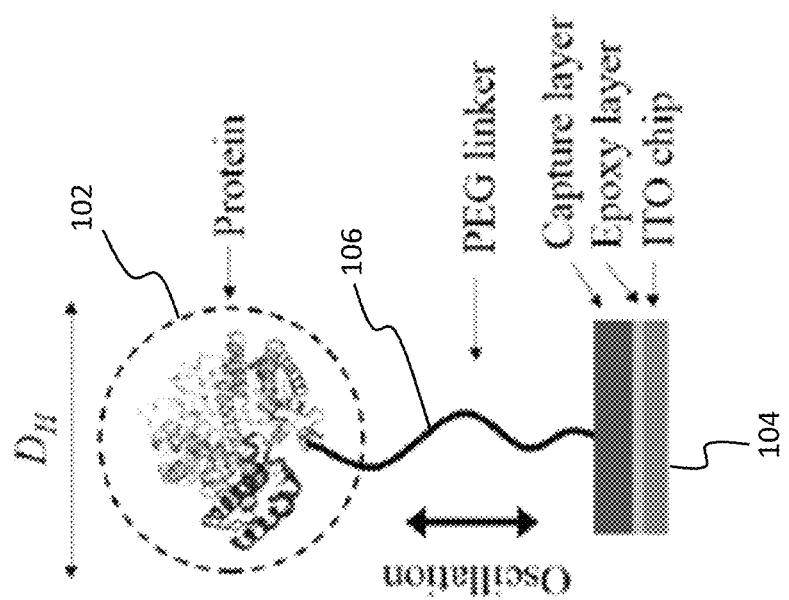
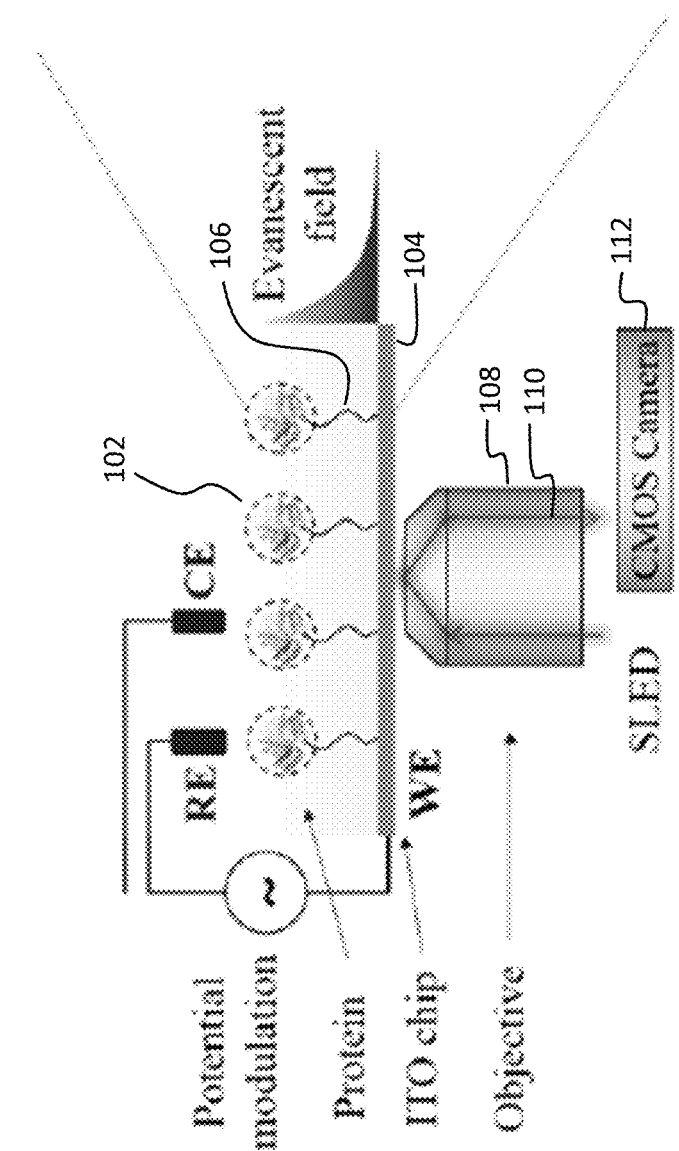
FIG. 1A
FIG. 1B

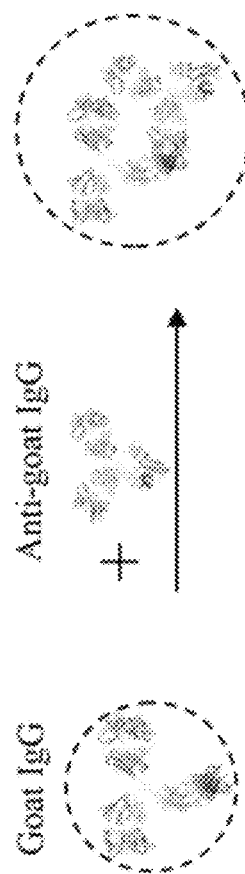
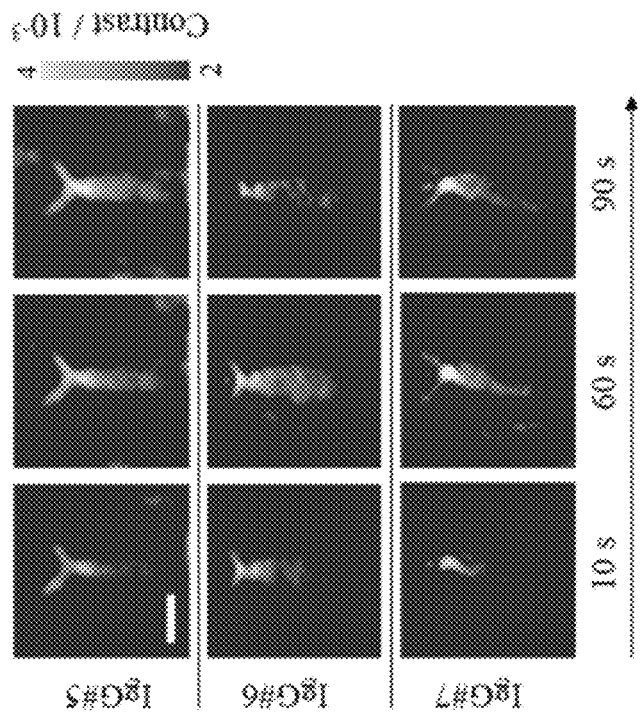
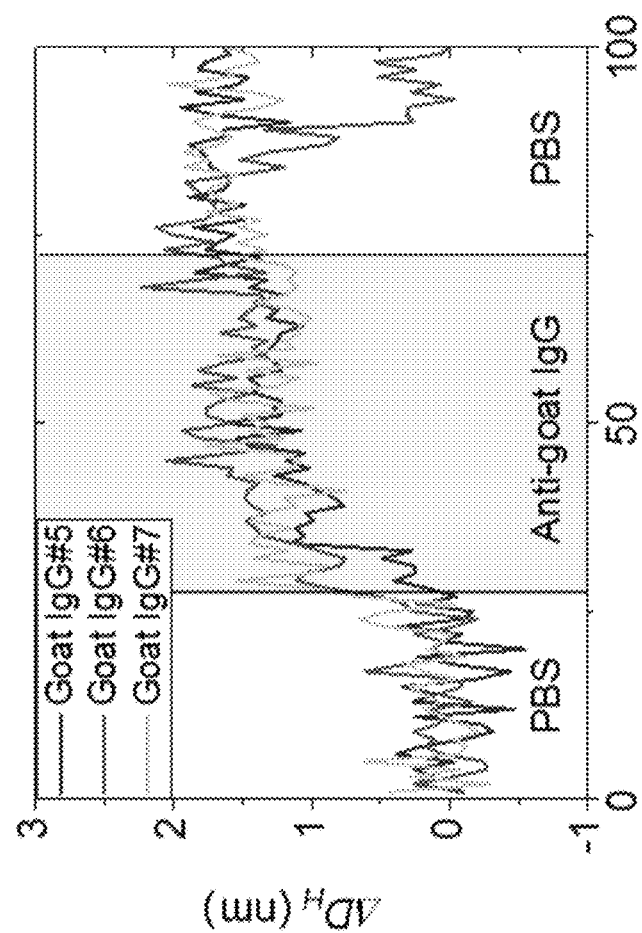
FIG. 3A
FIG. 3B
FIG. 3C

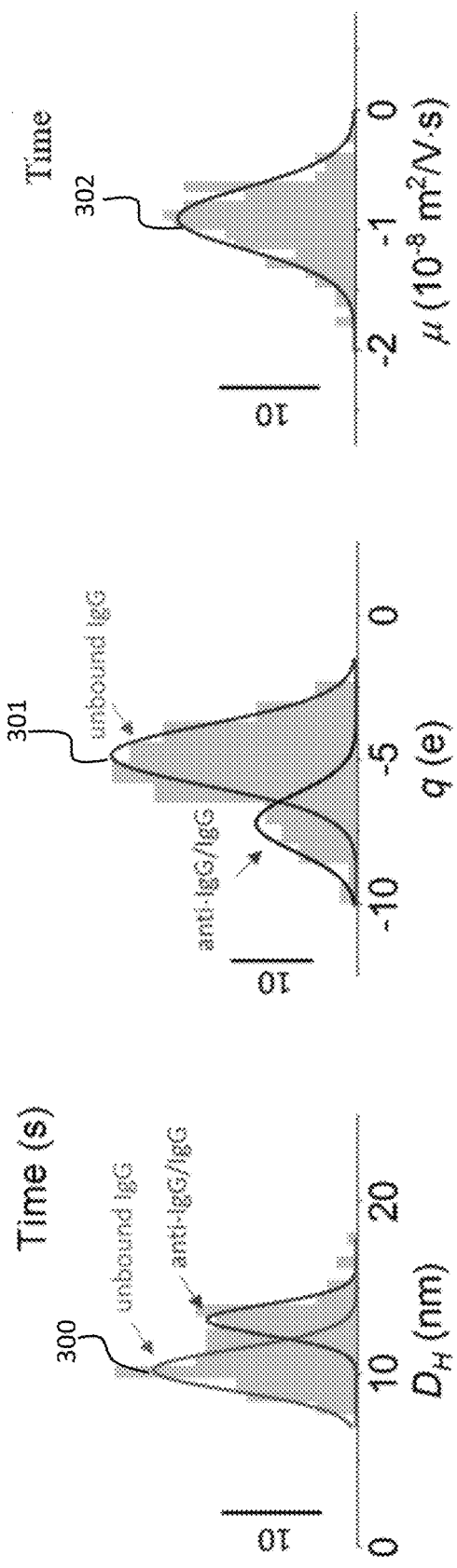
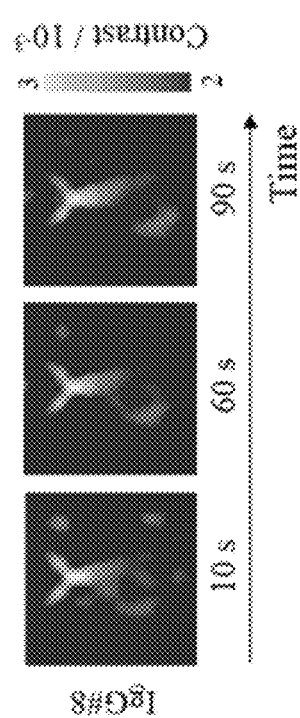
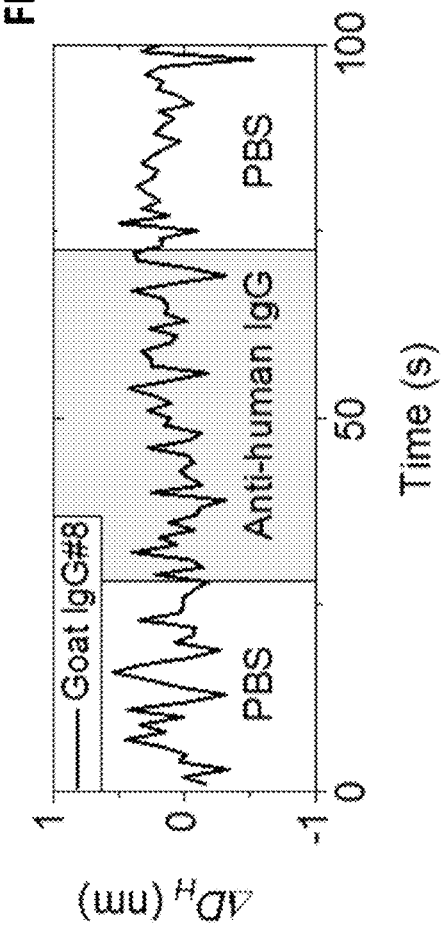
FIG. 3D
FIG. 3E
FIG. 3F

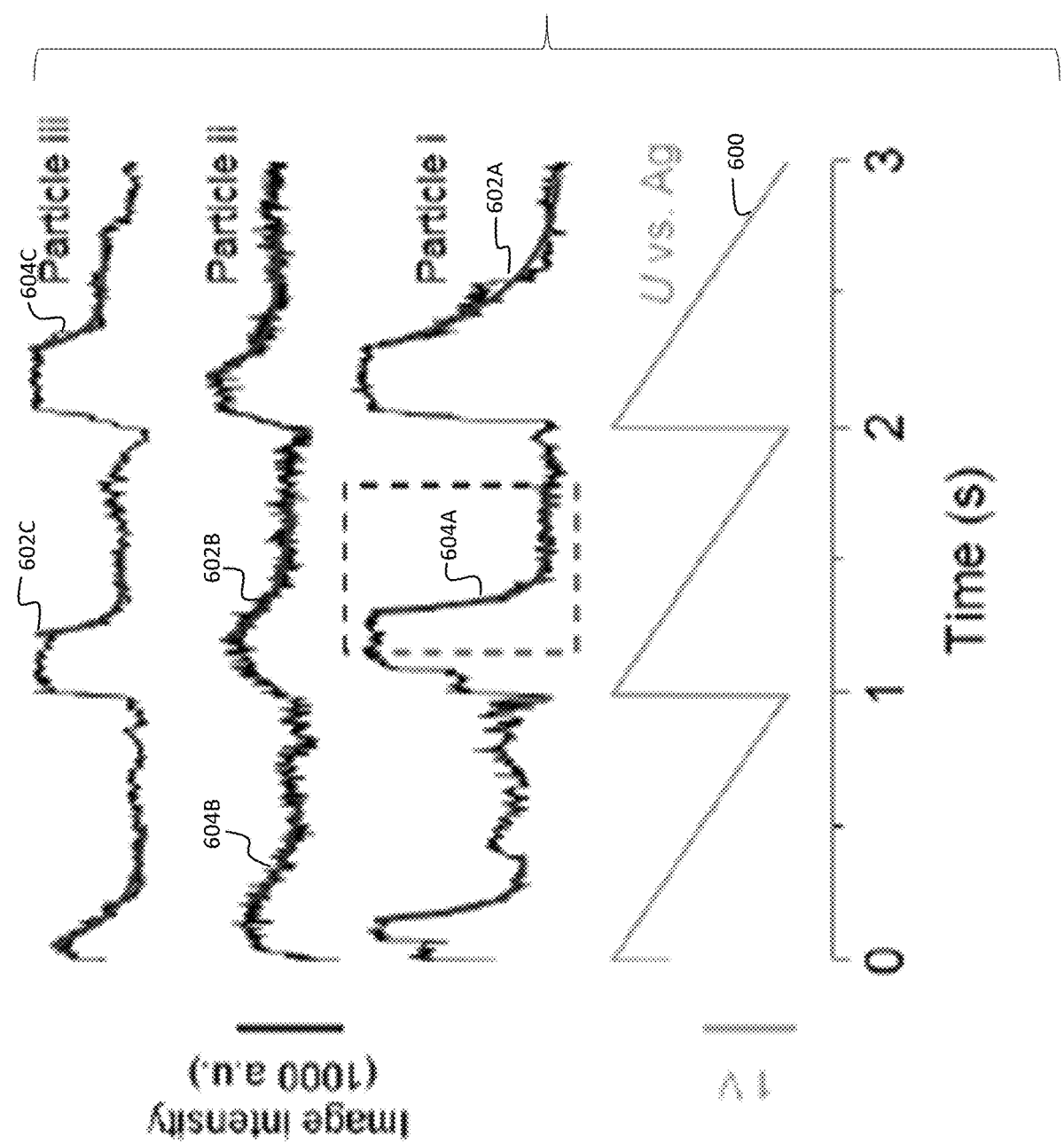

OPTICAL IMAGING OF SINGLE MOLECULE SIZE, CHARGE, MOBILITY, BINDING AND CONFORMATIONAL CHANGE

TECHNICAL FIELD

The present invention relates to single molecule detection and, more particularly, to a method for optical imaging of single protein molecule size, charge, mobility, binding and conformational change.

BACKGROUND

Proteins play a central role in nearly every aspect of cellular functions.[1-3] They also serve as drugs, drug targets and disease biomarkers.[4, 5] Detecting and identifying proteins are thus the basic tasks in biomedical research, and in disease diagnosis and therapeutics.[6-8] Various technologies have been developed for protein analysis, and the most important ones include liquid chromatography (LC), mass spectrometry (MS) and the Western Blot.[9-13] These technologies separate proteins based on their physical characteristics, such as charge and size, and identify them based on the mass or binding to antibodies. Although ubiquitous in both biomedical industry and research labs, they are time consuming and destructive, involving protein fragmentation and denaturation.[9, 10] They also lack single molecule detection capability. Here the inventors report a method to image single proteins without labels, measure the size, charge and mobility of each protein simultaneously, and analyze antibody binding to the proteins in real time. The proteins are resolved individually in space on a surface, thus requiring no separation. The simultaneous charge and size quantification, together with specific antibody binding, allow identification of the protein. The method is analogous to the LC, MS and Western Blot technologies, but achieved at the single molecule level. The inventors further show that the method allows detection of conformational changes of single proteins.

Several technologies have been demonstrated to detect single proteins without using fluorescent labels.[14-16] One is to detect refractive index changes of proteins resulted from local heating by light.[14] A more direct method is to measure protein binding to plasmonic hotspots on the nanorod surface from plasmonic absorption.[15] Because the plasmonic field is non-uniform on the surface, the protein binding-induced plasmonic absorption depends on not only the size of the protein, but also where the protein binds, which makes it difficult to quantify the size of the protein. Recently, a light interference method has been developed to quantify the protein size based on optical scattering intensity.[16] These label-free methods are attractive for protein analysis because they measure the size, an intrinsic property of proteins. However, size alone provides only limited information. Different proteins may have a similar size, but drastically different conformations, charges and binding affinities to other proteins.[17-19] This is the reason that the popular protein analysis technologies separate proteins based on the size (mass) and charge (e.g., Western Blot, LC and MS), and identify proteins based on their specific bindings to antibodies (e.g., Western Blot and ELISA). The method in the present work can image the size and charge of each individual protein simultaneously, and measures conformation changes in the protein and specific binding to its antibody.

Previously, the inventors hereof have studied nano- and micro-particles, including gold, silica and virion particles, tethered to a gold surface[59,60,61]. They excited surface plasmon waves on the gold surface and obtained plasmonic images of the particles, from which they measured molecular binding to the surface of the particles. Because the measured properties are primarily due to the particles, these works failed to obtain the size and other intrinsic features of the molecules. These prior studies also failed to detect single molecules. A serious problem in these previous studies was presented by the strong background response of the gold film associated with surface plasmon resonance, which is superimposed on the weak signals from the particles.

In contrast to and in an advance over the previous studies, the present invention directly links single protein molecules to a surface. Because protein molecules produce weak optical signals, the present invention examines various surfaces and identified an ITO-coated glass slides produces minimum background yet sufficiently conductive for the inventors to apply an electric field to it. An additional innovation is the discovery of interference of light from the ITO surface and from the protein molecules, which produces high contrast images for small objects (protein molecules). In advances over prior work, the present invention provides accurate determination of protein charge, size and mobility. To accomplish these advances, accurate measurement of the electric field applied to the surface is essential and is achieved with the methods and procedures disclosed hereinbelow.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A method for optical imaging of single protein molecules including tethering single protein molecules via a flexible polymer linker to a glass slide having a surface coated with an indium tin oxide (ITO) so that the single protein molecules are tethered to the coated surface is disclosed. The single protein molecules are driven into oscillation by applying an alternating electric field to the coated surface and the glass slide is located in the field of view of an objective lens. Incident light is directed onto the coated surface from an angle to generate an evanescent field and produce scattered light. The scattered light is collected and imaged by a CMOS imager to record a sequence of images of the scattered light. A filter (e.g., Fast Fourier Transform or FFT) is applied to each pixel of the recorded image sequence to produce an oscillation amplitude image from which size, charge, and mobility of the plurality of single protein molecules can be determined.

BRIEF DESCRIPTION OF THE DRAWINGS

While the novel features of certain embodiments of the invention are set forth with particularity in the appended claims, the invention, both as to organization and content, will be better understood and appreciated, along with other objects and features thereof, from the following detailed description taken in conjunction with the drawings, in which:

FIG. 1A shows an example of protein molecules tethered to an indium tin oxide (ITO) surface with soft polyethylene glycol (PEG) linkers and imaged by a TIR microscope.

FIG. 1B shows an example of surface modification of the ITO chip of FIG. 1A.

FIG. 3A shows an example for identifying single proteins via antibody binding where anti-goat IgG is introduced to bind with PEG tethered goat IgG.

FIG. 3B shows an example for identifying single proteins via antibody binding where binding/unbinding of anti-goat IgG with three goat IgG molecules is tracked in real-time, showing diameter changes associated with the binding and unbinding events.

FIG. 3C shows an example of snapshots of the three IgG molecules captured before, during and after the binding experiment in FIG. 3B.

FIG. 3D shows an example of statistical analysis of 137 goat IgG molecules showing the diameter ($D_H$), charge (q) and mobility (μ) histograms of the molecules after incubation.

FIG. 3E shows an example of a plot derived from a control experiment using anti-human IgG, showing no detectable changes in the diameter of IgG.

FIG. 3F shows an example of snapshots of the three IgG molecules captured before, during and after the binding control experiment in FIG. 3E.

FIG. 6D shows examples of plots representing intensity change in each cycle fitted to exponential decay.

Figure 1C:
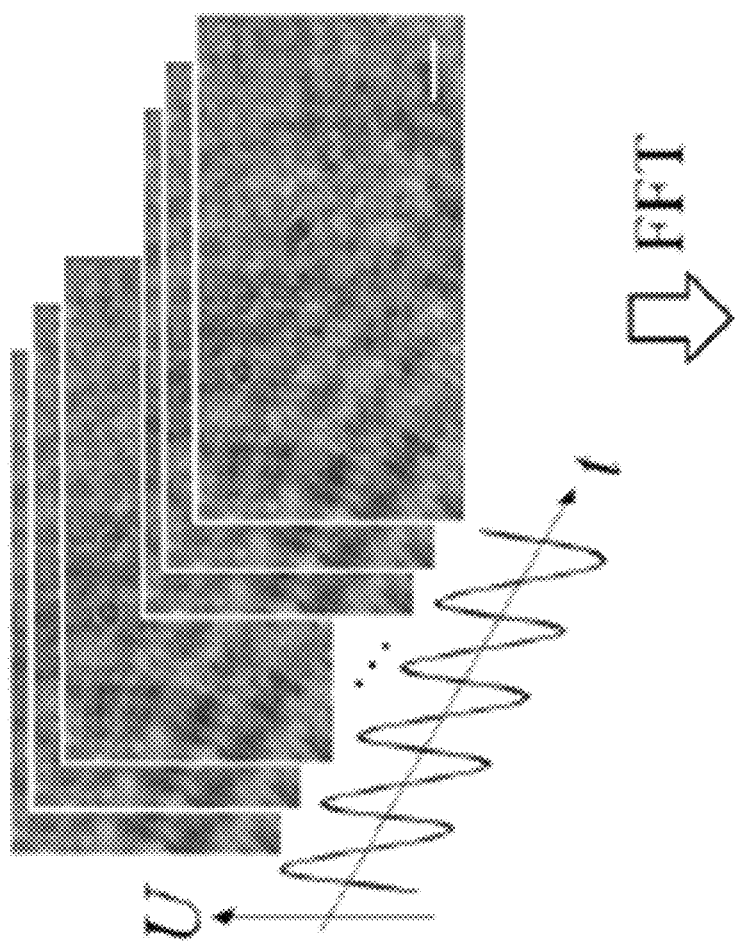
FIG. 1C shows an example of images obtained for oscillating individual BSA molecules.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

The following disclosure describes a system and method for label free detection, identification and quantification of single proteins. Several features of methods and systems in accordance with example embodiments are set forth and described in the figures. It will be appreciated that methods and systems in accordance with other example embodiments can include additional procedures or features different than those shown in the figures. Example embodiments are described herein with respect to systems and methods for label free detection, identification and quantification of single proteins. However, it will be understood that these examples are for the purpose of illustrating the principles, and that the invention is not so limited.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of protein analysis:

The articles "a" or "an" and the phrase "at least one" as used herein refers to one or more.

As used herein, "plurality" is understood to mean more than one. For example, a plurality refers to at least two, three, four, five, ten, 25, 50, 75, 100, 1,000, 10,000 or more.

"Obtaining" is understood herein as manufacturing, purchasing, or otherwise coming into possession of.

As used herein "real time" is understood to mean relating to a system in which input data is processed within milliseconds so that it is available virtually immediately as feedback, e.g., in a computer system.

In order to promote a better understanding of the novel teachings presented herein, a brief overview of the differences between the present disclosure and the state of the art is presented immediately below.

In accordance with the methods disclosed herein, the inventors have developed a label free technology to image single proteins, and to quantify the size, mobility and charge of single proteins simultaneously. The precisions for the size and charge achieved with the present setup are 1.0 nm and 0.3 e, respectively. The technology can also monitor protein-protein interactions and ligand binding-induced conformation changes in single proteins. Using these capabilities, the inventors have analyzed single proteins based on size, charge, mobility and specific binding to antibodies. This resembles the widely used Western Blot and ELISA technologies, but achieved at the single molecule level without separation and denaturation of the proteins. The inventors anticipate that the technology will open new paths to study various processes of proteins, including conformation changes, molecular binding and post-translational modifications of proteins, and to detect disease biomarkers at the single molecule level without labels.

Protein analysis has heretofore relied on electrophoresis, mass spectroscopy and immunoassay, which separate, detect and identify proteins based on the size, charge, mobility and binding to antibodies. However, until the advances made by the inventors as disclosed herein, measuring these quantities at the single molecule level has not been possible. According to the new and novel methods disclosed herein, the inventors tether a protein to a surface with a flexible polymer, drive the protein into mechanical oscillation with an alternating electric field, and image the protein oscillation with a near field imaging method, from which the inventors determine the size, charge, and mobility of the protein. The inventors also measure binding of antibodies to single proteins and ligand binding-induced conformational changes in single proteins. This work provides new capabilities for protein analysis and disease biomarker detection at the single molecule level. In addition to proteins, these new capabilities apply to other molecules, such as DNA and RNA molecules.

Imaging Single Proteins and Mechanical Oscillations.

Referring now jointly to FIG. 1A and FIG. 1B, FIG. 1A shows an example of protein molecules tethered to an indium tin oxide (ITO) surface with soft polyethylene glycol (PEG) linkers and imaged by a Total internal reflection (TIR) microscope and FIG. 1B shows an example of surface modification of the ITO chip of FIG. 1A. To achieve single protein imaging capability without labels, single protein molecules 102 were tethered to an indium tin oxide (ITO) coated glass slide 104 via a flexible polymer linker 106 (for example, polyethylene glycol (PEG) or equivalents) and the proteins were driven into oscillation by applying an alternating electric field to the ITO surface. The ITO slide is placed on the objective 108 of an inverted optical microscope, and incident light 110 is directed onto the ITO surface via the objective from an appropriate angle to generate an evanescent field near the ITO surface. The evanescent field interacts with the oscillating protein and leads to scattered light, which is collected by the same objective and imaged by a CMOS imager 112. Because the evanescent field is localized near the ITO surface, the scattered light is extremely sensitive to the protein-surface distance. In some useful examples, the length of PEG linkers can range from a few nm to 200 nm. Useful alternative linkers include any polymer and polymer-like molecules, such as single-stranded DNA, double-stranded DNA, DNA origami, RNA, peptide nucleic acid (PNA), and carbon nanotube.

In one example the alternating electric field (or potential) was applied with a three-electrode electrochemical configuration to drive the molecules into oscillation, where WE, RE, and CE are the working (the ITO surface), quasi-reference (Ag wire) and counter electrode (Pt coil), respectively. In one example the polymer linker was a 63 nm long polyethylene glycol (PEG), which couples the proteins to the ITO surface via surface chemistry described in the method below.

Figure 1D:
FIG. 1D shows an example of resolving single BSA molecules using Fast Fourier Transform (FFT).
Figure 1E:
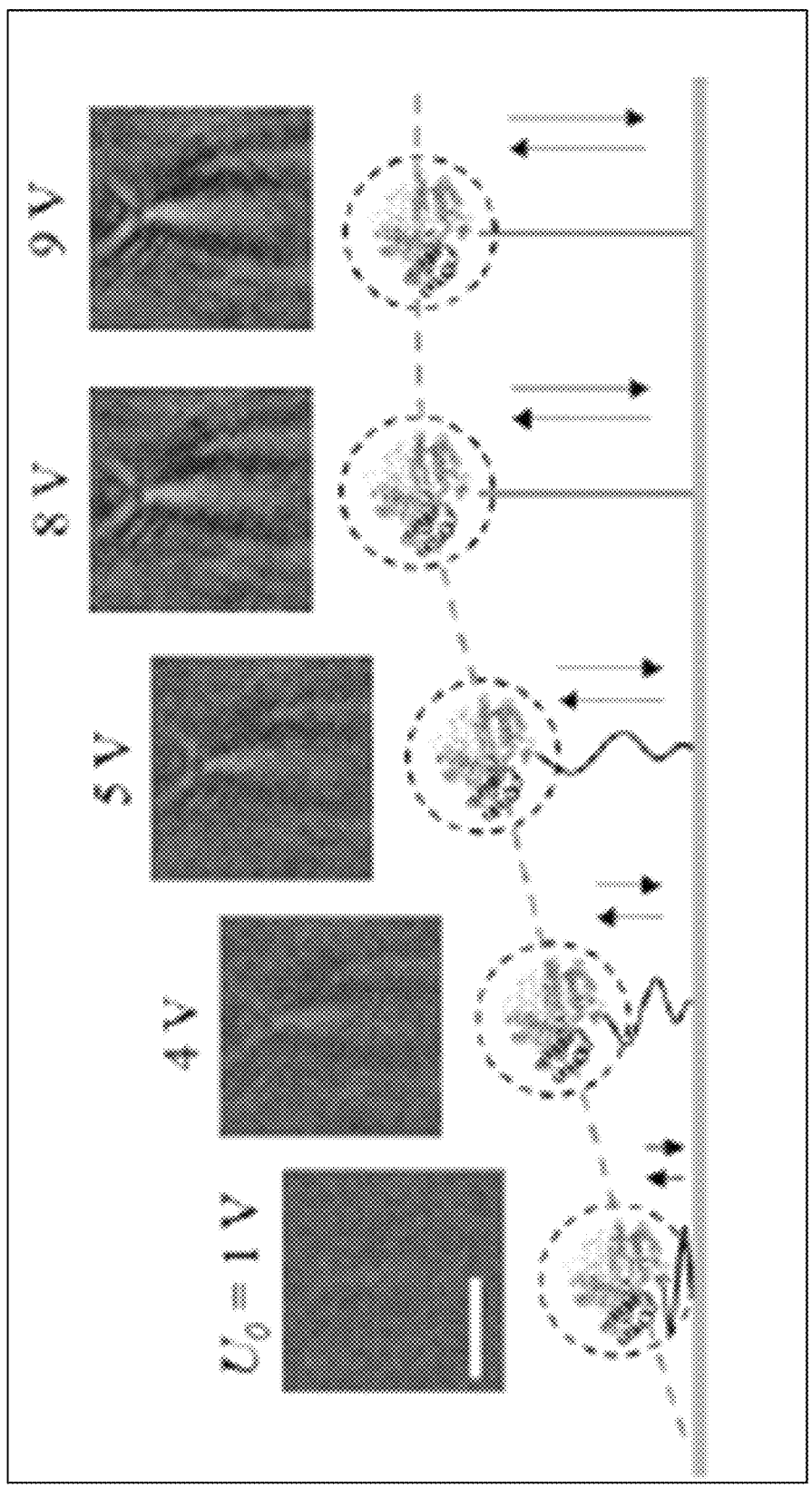
FIG. 1E shows an example of oscillation amplitude image contrast vs. applied potential for single molecules, showing an increase regime at low fields, and a plateau regime due to fully stretching of a PEG linker at high fields.

Continuing the process description and now referring jointly to FIG. 1C and FIG. 1D, FIG. 1C shows an example of images obtained for oscillating individual BSA molecules and FIG. 1D shows an example of resolving single BSA molecules using Fast Fourier Transform (FFT). As the protein oscillates, so does the scattered light, which is recorded as an image sequence (FIG. 1C). Fast Fourier Transform (FFT) was performed on each pixel of the recorded image sequence to remove noise at frequencies other than the frequency of the applied field. The FFT image resolves a single protein as a bright spot with a parabolic tail that arises from the interference between the scattering of the evanescent wave by the protein and reflection from the surface (FIG. 1D) (see below for imaging principle). [20] The FFT image contrast image measures the oscillation amplitude (referred to as oscillation amplitude image), which provides size, charge, and mobility of the protein as the inventors show below. Scale bars in FIGS. 1C, 1D and 1E represent 3 μm.

In one example, an FFT algorithm comprises a known computer processor implemented FFT algorithm that decomposes an image into its real and imaginary components which is a representation of the image in the frequency domain. If the input signal is an image then the number of frequencies in the frequency domain is equal to the number of pixels in the image or spatial domain. An inverse transform re-transforms the frequencies to the image in the spatial domain. As is understood by those skilled in the art, to "apply" an FFT algorithm to an image means to transform the image pixels in the spatial domain by calculating a frequency domain equivalent transform for the image pixels.

In one example, the oscillation of the individual molecules (bovine serum albumin (BSA)) is imaged at 800 frames/s, where the potential and frequency are 8 V and 80 Hz, respectively. In one example, a Fast Fourier transform (FFT) filter is applied to the time sequence of images shown in FIG. 1D to produce an oscillation amplitude image, which resolves single BSA molecules.

The protein oscillation is determined by the entropic force of the PEG linker and driving force of the applied field, and its oscillation amplitude ($\Delta z_0$) is given by $$\Delta z_0 = \frac{E_0(\Delta z_0, U_0)}{k_{PEG}} q, \quad (1)$$

where $E_0(\Delta_{z0}, U_0)$ is the amplitude of the applied field, which is a function of protein-ITO surface distance $\Delta z_0$ and surface potential $U_0$, and $k_{PEG}$ is the entropic spring constant of the PEG linker (described below). Eq. 1 shows that the oscillation amplitude is proportional to the electric field, but this is valid only at low fields (or at low applied potentials), where the oscillation amplitude is smaller than the PEG linker length.

Figure 1F:
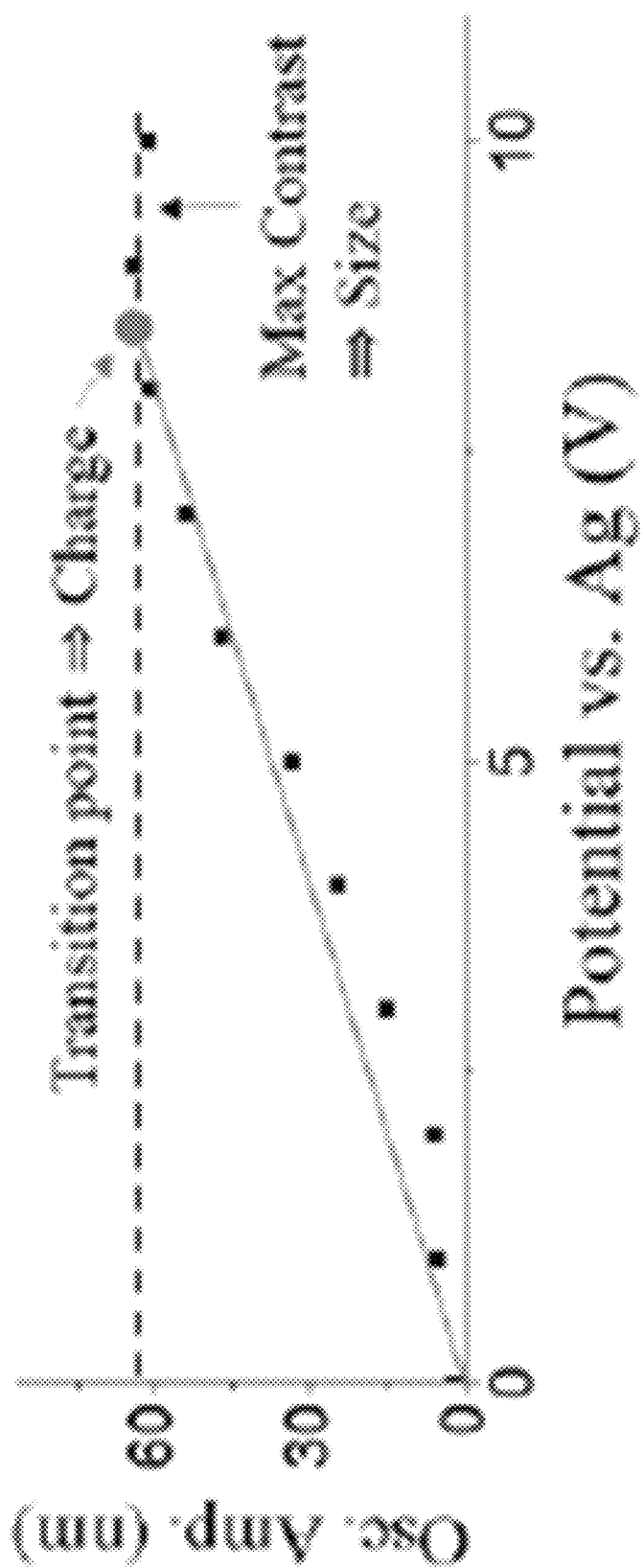
FIG. 1F shows an example of oscillation amplitude of a BSA molecule vs. potential, from which the hydrodynamic diameter, charge and mobility of the molecule are determined.

Continuing the process description and now referring jointly to FIG. 1E and FIG. 1F, FIG. 1E shows an example of oscillation amplitude image contrast vs. applied potential for single molecules, showing an increase regime at low fields, and a plateau regime due to fully stretching of a PEG linker at high fields and FIG. 1F shows an example of oscillation amplitude of a BSA molecule vs. potential, from which the hydrodynamic diameter, charge and mobility of the molecule are determined. When the field or potential is sufficiently large, the inventors expect that the linker becomes stretched and the amplitude reaches a plateau (FIG. 1E). This behavior has been confirmed for all the proteins studied here, and FIGS. 1E and 1F show the results for bovine serum albumin (BSA) as an example. Referring specifically to FIG. 1E, one example of oscillation amplitude image contrast vs. applied potential is plotted, showing an increase regime at low fields(Potential=0), and a plateau regime due to fully stretching of the PEG linker at high fields(Potential >7).

Figure 5B:
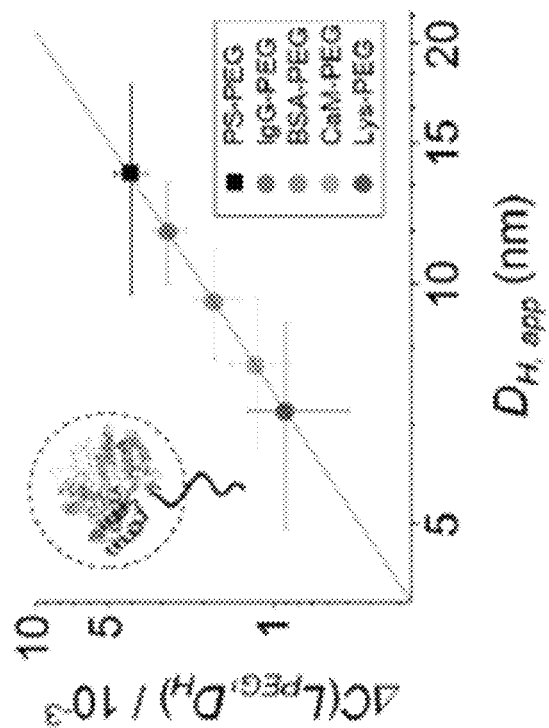
FIG. 5B shows an example of a plot for determining protein size ($D_H$, app) from image contrast change, $ΔC(L_{PEG}, D_H)$.
Figure 5A:
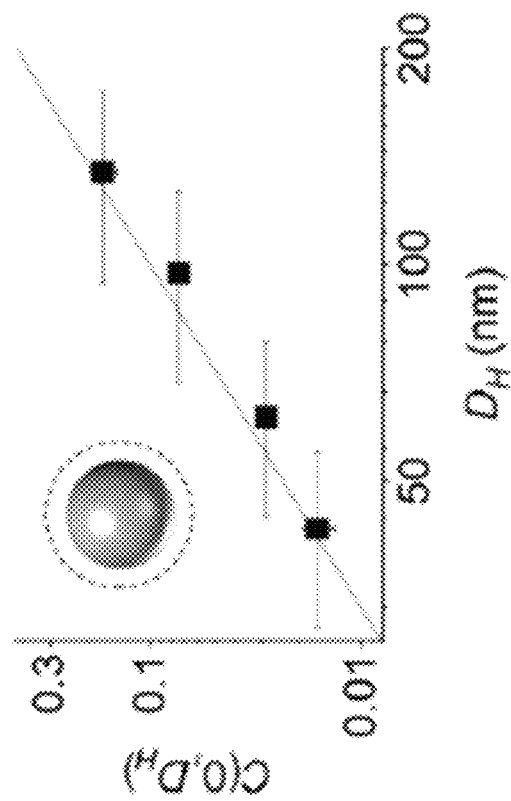
FIG. 5A shows an example of a plot representing image contrast vs. size for polystyrene (PS) particles.

The evanescent field decays exponentially from the ITO surface into the solution with a decay constant of d (on the order of a few hundred nm). Consequently, the oscillation amplitude image contrast, $\Delta C (\Delta z_0, D_H)$, is given by $$\frac{\Delta C(\Delta z_0, D_H)}{C(0, D_H)} = 1 - \exp\left(-\frac{\Delta z_0}{d}\right), \quad (2)$$

where $D_H$ is the protein hydrodynamic diameter and $C(0, D_H)$ is the protein FFT image contrast at zero oscillation amplitude ($\Delta z_0=0$). In the high-field plateau regime, the PEG linker is stretched, such that $\Delta z$ approaches the PEG length ($L_{PEG}$), and the corresponding FFT image contrast, $\Delta C(\Delta z_0=L_{PEG}, D_H)$, is maximum. From the measured $\Delta C(\Delta z_0=L_{PEG}, D_H)$, Eq. 2 allows determination of $C(0, D_H)$. Because $C(0, D_H)$ depends on the protein size, knowing $C(0, D_H)$ allows determination of $D_H$ with a calibration curve (FIG. 5A-FIG. 5B, see also Methods). Once $C(0, D_H)$ and $\Delta C (\Delta z_0, D_H)$ are known, $\Delta z_0$ can be determined with Eq. 2. The charge of protein (q) is obtained with Eq. 1 near the transition from the low-field linear to the high-field plateau regimes (FIG. 1F). The electric field at the transition point, $E_0(\Delta z_0=L_{PEG}, U_0=U_{trans})$, is measured experimentally. The protein mobility (μ) is related to the effective charge (q) and size ($D_H$) of the protein by $\mu=q/(3\pi\eta D_H)$, where η is the buffer viscosity. This relation allows determination of μ from q and $D_H$.

Quantifying the Size, Charge and Mobility of Single Protein Molecules

Figure 2A:
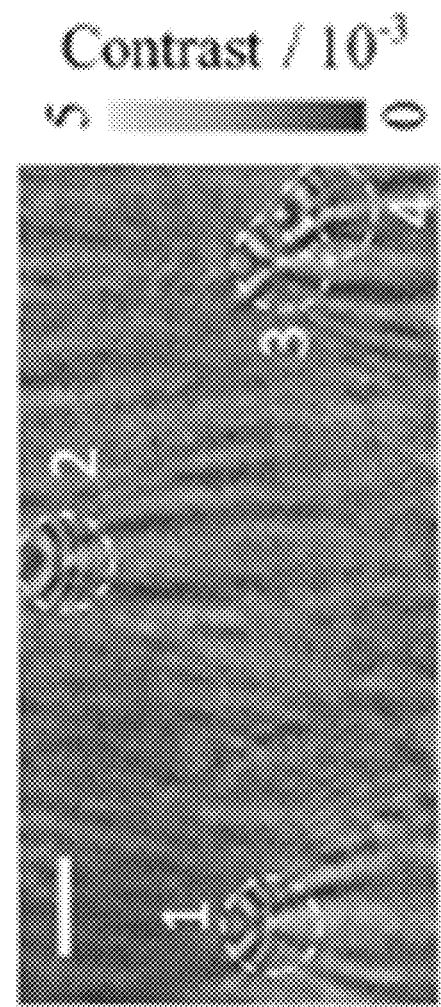
FIG. 2A shows an example of an oscillation amplitude image of immunoglobulin G (IgG) molecules measured at $U_0=8$ V.
Figure 2A:
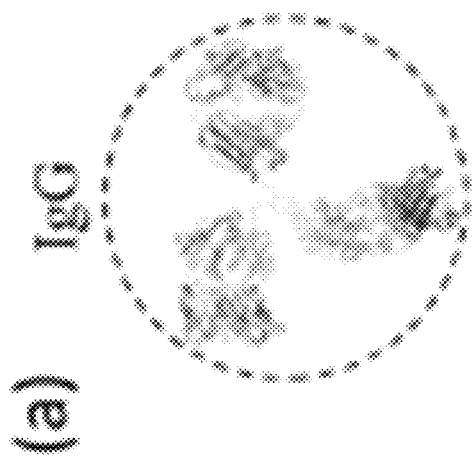

Referring now to FIG. 2A, an example of an oscillation amplitude image of immunoglobulin G (IgG) molecules measured at $U_0=8$ V is shown. The inventors applied the method described hereinabove to proteins with different sizes and charges. The first example is goat immunoglobulin G (IgG), which has a molecular weight of 150 kDa and is negatively charged in the buffer (pH=7.4). The oscillation amplitude image of several IgG molecules at $U_0=8$ V. Scale bars in FIG. 2A, FIG. 2D and FIG. 2G represent 3 μm.

Figure 2B:
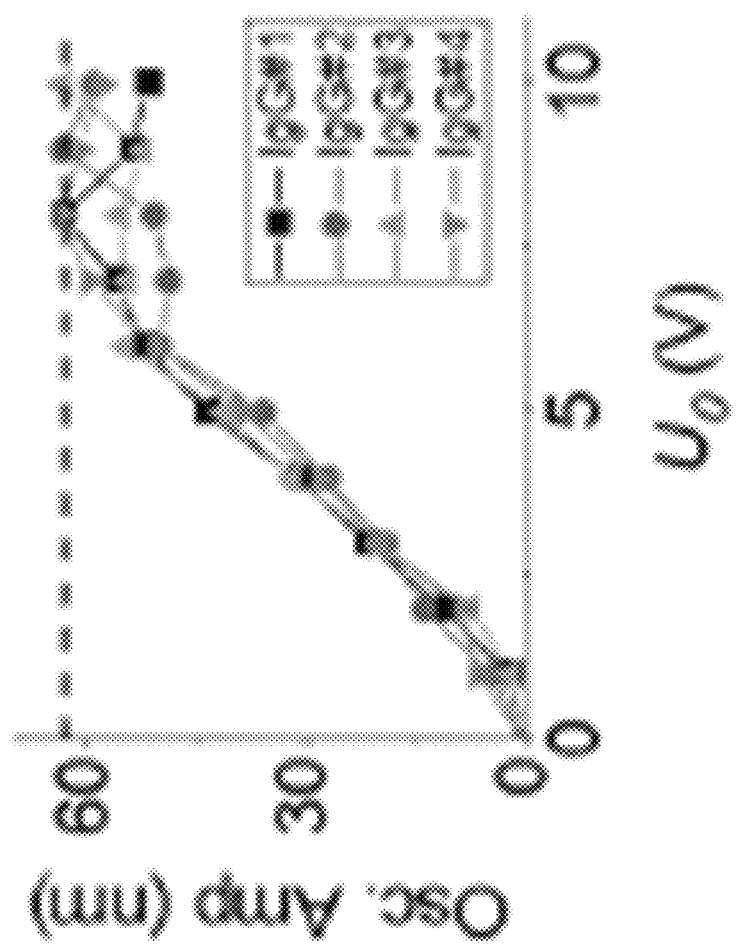
FIG. 2B shows an example of oscillation amplitude vs. applied potential plots of the IgG molecules marked in FIG. 2A, from which diameter ($D_H$), charge (q), and mobility (μ) are obtained.
Figure 7A:
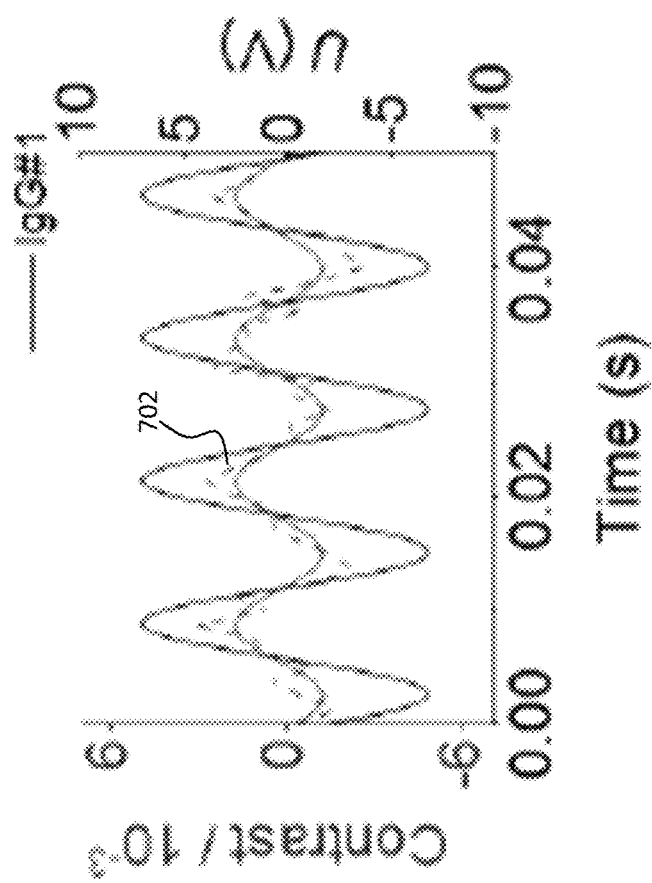
FIG. 7A shows an example of oscillation of an IgG molecule with potential (U).

Referring now to FIG. 2B, an example of oscillation amplitude vs. applied potential plots of the IgG molecules marked in FIG. 2A, from which diameter ($D_H$), charge (q), and mobility (μ) are obtained is shown. See Table 1 below for a tabulation of experimental data. The image contrast and the extracted oscillation amplitude of IgG increase with the electric field below 8 V, and reach plateau values above 8 V. From the transition points of the oscillation amplitude vs. potential plots, the inventors obtained the charge of the individual IgG molecules. From the plateau regime, the determined the diameter of IgG, and then mobility of each IgG molecule. The oscillation amplitude is in phase (~0° phase shift) with the applied potential (as shown in FIG. 7A, for example), confirming negative charge of IgG.

TABLE 1

Size ($D_H$), charge (q), and mobility (μ) of the individual protein as used
for calculating and plotting Osc, Amp(nm) v. $U_0$(V) in FIG. 2B, 2E and 2H.

|  | IgG | | | | Lysozyme | | | | BSA | | |
| --- | --- | --- | --- | --- | --- | --- | --- | --- | --- | --- | --- |
|  | #1 | #2 | #3 | #4 | #1 | #2 | #3 | #4 | #1 | #2 | #3 |
| $D_H$ (nm) | 11.8 | 10.7 | 11.7 | 11.3 | 3.9 | 5.2 | 5.0 | 5.0 | 8.4 | 7.6 | 8.7 |
| q (e) | −6.3 | −5.4 | −6.4 | −6.2 | 4.9 | 5.8 | 4.3 | 5.8 | −6.6 | −6.7 | −5.4 |
| μ ($10^{-8}$ m²/V · s) | −1.0 | −0.97 | −1.0 | −1.1 | 2.4 | 2.1 | 1.6 | 2.2 | −1.5 | −1.7 | −1.2 |

Figure 2C:
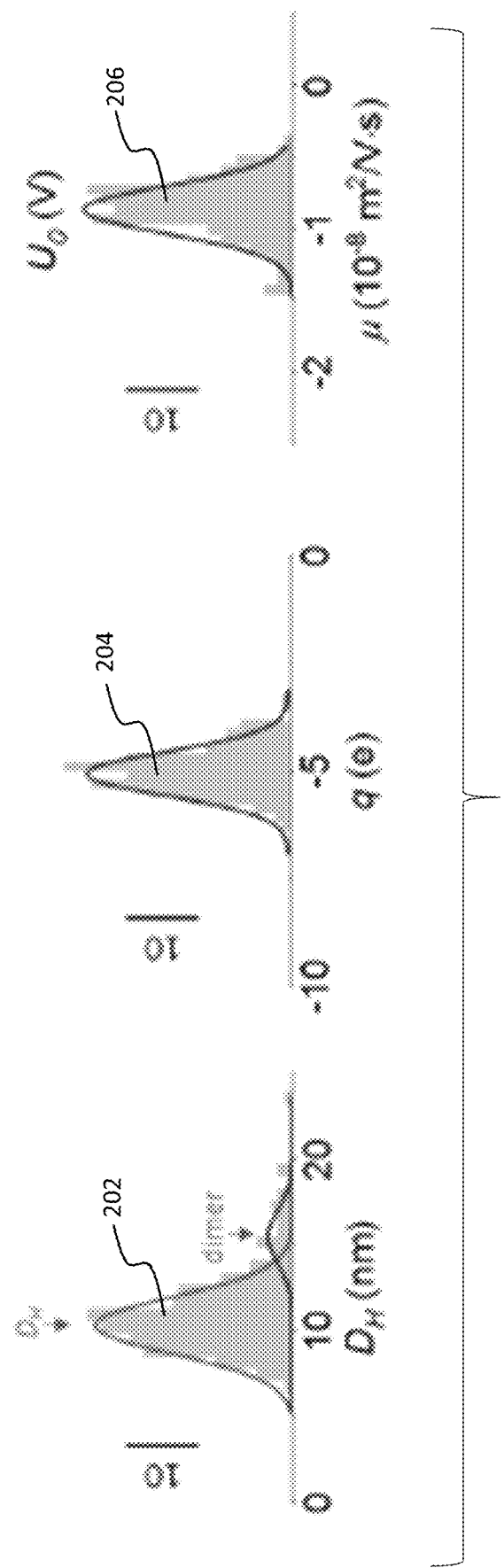
FIG. 2C shows an example of statistical analysis of $D_H$, q, and μ measured for 186 IgG molecules, where the fitted curves are Gaussian fittings to the histograms.
Figure 2D:
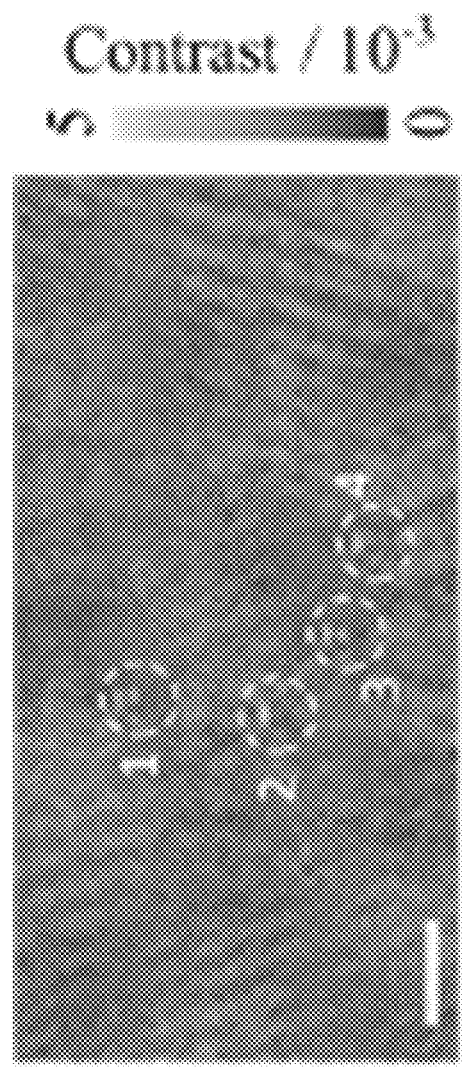
FIG. 2D shows an example of an oscillation amplitude image of lysozyme molecules measured at potential of 9 V.
Figure 2D:
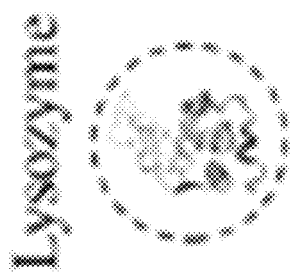

Referring now to FIG. 2C an example of statistical analysis of $D_H$, q, and μ measured for 186 IgG molecules, where the fitted curves are Gaussian fittings to the histograms is shown. The histograms for the diameter 202, charge 204 and mobility 206 were plotted and showed pronounced peaks at 10.4 nm, −5.0 e (e, the elementary charge, is $1.6 \times 10^{-19}$ C) and $-0.86 \times 10^{-8}$ m²V⁻¹s⁻¹, respectively. The mean size and mobility agree with the values from dynamic light scattering experiments for IgG (as shown in FIG. 5C) and reported in literature (See Tables 3 and 4 below), and the mean charge is also close to the estimated value (See Table 5 below). The agreements of the diameter, charge and mobility with the reference experiments and literature support that the oscillation amplitude images are primarily due to single molecules. The standard deviations of the diameter (3.4 nm) and charge (1.2 e) histograms are much smaller than the mean values (10.4 nm and −5.0 e). The diameter histogram displays a small secondary peak located at a larger diameter, which is attributed to formation of dimers.

Referring now to FIG. 2D an example of an oscillation amplitude image of lysozyme molecules measured at potential of 9 V is shown. The second example comprised analysis of lysozyme molecules. The inventors applied the method to lysozyme (MW=14 kDa), a much smaller protein than IgG. Lysozyme has lower image contrast than IgG because of its smaller size. The image intensity oscillation is out of phase (~180° phase shift) with the applied potential (FIG. 7C). This is the opposite of IgG, but expected because lysozyme is positively charged at pH=7.4. Similar to IgG, the lysozyme oscillation amplitude increases with the field (<9 V) and then approaches a plateau as the PEG linker reaches its maximum stretching length (shown in FIG. 2E). The inventors determined $D_H$, q and μ of the individual lysozyme molecules and constructed histograms for these quantities (FIG. 2F). The mean values of $D_H$, q and μ are 4.1 nm, 4.3 e and $1.8 \times 10^{-8}$ m²V⁻¹s⁻¹, respectively. The measured $D_H$ and μ are consistent with the dynamic light scattering data, and the charge agrees with the expected value (Table 5).

Figure 2E:
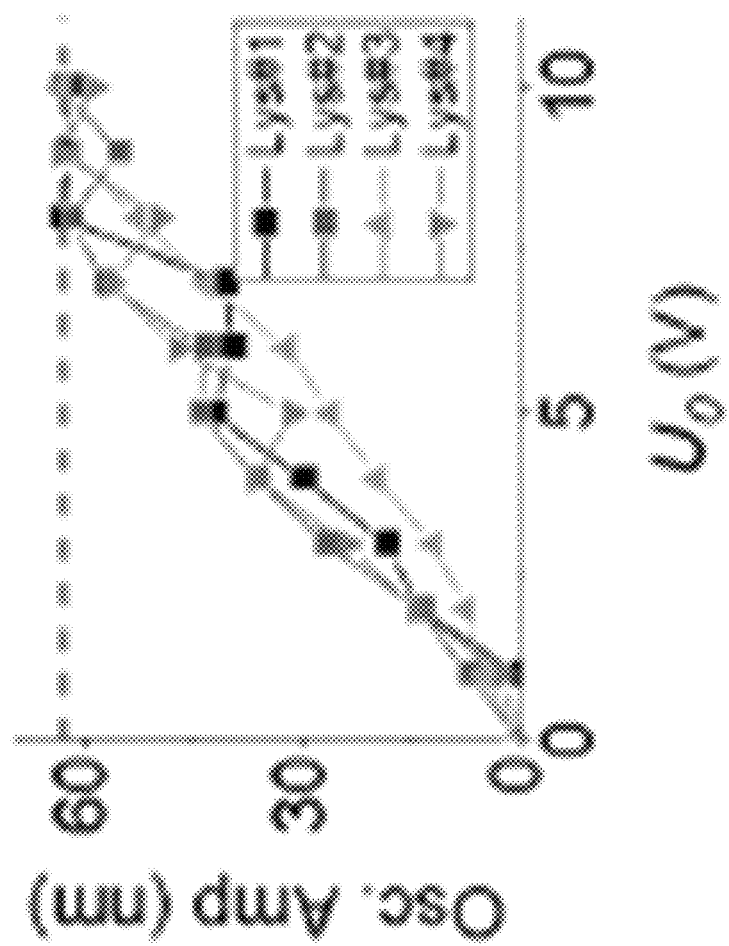
FIG. 2E shows an example of oscillation amplitude vs. applied potential plots of the lysozyme molecules marked in FIG. 2D.
Figure 2F:
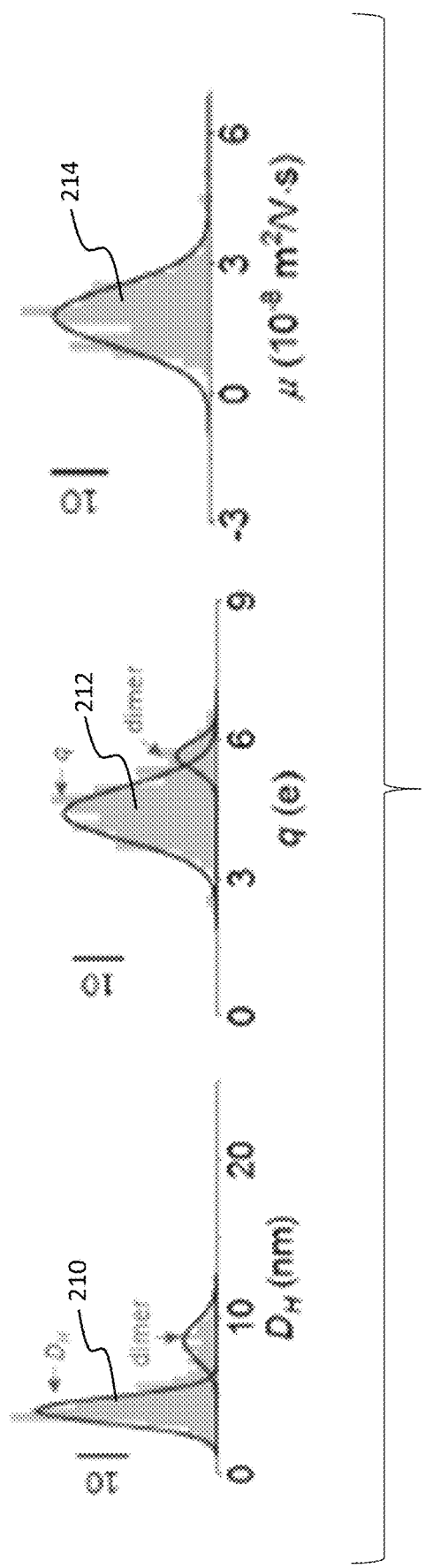
FIG. 2F shows an example of statistical analysis of $D_H$, q, and μ for 246 lysozyme molecules.
Figure 2G:
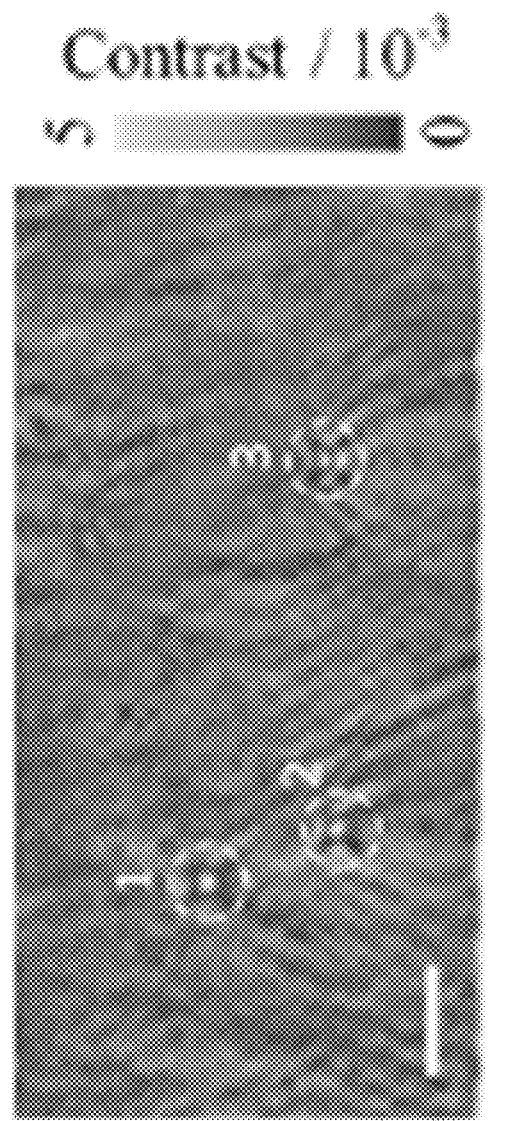
FIG. 2G shows an example of an oscillation amplitude image of BSA molecules obtained at potential of 8 V.
Figure 2G:
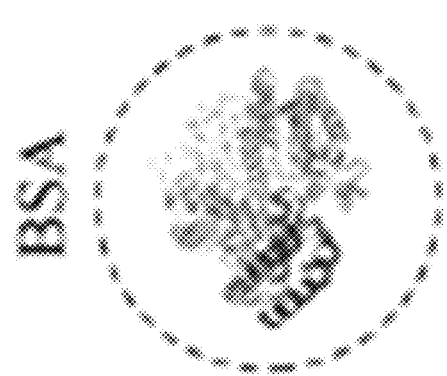

Referring now to FIG. 2E an example of oscillation amplitude vs. applied potential plots of the lysozyme molecules marked in FIG. 2D is shown. Oscillation amplitude vs. applied potential plots of the lysozyme molecules marked in FIG. 2D, where the extracted $D_H$, q, and μ of the molecules are listed in Table 1.

Referring now to FIG. 2F an example of statistical analysis of $D_H$, q, and μ for 246 lysozyme molecules is similarly shown. Small secondary peaks also appear in the diameter and charge histograms of other proteins, which further confirm that the images are primarily due to single molecules. This conclusion is supported by the calibration plot generated using polystyrene nanoparticles of difference sizes (See FIG. 5A and FIG. 5B and details below). In one example, statistical analysis of 246 lysozyme molecules was performed, where the curves are Gaussian fittings to the histograms 210, 212 and 214 (see Table 2 below).

Figure 2H:
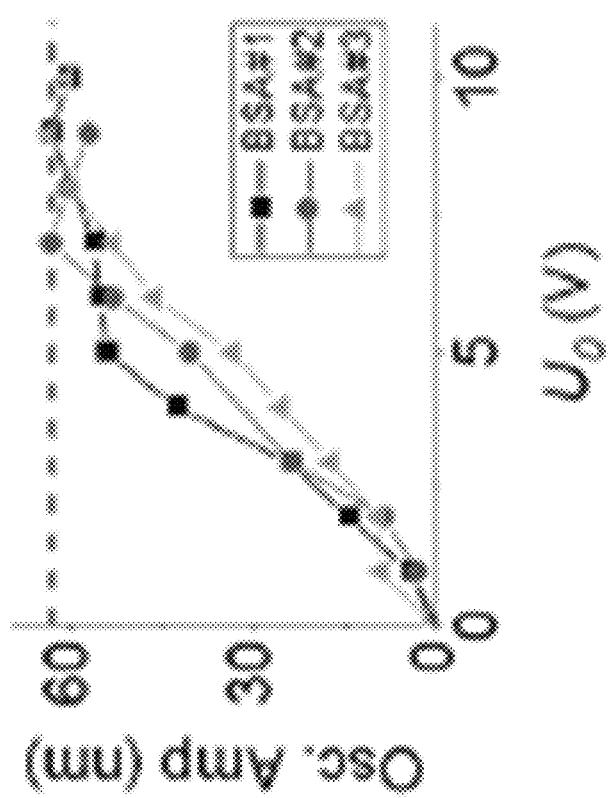
FIG. 2H shows an example of oscillation amplitude vs. applied potential plots of the BSA molecules marked in FIG. 2G.

Referring now jointly to FIG. 2G and FIG. 2H, FIG. 2G shows an example of an oscillation amplitude image of BSA molecules obtained at potential of 8 V and FIG. 2H shows an example of oscillation amplitude vs. applied potential plots of the BSA molecules marked in FIG. 2G, where the extracted $D_H$, q, and p are listed in Table 1.

Figure 2I:
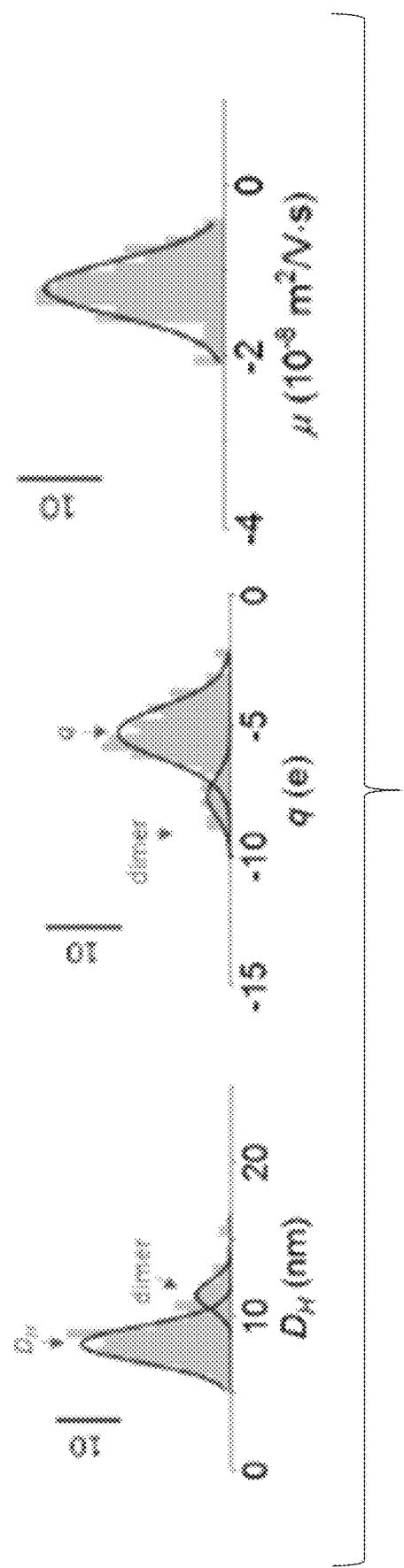
FIG. 2I shows an example of statistical analysis of 144 BSA molecules, where the fitted curves are Gaussian fittings to the histograms.

Referring now to FIG. 2I, an example of statistical analysis of 144 BSA molecules, where the fitted curves are Gaussian fittings to the histograms is similarly shown. In the diameter and charge histograms, small secondary peaks are observed in these proteins, which are due to dimers.

Identifying Single Proteins Via Antibody Binding

Referring now to FIG. 3A an example for identifying single proteins via antibody binding where anti-goat IgG is introduced to bind with PEG tethered goat IgG is shown. To ensure that the individual patterns shown, for single anti-IgG molecules, the inventors studied anti-IgG binding to the IgG tethered on the surface. The inventors first flew PBS buffer over the IgG molecules (oscillating in the plateau regime). After establishing a baseline, the inventors then introduced anti-IgG and monitored its binding to the IgG.

FIG. 3B shows an example for identifying single proteins via antibody binding where binding/unbinding of anti-goat IgG with three goat IgG molecules is tracked in real-time, showing diameter changes associated with the binding and unbinding events. Upon the introduction of anti-IgG, the apparent diameter of IgG increases, indicating binding of anti-IgG to the IgG and formation of an anti-IgG/IgG complex. After measuring the binding process, the inventors flew buffer over the surface and observed diameter decrease in some anti-IgG/IgG binding complexes, indicating unbinding of anti-IgG.

FIG. 3C shows an example of snapshots of the three IgG molecules captured before, during and after the binding experiment in FIG. 3B. The binding and unbinding events are also shown in the oscillation amplitude images captured during the measurement. To confirm the observation, the inventors performed end-point measurement by incubating IgG with 33 nM anti-IgG. The scale bar represents 3 μm.

FIG. 3D shows an example of statistical analysis of 137 goat IgG molecules showing the diameter ($D_H$), charge (q) and mobility (μ) histograms of the molecules after incubation of the molecules with 33 nM anti-goat IgG for ~30 min, the two peaks in the diameter and charge histograms correspond to IgG and anti-IgG/IgG complex. The mobility histogram has one broad peak 302 only because mobility is an intensive quantity and related to the ratio of the charge to the diameter. The peaks 300, 301 and 302 are fitted to Gaussian distribution and the results are shown in Table 2.

The diameter histogram shows two peaks located at 10.3 nm, and 13.2 nm, respectively. The former is IgG, and the later corresponds to IgG/anti-IgG. The charge histogram also reveals two peaks, located at −4.8 e and −7.2 e, which are associated with IgG and IgG/anti-IgG complex. In contrast, the mobility shows only one peak. This is because that mobility is intensive quantity and scales with $q/D_H$. Compared to FIG. 2C, the appearance of the IgG/anti-IgG peak in diameter and charge histograms verifies the binding of anti-goat IgG to goat IgG. The IgG peak indicates some goat IgG molecules remain unbound after incubation, which could be due to the unfavorable orientation of the molecules as tethered by the PEG linker.

Referring now jointly to FIG. 3E and FIG. 3F, FIG. 3E shows an example of a plot derived from a control experiment using anti-human IgG, showing no detectable changes in the diameter of IgG and FIG. 3F shows an example of snapshots of the three IgG molecules captured before, during and after the binding control experiment in FIG. 3E. To further ensure specific binding of anti-IgG to IgG, the inventors performed a control experiment by introducing anti-human IgG and observed no changes in the size and oscillation amplitude image of the goat IgG.

Another example is BSA (MW=66 kDa), which is smaller than IgG but larger than lysozyme. As shown in FIG. 2G, BSA has image contrast lower than IgG but greater than lysozyme, which is consistent with the size of the molecule. The inventors plotted BSA oscillation amplitude vs. potential and observed similar dependence as IgG and lysosome: a low-field increasing regime followed by a high-field plateau regime. The measured $D_H$, q and μ are 8.3 nm, −5.3 e and $-1.2 \times 10^{-8}$ $m^2V^{-1}s^{-1}$ for BSA. These results agree with the values from the dynamic light scattering (as shown in FIG. 5C) and calculated charge (See Table 5). The inventors summarize the results for IgG, lysozyme and BSA, as well as other proteins and complexes in Table 2.

Ligand Binding-Induced Conformation Change in a Protein.

Figure 4A:
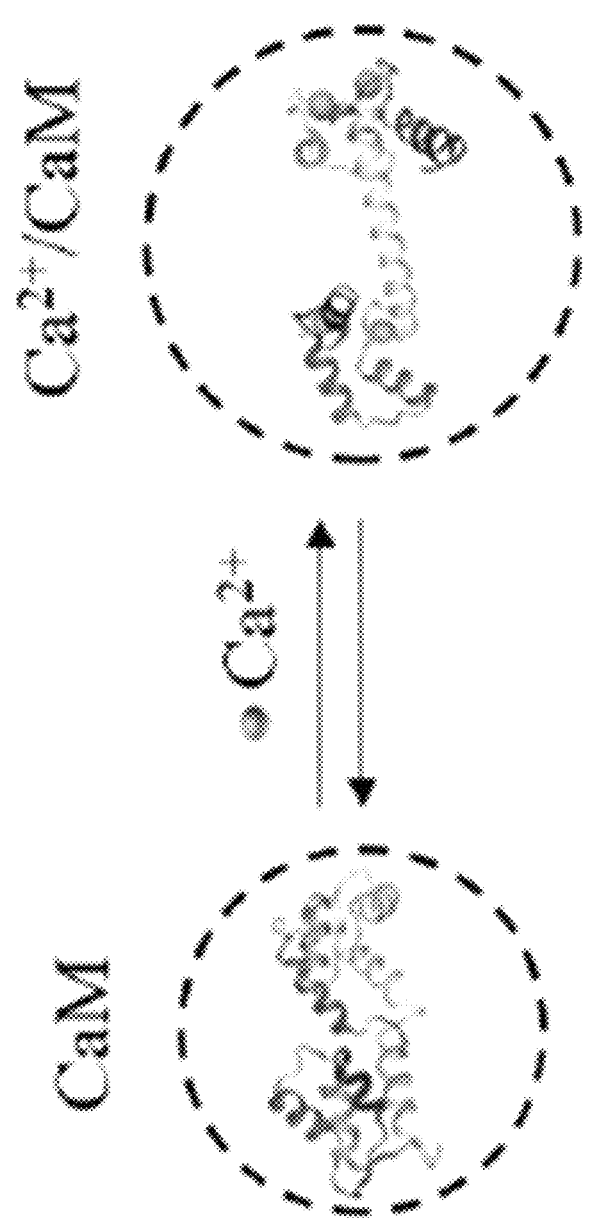
FIG. 4A shows an example of ligand binding-induced conformation change in a protein where binding of Ca2+ to calmodulin (CaM) causes conformation and charge changes in CaM.

Referring now to FIG. 4A, an example of ligand binding-induced conformation change in a protein where binding of Ca2+ to calmodulin (CaM) causes conformation and charge changes in CaM is shown. In addition to quantifying the size, charge and mobility of single proteins, the present imaging technology can measure conformation changes in proteins. To demonstrate this capability, the inventors studied $Ca^{2+}$ binding to calmodulin (CaM), a protein that mediates various important $Ca^{2+}$ signaling processes, such as muscle contraction, inflammation and fertilization.[21] CaM has two globular domains, each containing two EF-hand motifs, so it can bind up to four $Ca^{2+}$ and causes a conformal change in CaM.[22]

Figure 4B:
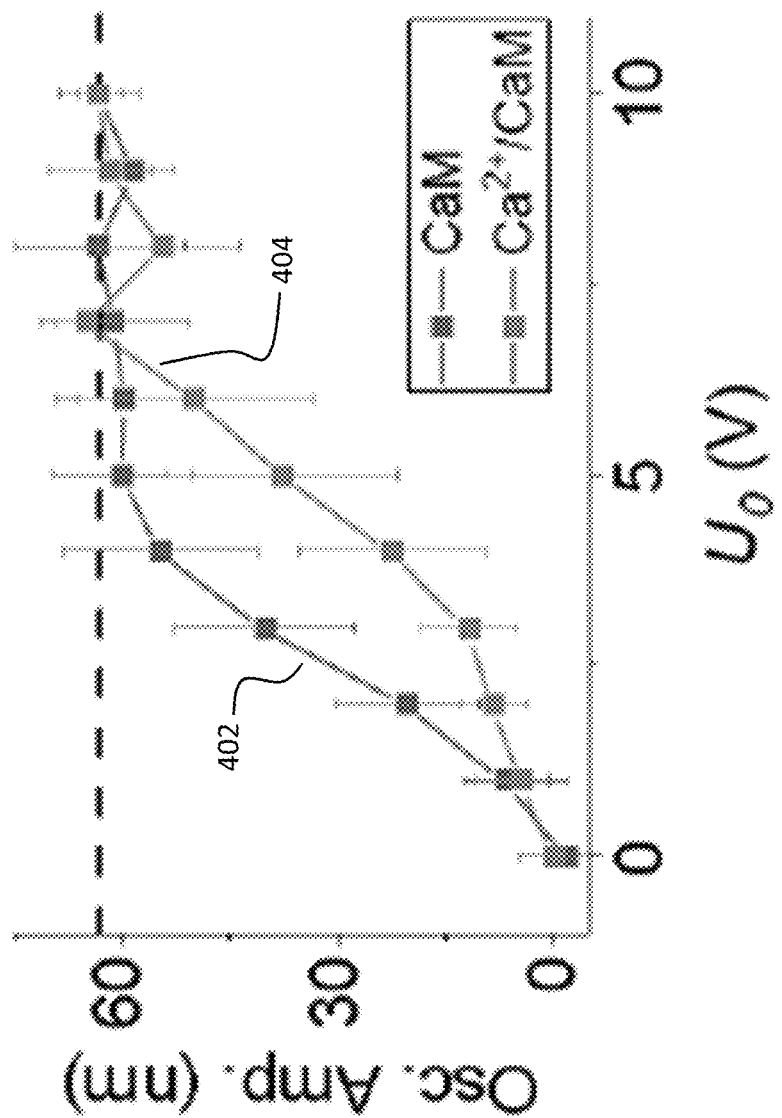
FIG. 4B shows an example of a plot representing oscillation amplitude vs. potential plots before and after Ca2+ binding to CaM.
Figure 4C:
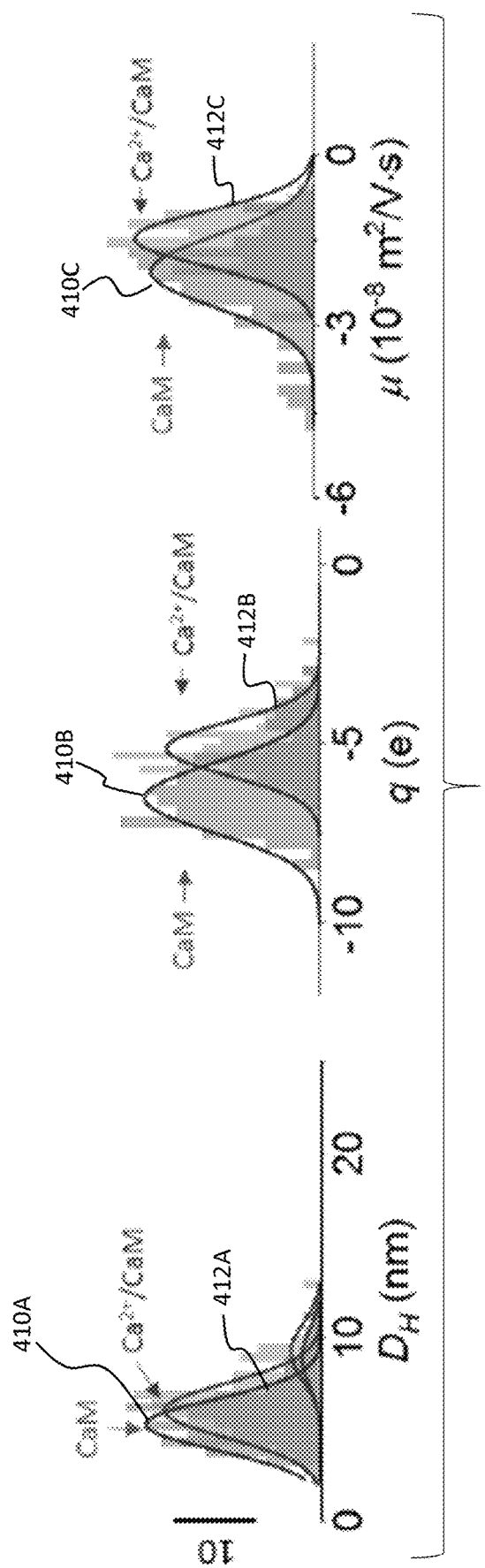
FIG. 4C shows an example a statistical analysis for 150 CaM molecules and 151 Ca2+/CaM molecules showing the diameter ($D_H$), charge (q) and mobility (μ) distributions of CaM and Ca2+/CaM complex.

Referring now to FIG. 4B, an example of a plot representing oscillation amplitude vs. potential plots before 402 and after 404 Ca2+ binding to CaM is shown. The inventors tethered CaM to an ITO surface, incubated it in buffers with and without $Ca^{2+}$, and measured the oscillation vs. potential in each buffer, from which the inventors determined $D_H$, q and μ for CaM and $Ca^{2+}$/CaM complex. A total number of 150 CaM molecules and 151 $Ca^{2+}$/CaM complexes were measured and the histograms are shown in FIG. 4C. $D_H$ of CaM increases from 5.3 nm to 6.0 nm upon binding to $Ca^{2+}$. This finding is also consistent with literature values,[22] which is attributed to $Ca^{2+}$ binding-induced conformation change in CaM. The error bar represents measurement of >150 individual CaM or Ca2+/CaM molecules.

The inventors verified this size increase by performing dynamic light scattering (As shown in FIG. 5C). q for CaM is −6.5 e and changes to −5.1 e upon binding to $Ca^{2+}$. μ for CaM is found to be $-2.0 \times 10^{-8}$ $m^2V^{-1}s^{-1}$, which changes to $-1.4 \times 10^{-8}$ $m^2V^{-1}s^{-1}$ after binding to $Ca^{2+}$.

Referring to FIG. 4C, an example of statistical analysis histograms for 150 CaM molecules and 151 Ca2+/CaM molecules showing the diameter ($D_H$), charge (q) and mobility (μ) distributions of CaM and Ca2+/CaM complex is shown. Similarly to the histograms above, the peaks are fitted using a Gaussian curve fitting method for 150 CaM molecules 410A, 410B, 410C and 151 Ca2+/CaM molecules 412A, 412B, 412C showing the diameter ($D_H$), charge (q) and mobility (μ) distributions of CaM and Ca2+/CaM complex respectively (see Table 2 for the summary).

Figure 4D:
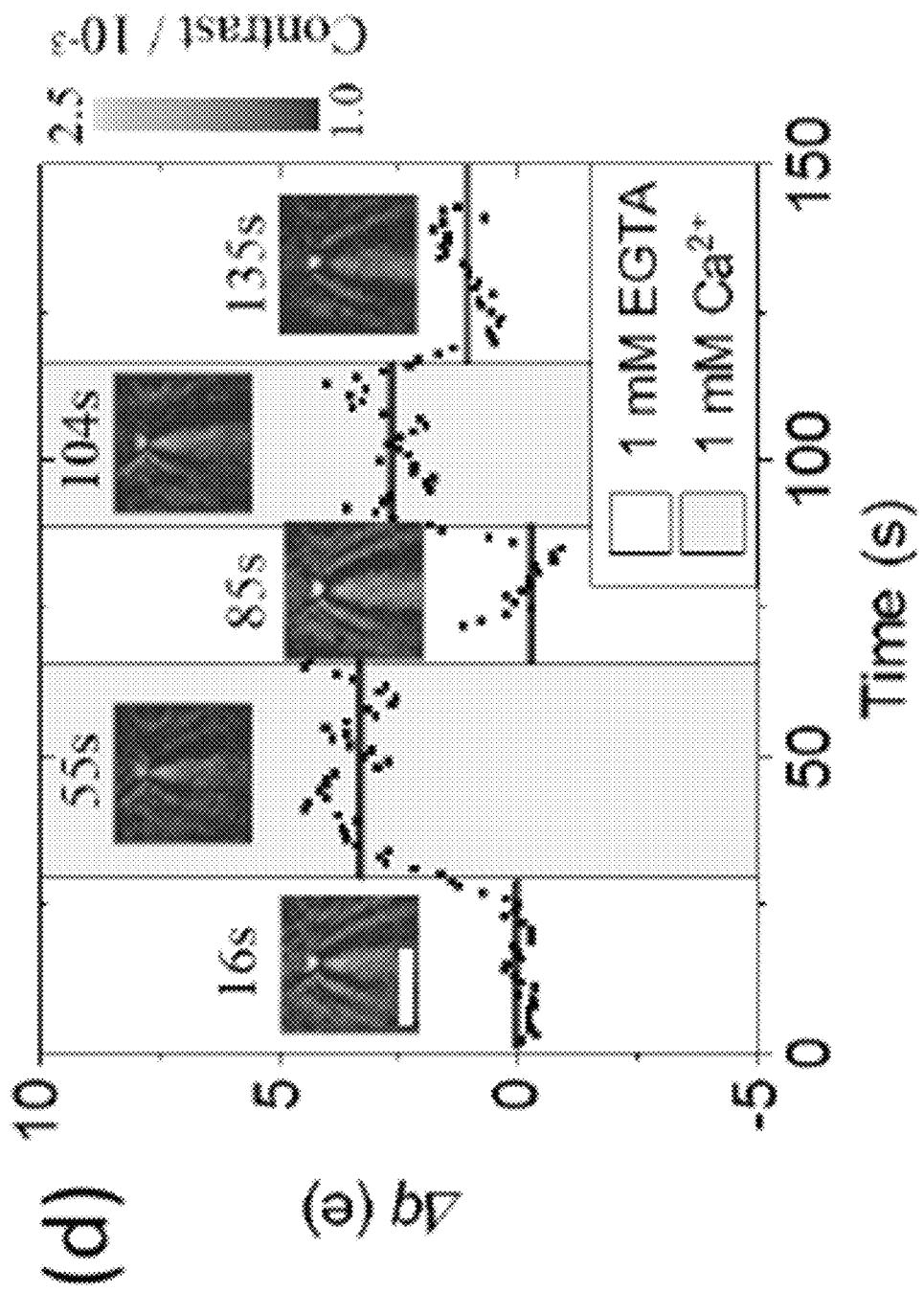
FIG. 4D and FIG. 4E shows an example of tracking of the charge (Δq) and size ($ΔD_H$) changes of a single CaM molecule induced by Ca2+ binding over time.
Figure 4E:
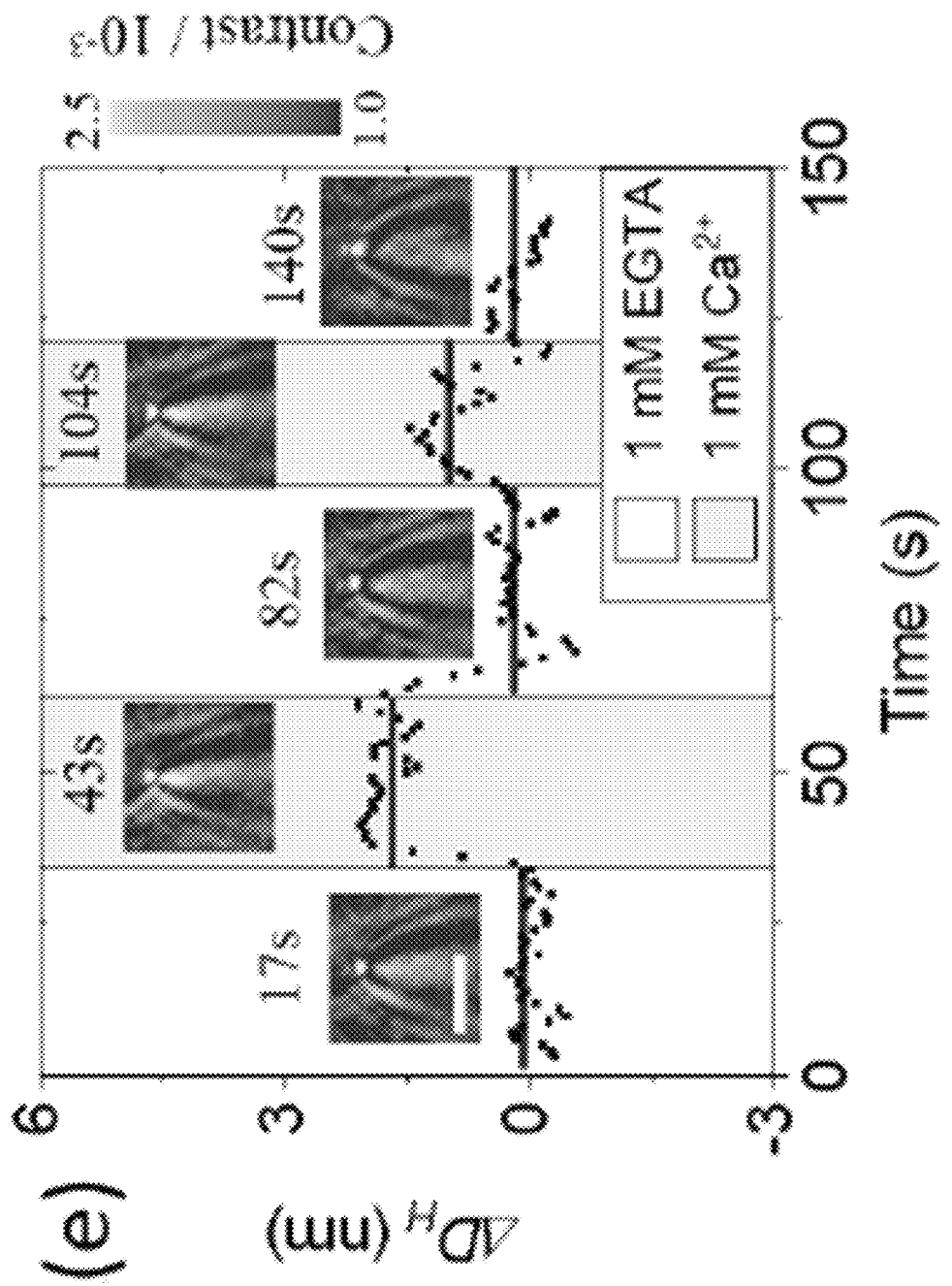

Referring jointly to FIG. 4D and FIG. 4E, an example of tracking of the charge (Δq) and size ($\Delta D_H$) changes of a single CaM molecule induced by Ca2+ binding over time is shown. In this example the potential is fixed at 4 V for the charge measurement, and at 7 V for the size measurement. For both charge and size measurements, the solution flowing over the surface is alternated between EGTA and PBS (at pH=7.4). The scatter plot (black dots) are raw data smoothed over 3 points, and the straight fitted lines are guide to the eye, showing the charge or size change in each cycle. The inset images are snapshots of a CaM molecule captured during Ca2+ binding. The scale bars in the images represent 3 μm.

The inventors also monitored Ca2+ binding to CaM in real time by first driving CaM into oscillation to the maximum (plateau regime), and then alternatively flowing 1 mM Ca2+ and 1 mM ethylene glycol tetraacetic acid (EGTA) solutions over the surface. EGTA is known to cause unbinding of Ca2+ from CaM via chelation with Ca2+, so the experiment allowed us to repeatedly monitor the binding and unbinding processes between Ca2+ and a CaM molecule. From the oscillation amplitude images acquired in real time, the inventors obtained both the effective size and charge changes of single CaM molecules. The real-time data are consistent with the above equilibrium measurements carried out by incubating CaM in Ca2+ and Ca2+ free solutions. CaM is found to be −2.0×10−8 m2V−1s−1, which changes to −1.4×10−8 m2V−1s−1 after binding to Ca2+.

Identifying Proteins Based on Size and Mobility

Referring now to FIG. 5A, an example of a plot representing image contrast vs. size for polystyrene (PS) particles is shown. Because PS particles bind to the ITO surface from the bulk solution ($\Delta z_0 \rightarrow \infty$), the image contrast is $C(0, D_H)$ according to Eq. 2. The inventors performed calibration by imaging polystyrene nanoparticles of different diameters ($D_H$=40-140 nm). These nanoparticles are larger than the proteins and can be directly imaged with the setup by subtracting the background from each image, allowing us to obtain the image contrasts vs. size.

Figure 9A:
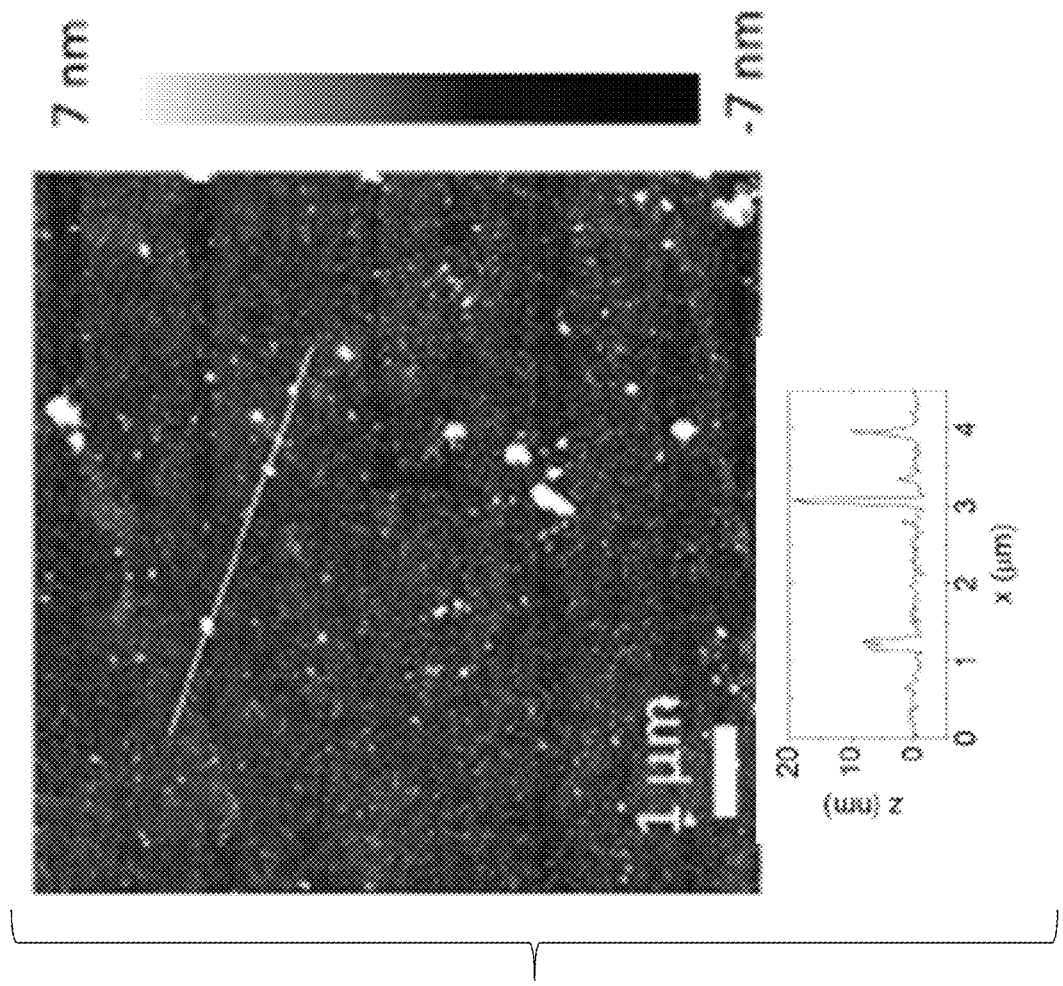
FIG. 9A shows an example of surface roughness effect in a typical AFM image of the ITO surface, showing grains with 0-20 nm in diameter.

Referring now to FIG. 5B, an example of a plot for determining protein size ($D_H$, app) from image contrast change, $\Delta C(L_{PEG}, D_H)$ is shown. Unlike the PS particles, the proteins are tethered to the surface with a maximum distance of $L_{PEG}$. The inventors thus measured a tethered 15-nm PS particle and included the data in the plot (see examples below for details). Since the single protein measurements used a PEG linker, the inventors evaluated the effect of the linker on the calibration plot by attaching 15-nm polystyrene nanoparticles to the ITO surface and carried out the same measurements as for the proteins. The power relation between the image contrast and $D_H$ is ~2.2, smaller than the value of 3 for a simple scattering model. This discrepancy is due to the roughness of the ITO surface as confirmed by AFM and simulation (as shown in FIG. 9A). The protein sizes determined with the calibration curve are close to those in literature, which validates the calibration.

Referring now to FIG. 5C, an example of a plot representing comparison of measured $D_H$ and µ with light scattering experiments and also literature values is shown. The inventors further compared our results with dynamic light scattering and electrophoretic light scattering measurements. The hydrodynamic diameters measured here for single proteins are in good agreement with the dynamic light scattering values and within the range reported in literature (Table 3 and 4). The single molecule mobility also agrees with those by electrophoretic light scattering for all the cases.

Figure 5D:
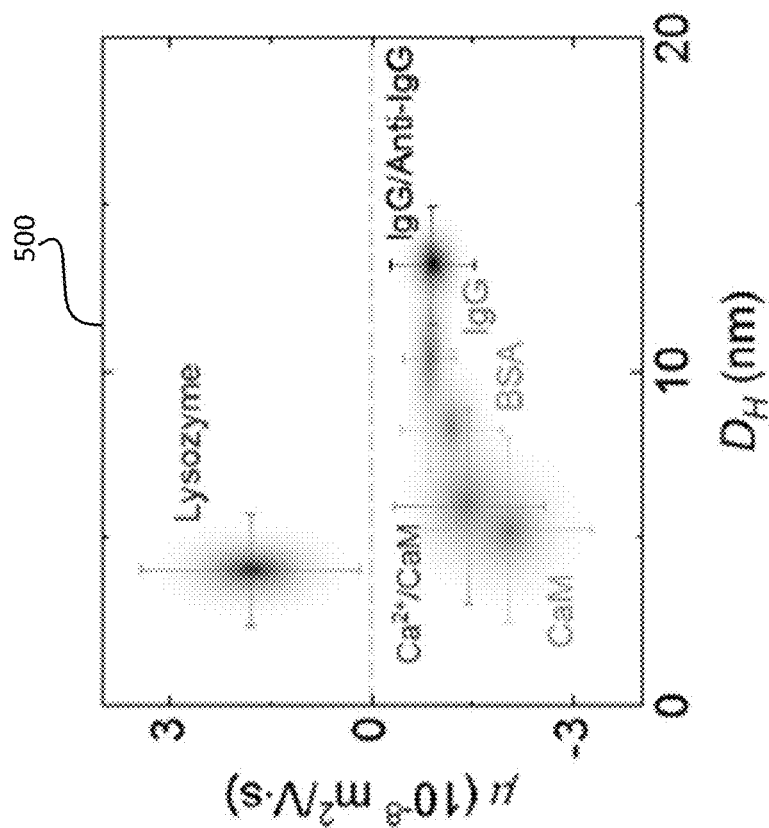
FIG. 5D shows an example of a plot showing mobility (μ)-size ($D_H$) of single proteins and protein-ligand complexes.
Figure 5C:
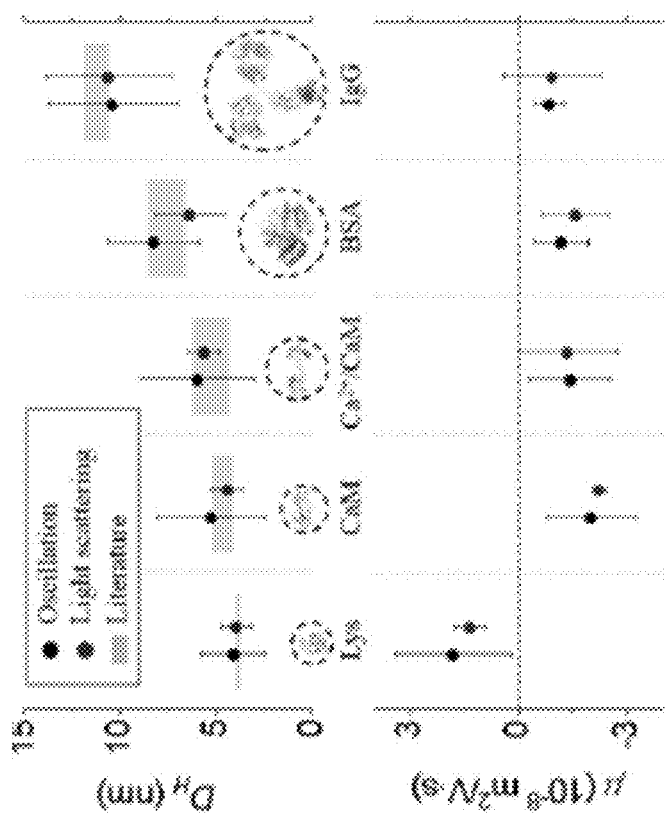
FIG. 5C shows an example of a plot representing comparison of measured $D_H$ and μ with light scattering experiments and also literature values.

Referring now to FIG. 5D, an example of a plot showing mobility (µ)-size ($D_H$) of single proteins and protein-ligand complexes is shown. Two-dimensional (2D) gel electrophoresis is a powerful technology that identifies proteins based on their size and µ (or mobility at different pH). The present single molecule imaging method can perform protein analysis in an analogous manner, but at the single molecule level and without the time-consuming separation step. This capability is shown in plot 500 which plots different proteins and protein-ligand complexes according to mobility and size. The proteins and complexes in the 2D-plot are separated, allowing identification of proteins like 2D electrophoresis. Binding of IgG to anti-IgG shifts the IgG region to a new position in the 2D-plot (FIG. 5D). This is similar to the Western Blot and provides additional identification of the protein.

Methods
Materials.

ITO slides with resistance of 70-100Ω were purchased from SPI Supplies. Streptavidin was purchased from VWR. (3-Glycidyloxypropyl)trimethoxylilane, lysozyme, calmodulin, and BSA were purchased from Sigma-Aldrich. Goat IgG (anti-digoxigenin) was purchased from Abcam. Goat anti-human IgG and rabbit anti-goat IgG were purchased from Invitrogen. Polystyrene nanoparticles were purchased from Bangs Labs. Biotin-PEG-NHS (MW=10 kDa) and streptavidin coated polystyrene particles were purchased from Nanocs. Deionized (DI) water with resistivity of 18.2 MΩ·cm was used in all the experiments.

Experimental Setup

The imaging setup was built on an inverted microscope (Olympus IX-81) with a 60× (NA=1.49) oil immersion objective. A superluminescent light emitting diode (SLED) (SLD-260-HP-TOW-PD-670, Superlum) with central wavelength at 670 nm and output power of up to 15 mW was used as light source. A CMOS camera (ORCA-Flash 4.0, Hamamatsu) was used to record 2048 by 256 pixels images at 800 frames per second. A sinusoidal potential (f=80 Hz) was applied to the ITO slide with a function generator (33521A, Agilent) and a potentiostat (AFCBP1, Pine Instrument Company) using a three-electrode configuration, where the ITO, a Ag wire and Pt coil served as the working, reference and counter electrodes, respectively. A USB data acquisition card (NI USB-6251, National Instruments) was used to synchronize the applied potential, the current, and the recorded images.

Modification of ITO Surface

The ITO slides were cleaned by sonication sequentially in acetone, ethanol, and DI water, each with 20 min, and then soaked in H2O2/NH3.H2O/H2O (1:3:5) for one hour, which were then rinsed with DI water and dried with N2. The slides were incubated in 1% (3-Glycidyloxypropyl)trimethoxylilane in isopropanol for 10 hours to silanize and form terminal epoxy groups. The epoxy-functionalized slides were rinsed with isopropanol and DI water, dried with N2, and incubated in 0.1 mg/ml streptavidin +1×PBS for 4 hours. At last, the slides were incubated in 0.1 mg/ml BSA+1×PBS for 30 minutes.

Assembly of Protein Oscillators

Biotin-PEG-NHS was used to tether the protein to the functionalized ITO surface. The protein (IgG, BSA, lysozyme, or CaM) was first incubated with the biotin-PEG-NHS linker at 10:1 ratio to form a PEG-protein complex in 1×PBS overnight at 4° C. The solution containing protein-PEG complex was then added to the streptavidin coated ITO slides and incubated for one hour to allow biotin-streptavidin binding. Finally, the chip was gently washed with 100 times diluted PBS to remove free protein molecules in the solution.

Calibration Curve

100× diluted PBS was placed on top of the ITO slide, and PS nanoparticle solution was added to allow binding of the nanoparticles to the slide surface. An image sequence was recorded at 800 frames per second for 5 seconds. The hydrodynamic diameter of each PS nanoparticle sample was measured with dynamic light scattering.

Signal Processing

An FFT filter was applied to the recorded image sequence. A region of interest (ROI) with 10×10 pixels was selected for each protein, and the mean intensity within the ROI ($I_p$) was used to determine the contrast of the protein. An adjacent region of the same size was selected as a reference region, and the mean intensity of the reference region ($I_r$) was also determined. The contrast of the protein was determined with $\Delta C(\Delta z_0, D_H)=(I_p-I_r)/I$, where I is the mean intensity within the ROI without FFT filter. The size and charge of each protein were determined based on the contrast.

TABLE 2

Measured size ($D_H$), charge (q), and mobility (µ) of protein molecules and ligandprotein complexes.

| | Molecules studied | $D_H$ (nm) | q (e) | µ ($10^{-8}$ m²/V · s) |
|---|---|---|---|---|
| IgG | 186 | 10.4 ± 3.4 | −5.0 ± 1.2 | −0.86 ± 0.39 |
| BSA | 144 | 8.3 ± 2.4 | −5.3 ± 2.0 | −1.2 ± 0.75 |
| Lysozyme | 246 | 4.1 ± 1.7 | 4.3 ± 1.2 | 1.8 ± 1.6 |
| CaM | 150 | 5.3 ± 2.8 | −6.5 ± 1.9 | −2.0 ± 1.2 |
| Ca²⁺/CaM | 151 | 6.0 ± 2.9 | −5.1 ± 1.7 | −1.4 ± 1.1 |
| Anti-IgG/IgG | 137 | 13.2 ± 1.8 | −7.2 ± 2.0 | −0.90 ± 0.62 |

Examples: Entropy of PEG Linker and Oscillation of Tethered Protein Molecules

The oscillation of a protein molecule tethered by a PEG linker can be described by, $$m\frac{d^2z}{dt^2} + c\frac{dz}{dt} + k_{PEG}z = qE, \quad (3)$$

where m, z, c, $k_{PEG}$, q, and E are mass, displacement of the protein molecule, damping coefficient, entropic spring constant of PEG linker, charge of the protein, and electric field, respectively. For a protein molecule with molecular weight of 100 kDa (m=1.7×10⁻¹⁹ g) oscillating at 80 Hz, the first term and the second term are about $10^{-13}$ pN and $10^{-3}$ pN, respectively, much smaller than the entropic force (see below).

The inventors use the freely jointed chain (FJC) model[23, 24] to calculate the entropic force of the PEG, $$f_{entropy} = k_{PEG}z = \frac{3k_BT}{nb^2}z, \quad (4)$$

where kB is the Boltzmann constant, T is temperature, b is the Kuhn length of PEG, n is the number of segments with length of b, and z is the distance between the tethered protein molecule and surface. For PEG10k, b=0.55 nm, n=113,[25] and $k_{PEG}$=3.62×10$^{-4}$ N/m. The entropic force is 22.8 pN when the PEG is stretched (z~63 nm). Thus, by ignoring the first term and the second term, Eq. 3 becomes, $$k_{PEG}z = qE, \quad (5)$$

Because the modulation is sinusoidal, $z = \Delta z_o e^{i\omega t}$ and $E = E_o e^{i\omega t}$, where the angular frequency $\omega = 2\pi/f$. Also, the electric field applied to the molecule is a function of applied potential amplitude $U_0$ and molecule-surface distance $\Delta z_0$, $E = E_0(\Delta z_0, U_o)e^{i\omega t}$. By combining the above relations with Eq. 5, the inventors obtain the oscillation equation of the protein molecule (Eq. 1).

Measuring of Electric Field Near the Surface

Figure 6A:
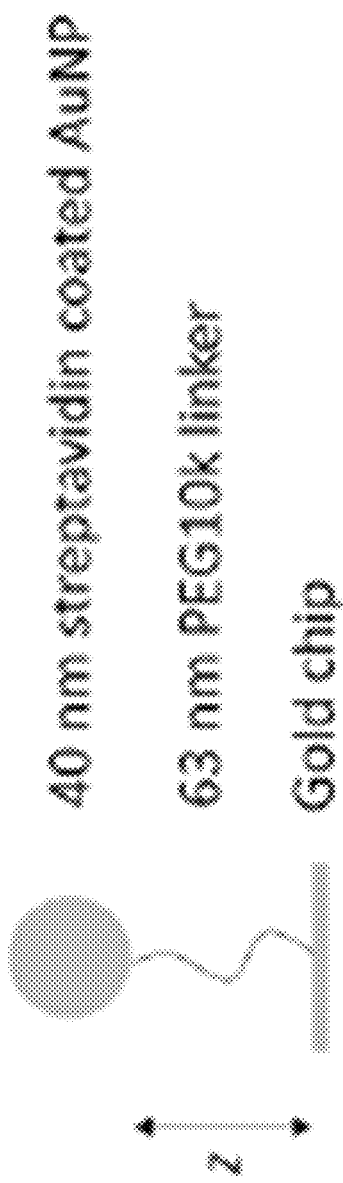
FIG. 6A schematically shows an example of measuring electric field near the surface using tethered gold nanoparticles (AuNPs).
Figure 6B:
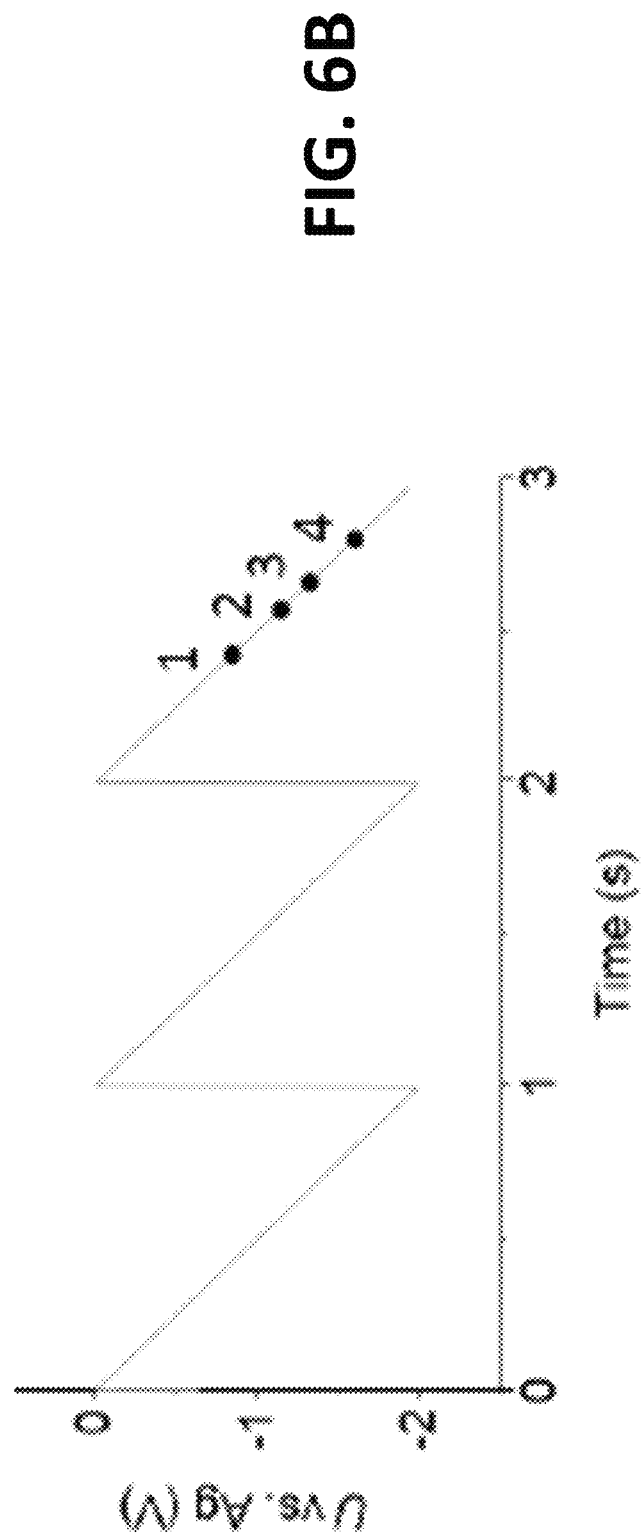
FIG. 6B shows an example of a plot where a triangular potential sweep is applied to the gold surface to drive the AuNP.

Referring now jointly to FIG. 6A and FIG. 6B, FIG. 6A schematically shows an example of measuring electric field near the surface using tethered gold nanoparticles (AuNPs) and FIG. 6B shows an example of a plot where a triangular potential sweep is applied to the gold surface to drive the AuNP. According to Eq. 1 and FIG. 1F, the charge of the molecule can be obtained once the electric field ($E_0$C$\Delta z_0$=$L_{PEG}$, $U_0$=$U_{trans}$) at the transition point ($\Delta z_0$=$L_{PEG}$) is determined. To measure the electric field, the inventors tethered 40 nm streptavidin coated gold nanoparticles (AuNPs) to a gold film with PEG10k linkers,[26] pulled the AuNPs away from the surface by applying potential, and recorded particle-surface distance (z) change with the potential.

Figure 6C:
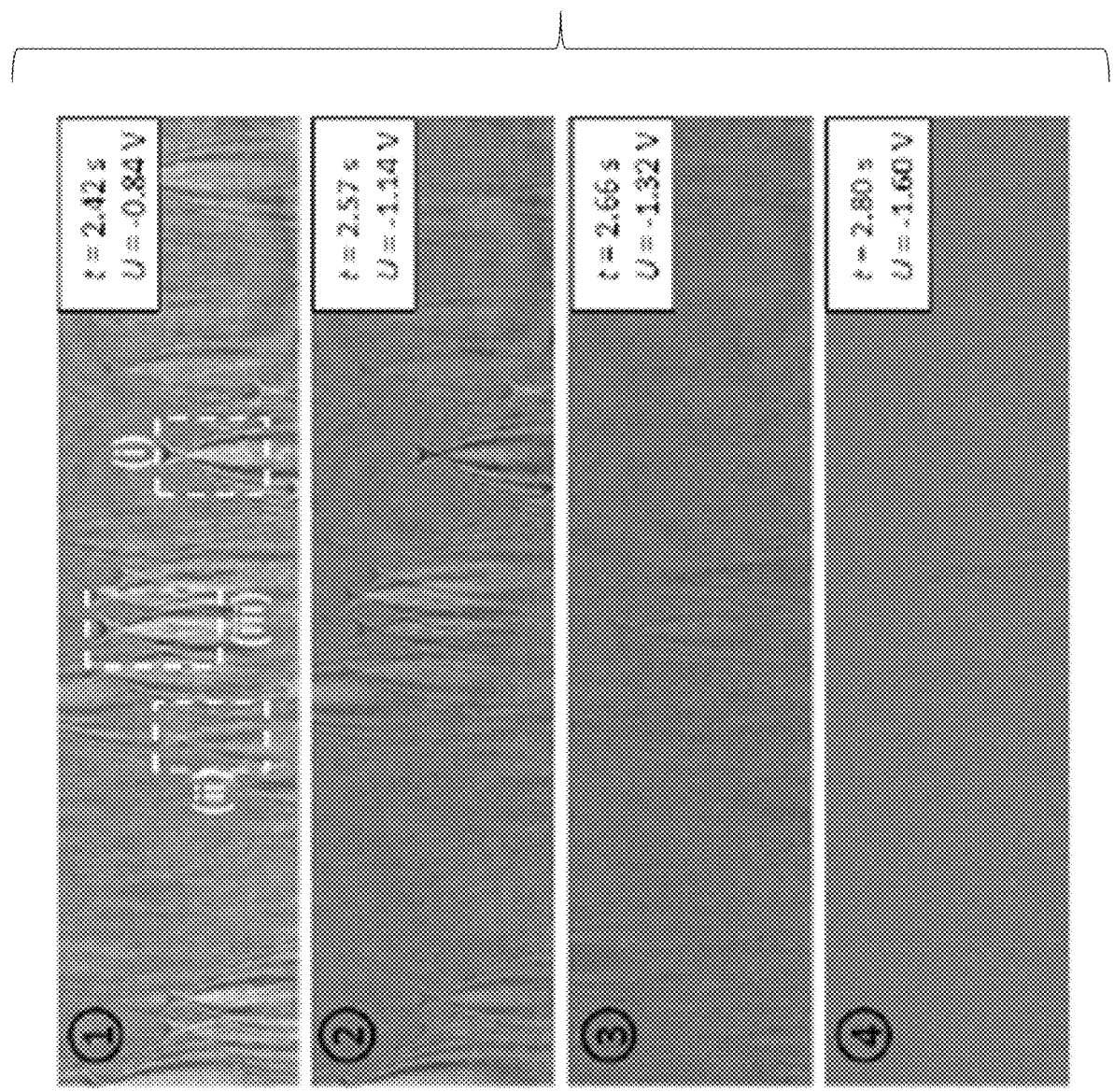
FIG. 6C shows an example of snapshots of particles at different potentials (marked in FIG. 6B).

Referring now to FIG. 6C, an example of snapshots of particles at different potentials (marked in FIG. 6B as 1,2,3,4) is shown. The intensity change reflects the change in particle-surface distance. Because AuNPs are negatively charged at pH=7.4, the negative potential pulls the particles away from the surface, leading to decrease in image intensity.

Referring now to FIG. 6D, examples of plots representing intensity change in each cycle fitted to exponential decay is shown. Intensity response of three particles marked in FIG. 6C is plotted as raw data 602A, 602B, 602C to applied potential 600. The intensity change in each cycle is fitted to exponential decay shown as fitted curves 604A, 604B, 604C. The intensity decreases exponentially with the potential and reaches the minimum value when the PEG is fully stretched.

Figure 6E:
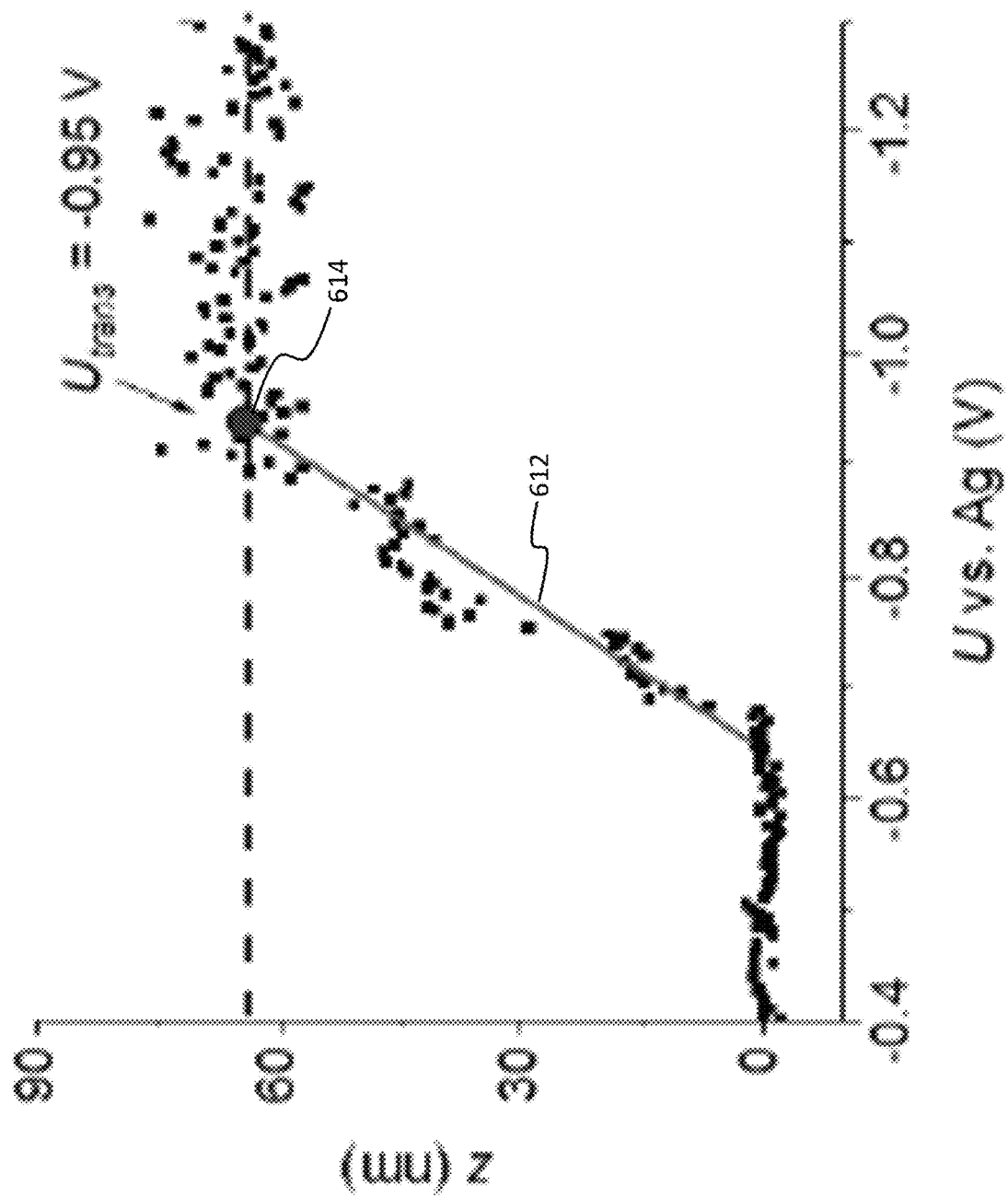
FIG. 6E shows an example of a plot where intensity change of particle (marked in FIG. 6D) is converted to particle-surface distance (z).

Referring now to FIG. 6E, an example of a plot where intensity change of particle (marked in FIG. 6D) is converted to particle-surface distance (z) is shown. By converting the image intensity into particle-surface distance (z),[4] the inventors obtained $\Delta z_0$ vs. $U_0$ plot for the AuNP (FIG. 6E). The plot shows a linear regime followed by a plateau regime, which is consistent with the observation for protein molecules. After the particle is pulled off the surface, the distance shows linear relationship with the applied potential and finally reaches the plateau where the PEG is fully stretched. The line 612 is the fitting of the linear regime, and the dot 614 marks the transition point, where the entropic force reaches a plateau, and the corresponding applied potential is $U_{trans}$=−0.95 V.

To determine the field at a given potential, the inventors calculated the charge of the AuNPs based on the zeta potential, given by,[27,28]

$$q_{NP} = 4\pi a^2 \cdot \frac{2\varepsilon_r \varepsilon_0 \kappa k_B T}{z} \sinh\left(\frac{ze\zeta}{2k_BT}\right)\left[1 + \frac{1}{\kappa a \cdot \cosh^2(Ze\zeta/4k_BT)}\right], \quad (6)$$

where a is the radius of the particle, Z is the valence of ions in the electrolyte solution, $e_o$ and $e_r$ are the permittivity of vacuum and the relative permittivity of the solution, $k^{-1}$ is the Debye length, e is the elementary electric charge, and $\zeta$ is zeta potential of the particle. The inventors found that $k^{-1}$=7.89 nm (see "charge screening effect" section) and $\zeta$=−13.1 mV, which was measured by ELS. Thus, the inventors obtained qNP with Eq. 6, which was −42.5 e. The entropic force of the stretched PEG linker is 22.8 pN, which is balanced by the electrostatic force according to qNPE$_0$C$\Delta z_0$=$L_{PEG}$, $U_0$=$U_{trans}$)=$k_{PEG}L_{PEG}$, from which the inventors have $E_0$=−3.35×10$^6$ V/m. Because the electric field at a given distance from the surface ($\Delta z_0$=$L_{PEG}$) scales with applied potential $U_0$, the inventors obtain the following relation, $$E_0(\Delta z_0 = L_{PEG}) = 3.53 \times 10^6 U_0/m. \quad (7)$$

Using this equation and the transition potential (Utrans) obtained with the oscillation amplitude vs. potential plot (FIG. 1F), the electric field at the transition point was determined.

Determination of Protein Size and Mobility

By changing the applied electric field and performing FFT, the oscillation amplitude images of the proteins are obtained at different electric fields. This allows us to plot the image contrast, $\Delta C(\Delta z_0, D_H)$ vs. the applied potential amplitude ($U_0$). From the plateau regime of the plot, corresponding to a stretched PEG linker, the inventors determined the image contrast in the plateau regime, $\Delta C(L_{PEG}, D_H)$, which is used to determine the image contrast at z=0, C(0, $D_H$), using Eq. 2. The apparent diameter of the protein, including the contributions of the protein and the PEG linker, is obtained using the calibration curve (FIG. 5A-FIG. 5D). Knowing the length of PEG, the inventors extracted the protein diameter ($D_H$) with Eq. 8.

To determine the charge, $\Delta C(\Delta z_0, D_H)$ vs. $U_0$ plot is first converted into $\Delta z_0$ vs. $U_0$ plot, where $\Delta z_0$ is obtained using Eq. 2, according to, $$\frac{1 - \exp\left(-\frac{\Delta z_0}{d}\right)}{1 - \exp\left(-\frac{L_{PEG}}{d}\right)} = \frac{\Delta C(\Delta z_0, D_H)}{\Delta C(L_{PEG}, D_H)}. \quad (8)$$

The transition point of the $\Delta z_0$ vs. $U_0$ plot is determined from the intersection between linear regime and the plateau regimes.

Effect of PEG Linkers

The size obtained from the oscillation image contrast include contributions from the linker. To extract the diameter of the protein ($D_H$), the following equation is used, $$D_H^3 = D_{H,app}^3 - D_{H,PEG}^3, \quad (9)$$

where $D_H$,app is the apparent diameter of the protein, and $D_{H,PEG}$ is the diameter of PEG coil measured with DLS.

The Length of the PEG Linker

The PEG monomer has a length of 0.278 nm,[7,8] and the PEG linker used in this work has a molecular weight of 10 kDa, consisting of 225 ethylene glycol units. The linear length of the PEG is: 0.278 nm×225=63 nm.

Extracting Oscillation Amplitude by Performing FFT

Figure 7B:
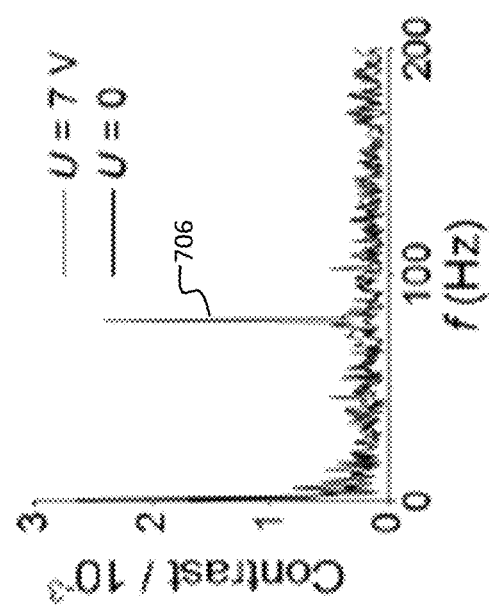
FIG. 7B shows an example of a FFT of the oscillation in FIG. 7A.
Figure 7C:
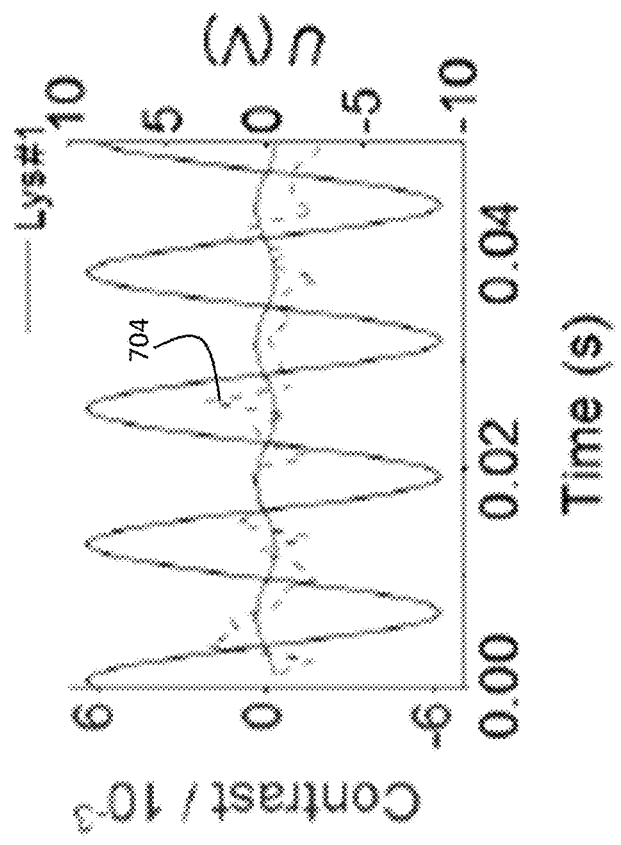
FIG. 7C shows an example of oscillation of a lysozyme (Lys) molecule with potential (U).
Figure 7D:
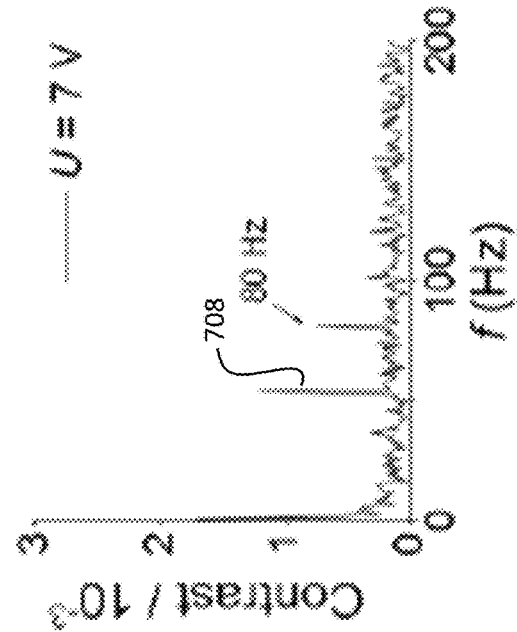
FIG. 7D shows an example of a FFT of the oscillation of the lysozyme molecule in FIG. 7C over one second shows a pronounced peak at 80 Hz.

Referring now concurrently to FIG. 7A-FIG. 7D, FIG. 7A shows an example of oscillation of an IgG molecule with potential (U), FIG. 7B shows an example of a FFT of the oscillation in FIG. 7A, FIG. 7C shows an example of oscillation of a lysozyme (Lys) molecule with potential (U) and FIG. 7D shows an example of a FFT of the oscillation of the lysozyme molecule in FIG. 7C over one second shows a pronounced peak at 80 Hz. Buffer: 100 times diluted PBS, pH=7.4. The images captured by the CMOS imager record the oscillation of protein molecules over time. Plotting the local image contrast vs. time reveals periodic oscillation of an IgG molecule shown as dashed lines 702, 704 in FIG. 7A and FIG. 7C respectively. The FFT amplitude spectrum shows a sharp peak located at the frequency of the applied electric shown as lines 706, 708 in FIG. 7B and FIG. 7D respectively. The inventors performed this FFT analysis on each pixel of the time sequence images as shown in FIG. 1C, extracted the oscillation amplitude averaged over one second, and constructed an FFT image (oscillation amplitude image) shown in FIG. 1D.

Additional Examples Showing Charge Change

Figure 8A:
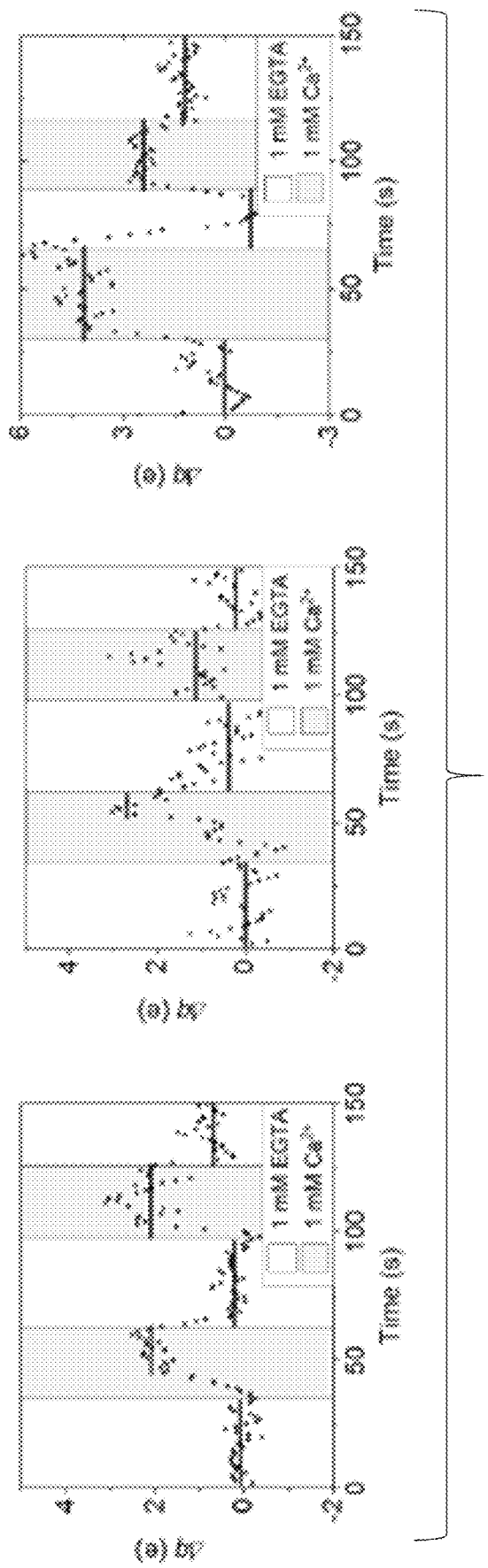
FIG. 8A shows an additional example of plots representing charge change during CaM-$Ca^{2+}$ interaction.
Figure 8B:
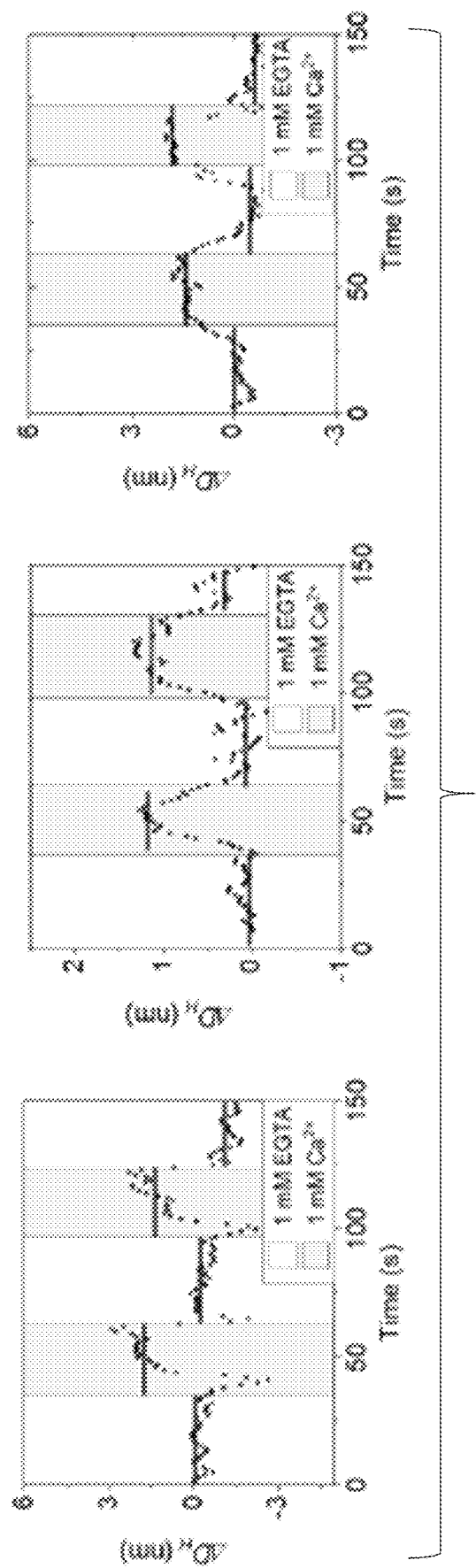
FIG. 8B shows an additional example of and size change during CaM-$Ca^{2+}$ interaction.

Referring now to FIG. 8A, an additional example of plots representing charge change during CaM-$Ca^{2+}$ interaction and also referring now to FIG. 8B, an additional example of and size change during CaM-$Ca^{2+}$ interaction are shown. For both charge and size measurements, the solution cycles between 1 mM EGTA in 100 times diluted PBS and 1 mM CaCl2 in 100 times diluted PBS at pH=7.4. The black points are raw data smoothed by 3 points, and the fitted straight lines are guides to the eye showing the charge or size change in each cycle.

Imaging Principle

Light is directed on the ITO surface at an angle close to the critical angle to generate an evanescent wave ($\mu_e$) propagating along the surface. When a protein is present on the surface, it scatters the evanescent wave, generating a scattered wave ($\mu_s$), given by $$u_s(r,r')=\alpha u_e(r')e^{-\kappa|r-r'|}e^{-ik|r-r'|} \quad (10)$$

where r' is the location of the protein, α is a scattering coefficient related to the polarizability of the molecule, α is the decaying constant of the evanescent wave, and k is the wavenumber of evanescent wave. The superposition of the two waves, together with light reflected from the ITO surface ($u_r$), is $$u(r,r')=u_r(r)+u_e(r)+u_s(r,r'). \quad (11)$$

The overall reflected light detected by the camera (I) is given by, 9-13

$$I=|u_r(r)+u_e(r)+u_s(r,r')|^2. \quad (12)$$

The image contrast of the particle is described by $$I(r,r')=|u_r(r)+u_e(r)+u_s(r,r')|^2-|u_r(r)+u_e(r)|^2, \quad (13)$$

where the last term is the background image in the absence of the protein, which is subtracted out.

Figure 9B:
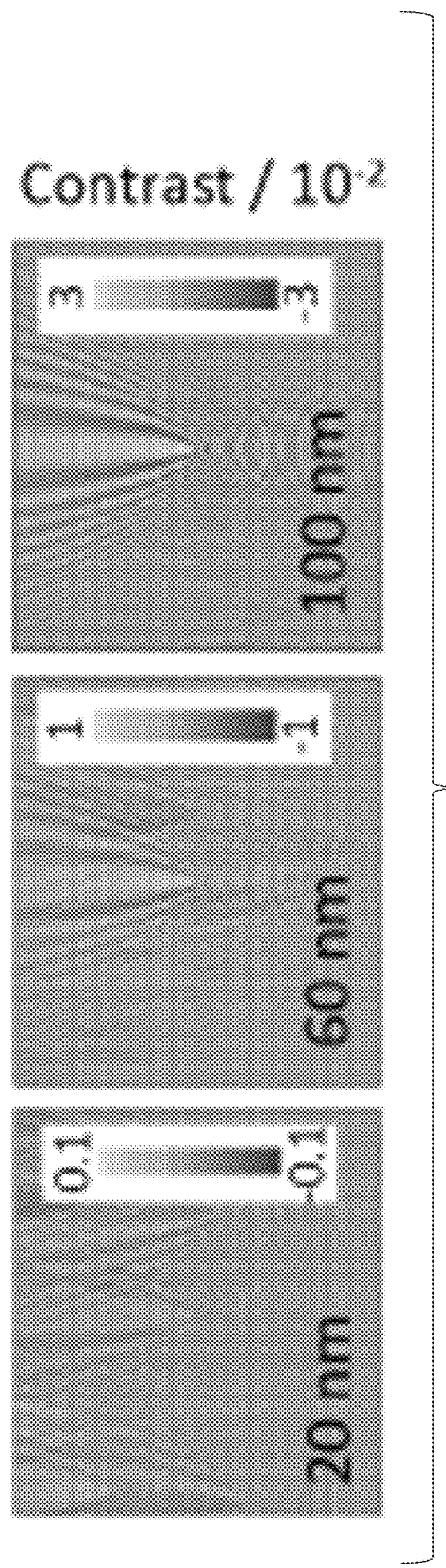
FIG. 9B shows simulated images of polystyrene particles on an ITO surface.

For weak scattering, $|u_s|^2$ is small, and Eq. 13 is reduced to $$I(r,r')=2\,\text{Re}\{[u_r(r)+u_e(r)]u_s(r,r')\}, \quad (14)$$

which shows that the image contrast is originated from the interference between $u_r+u_e$ and $u_s$. This analysis indicates the imaging principle is interferometric, similar to iSCAT[36] and surface plasmon resonance imaging[37]. Using Eq. 14, the inventors computed an image, which closely resembles the experimental image (FIG. 9B). Eq. 14 shows the image intensity scales with α which is proportional to the cubic power of the diameter ($D_H^3$). The observed size dependence of the image contrast is slower than cubic power (between 2-3), which is attributed to surface roughness, as discussed below.

Effect of Surface Roughness

Referring now jointly to FIG. 9A and FIG. 9B, FIG. 9A shows an example of surface roughness effect in a typical AFM image of the ITO surface, showing grains with 0-20 nm in diameter and FIG. 9B shows simulated images of polystyrene particles on an ITO surface. The above analysis assumes a perfect surface. In practice, ITO surface is rough, as shown by atomic force microscopy (AFM). The surface roughness effect is particularly important for small objects, such as protein molecules, which are comparable with or smaller than the surface rough features (grains). The inventors simulate the surface roughness effect by including an additional term, $\mu_{rough}$ in Eq. 13, $$I(r,r')=|u_r(r)+u_e(r)+\mu_{rough}(r,r')+u_s(r,r')|^2-|u_r(r)+u_e(r)+\mu_{rough}(r,r')|^2, \quad (15)$$

which leads to increased background and also slower dependence of the image contrast on the protein size. Using the grain size of the ITO measured from the AFM images, the inventors performed numerical simulation of the size dependence of the image contrast. The simulation used 100 small polystyrene particles randomly distributed on the surface around a polystyrene particle of interest with diameter varying from 20 to 150 nm. The size distribution of the small particles used to simulation was based on the AFM measurement, which varied from 0-20 nm, with an average diameter of 10 nm.

Figure 9C:
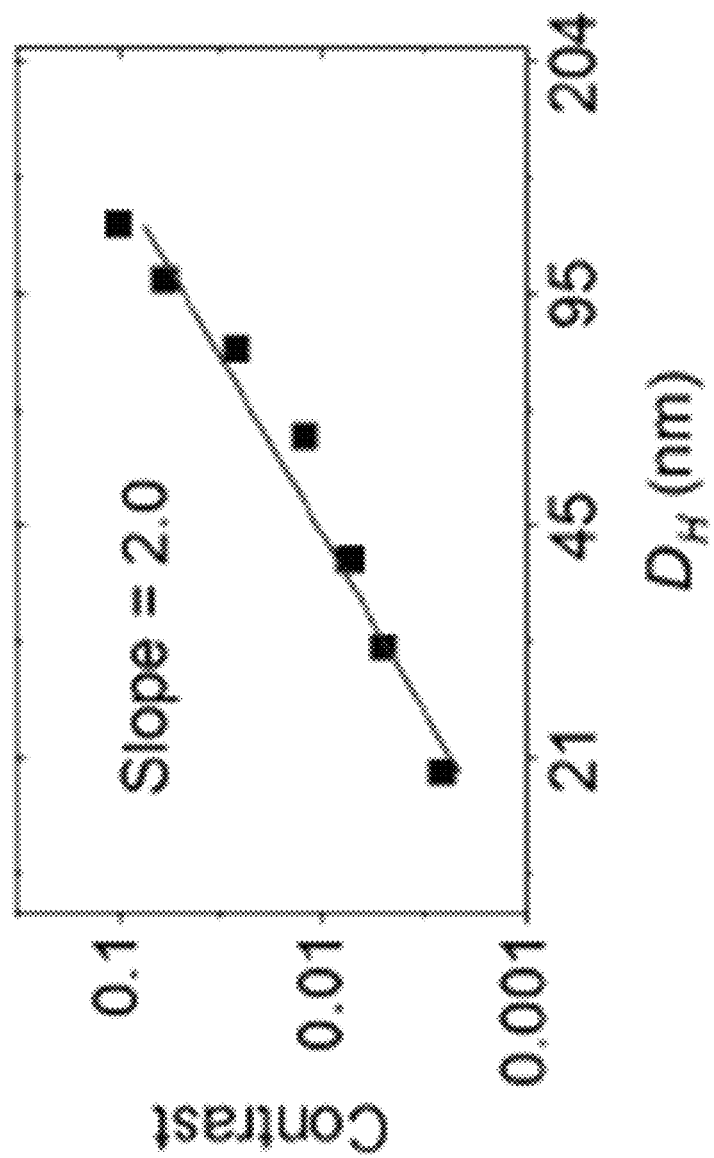
FIG. 9C shows an example of a plot representing image contrast of polystyrene particles vs. diameter.

Referring now to FIG. 9C, an example of a plot representing image contrast of polystyrene particles vs. diameter is shown. The logarithmic plot of the image contrast vs. diameter shows a slope of ~2.0, confirming decreased size dependence of the image contrast on the particle diameter (FIG. 9C). Note that each data point represents the average over 10 simulations.

Surface Charging Effect and Background Noise

Figure 10A:
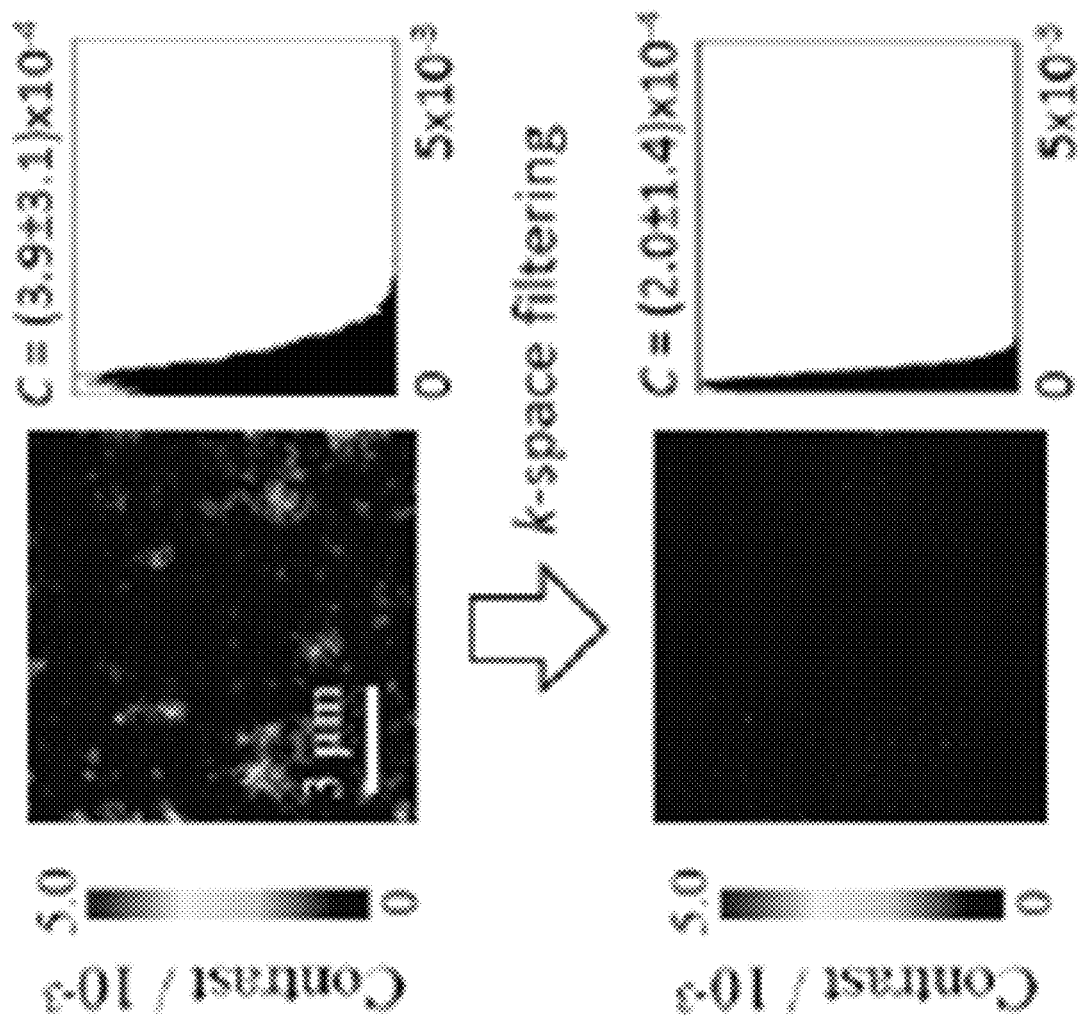
FIG. 10A shows an example of the effect of ITO surface charging on image contrast, and measurements of diameter and charge of proteins including an FFT image of a bare ITO surface modulated by applying a potential with amplitude, $U_0=10$ V and frequency, f=80 Hz.

Referring now to FIG. 10A, an example of the effect of ITO surface charging on image contrast, and measurements of diameter and charge of proteins including an FFT image of a bare ITO surface modulated by applying a potential with amplitude, $U_0$=10 V and frequency, f=80 Hz is shown. A bare ITO surface also responds to the applied oscillating electric field and gives rise to background noise. This response arises from the charge-dependent refractive index of ITO. To evaluate this effect, the inventors modulated a bare ITO slide with potential ($U_0$=10 V and frequency=80 Hz) and obtained the FFT images. The features shown in the images are due to the grains of the ITO surface, which affect limits of detection for the diameter ($D_H$) and charge (q).

Figure 10B:
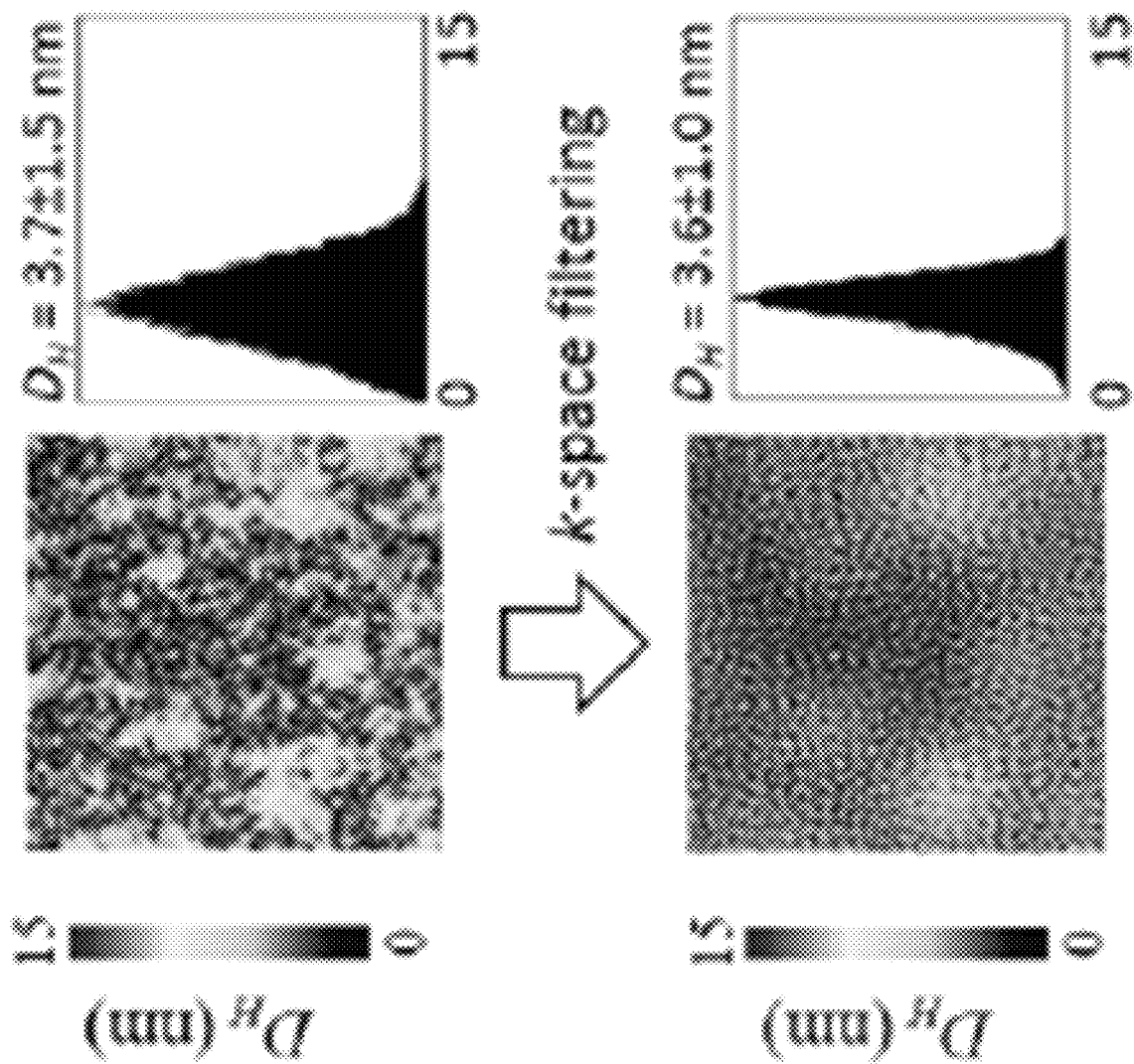
FIG. 10B shows an example of the image contrast of each pixel in FIG. 10A converted into diameter ($D_H$), showing a histogram with $D_H=3.7±1.5$ nm.

Referring now to FIG. 10B, an example of the image contrast of each pixel in FIG. 10A converted into diameter ($D_H$), showing a histogram with $D_H$=3.7±1.5 nm.

Figure 10C:
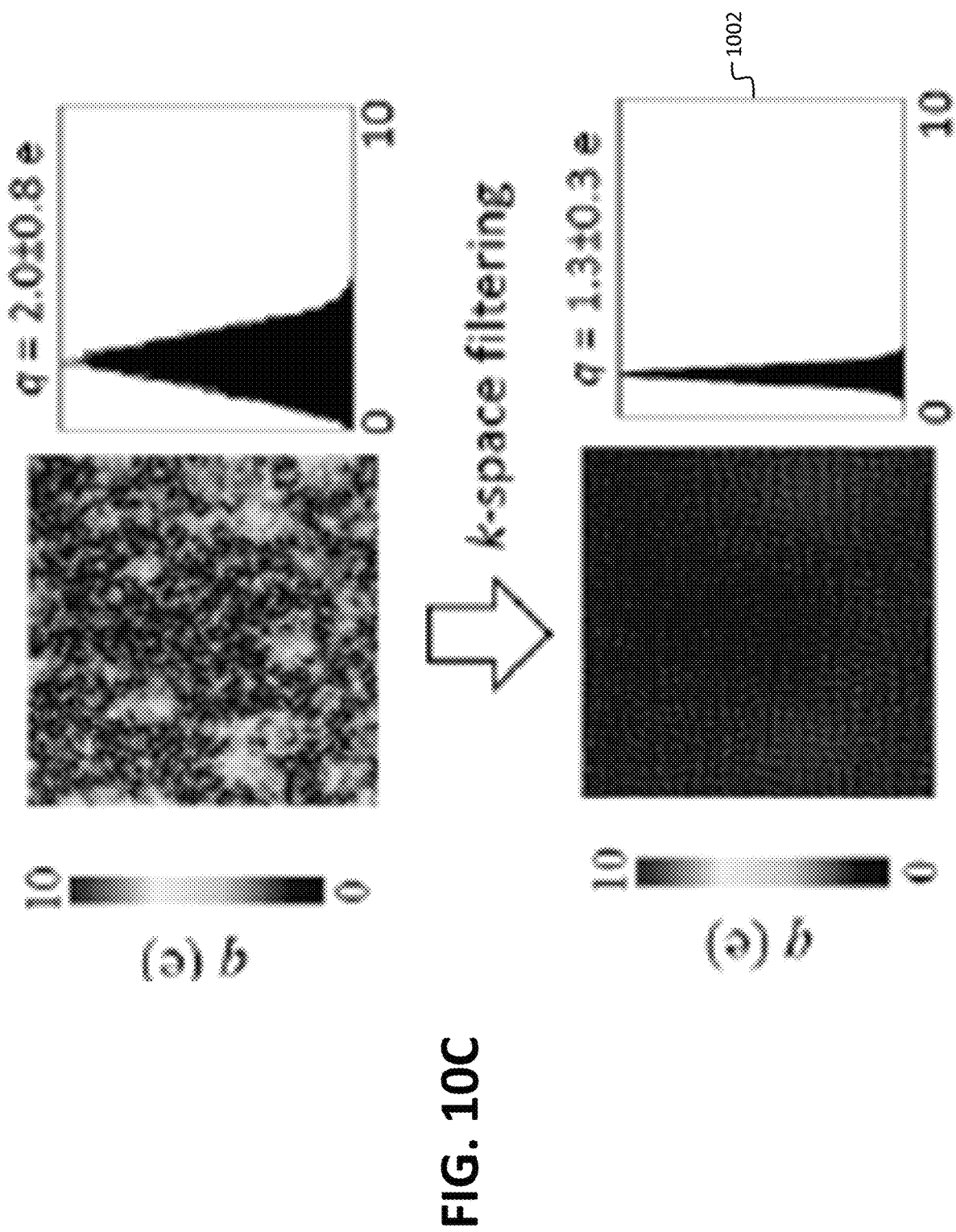
FIG. 10C shows an example of the image contrast of each pixel in FIG. 10A converted into charge (q) for mobility of $1×10^{-8}$ $m^2V^{-1}s^{-1}$.

Referring now to FIG. 10C, an example of the image contrast of each pixel in FIG. 10A converted charge (q) is shown. The image contrast of each pixel in FIG. 10A is converted into charge (q) for mobility of $1\times10^{-8}$ $m^2V^{-1}s^{-1}$. The inventors converted the features in the ITO background image to the equivalent $D_H$ and q noise images using the calibration curve in FIG. 5B and the Einstein equation (assume the mobility is $1\times10^{-8}$ $m^2V^{-1}s^{-1}$, the typical value for proteins). Histogram 1002, for example, shows q=2.0±0.8 e. The results show the distributions of $D_H$ and q associated with surface roughness (as shown in FIG. 10B-FIG. 10C).

Figure 10D:
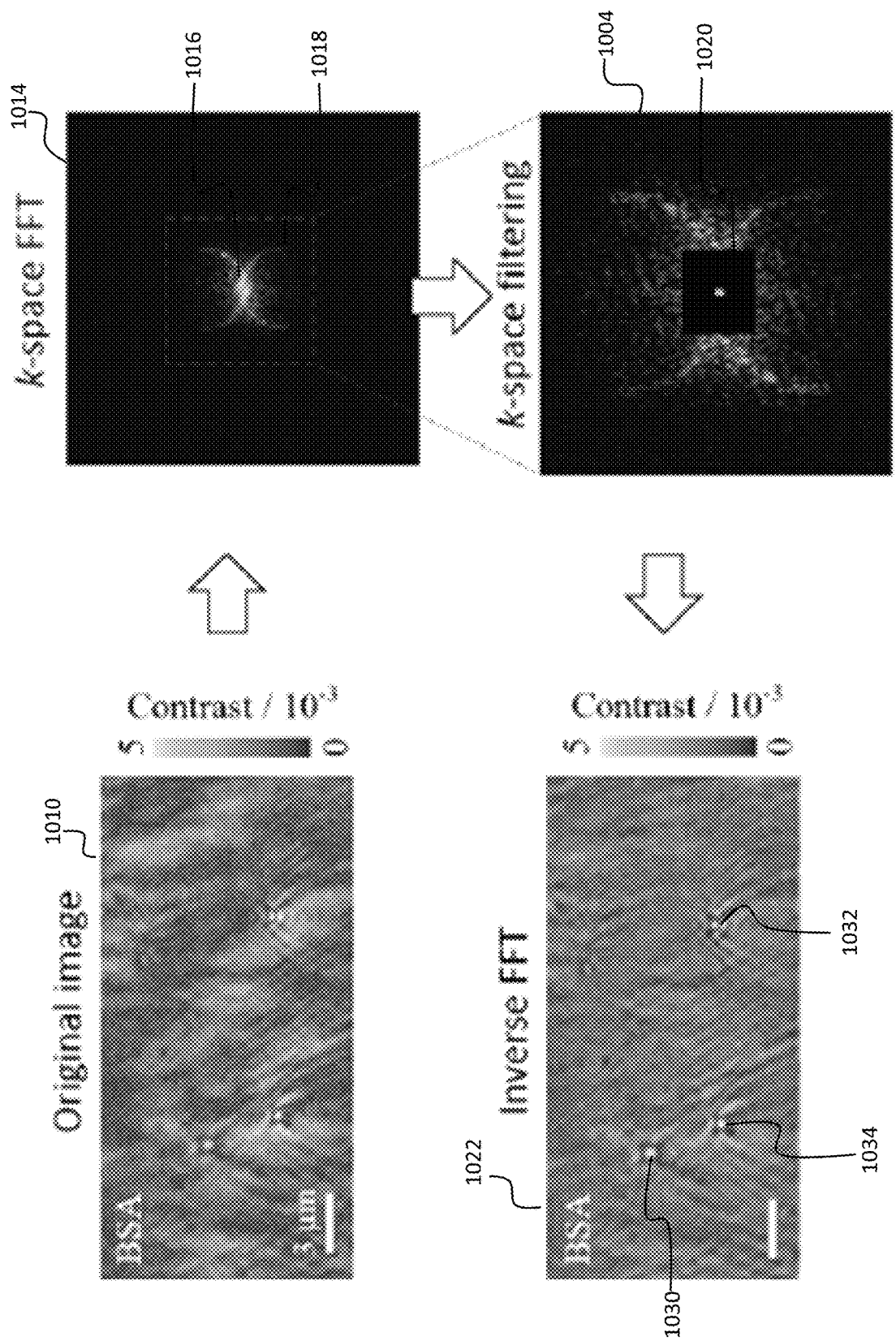
FIG. 10D shows an example of oscillation amplitude image of single BSA molecules and background.

Referring now to FIG. 10D, an example of oscillation amplitude image of single BSA molecules and background is shown. In single molecule detection, the charge-induced features overlap with the protein images and affect detection accuracy. To reduce this effect, the inventors performed 2D FFT to the oscillation amplitude image and convert the image from real space to k-space, which shows two rings originated from the interference of scattered field and evanescent field.[37] The inventors apply a filter to block part of the low frequency region where the background features are located, and the result shows most of the features are removed. The inventors applied the same filter to the images in FIG. 5A-FIG. 5C to remove the background features and obtained the distributions of $D_H$ and q, from which the limits of detection were estimated to be ~1.0 nm for diameter, and 0.3 e for charge (FIG. 5E-FIG. 5F).

The images in FIG. 10A-FIG. 10D are filtered in k-space with a filter 1004 shown in to reduce the background features. The contrast, diameter and charge show histograms with C=(2.0±1.4)×10$^{-4}$, D H=3.6±1.0 nm, and q=1.3±0.3 e, respectively. An original amplitude image of single BSA molecules and background 1010 is obtained. Next a 2D FFT is performed with the oscillation amplitude image 1010 to produce a k-space FFT image 1014 which shows two rings originated from interference 1016,1018. A magnified view 1020 of the dashed region in FFT image 1014 is also shown. The center region 1020 shows the frequencies excluded by the filter. Finally, an inverse 2D FFT image 1022 of image 1020 shows BSA molecules 1030, 1032, 1034 and reduced background noises.

Shot Noise Estimation

In one setup, the photon collection efficiency was limited by the imager (sCMOS camera, Hamamatsu). It has a full well capacity 30000 electrons per pixel. The recorded imaging area is 2048×256 pixels and the frame rate is 800 fps, which leads to a maximum photon flux of 1.2×10$^{13}$ e/s, corresponding to 2×10$^{7}$ photons per pixel per second. A typical scattering pattern of a protein or particle has an area greater than 100×100 pixels, which corresponds to 2×10$^{11}$ photons per second (recording time is 1 second). This gives an upper limit of signal-to-noise ratio of 4×10$^{5}$ per protein or particle. The inventors used 10×10 pixels as regions of interest for contrast analysis, which has an upper limit of signal-to-noise ratio of 4×10$^{4}$.

Charge Screening Effect

Effective charges are measured here, which are related to the net charges by, $$\frac{\sigma_{eff}}{\sigma_{total}} = \frac{\zeta}{\psi} = e^{-\kappa x}, \quad (16)$$

where $\sigma_{eff}/\sigma_{total}$ is the ratio of the effective charge density to the net charge density, $\zeta$ is zeta potential of the protein, $\psi$ is the potential at the protein surface, x is the slipping layer thickness, and $\kappa^{-1}$ is the Debye length, which is determined by the Debye-Hückel equation, $$\kappa^{-1} = \sqrt{\frac{\varepsilon\varepsilon_0 k_B T}{2N_A e^2 I}}, \quad (17)$$

where $\varepsilon$ is the dielectric constant of the buffer, $\varepsilon_0$ is the permittivity of free space, $k_B$ is the Boltzmann constant, NA is the Avogadro number, e is the elementary charge, and I is the ionic strength. Using Eq. 16, the slipping layer thickness of protein molecules can be determined by the zeta potential and Debye length at two different concentrations with, $$x = \frac{\ln\zeta_1/\zeta_2}{\kappa_2 - \kappa_1}. \quad (18)$$

Figure 11:
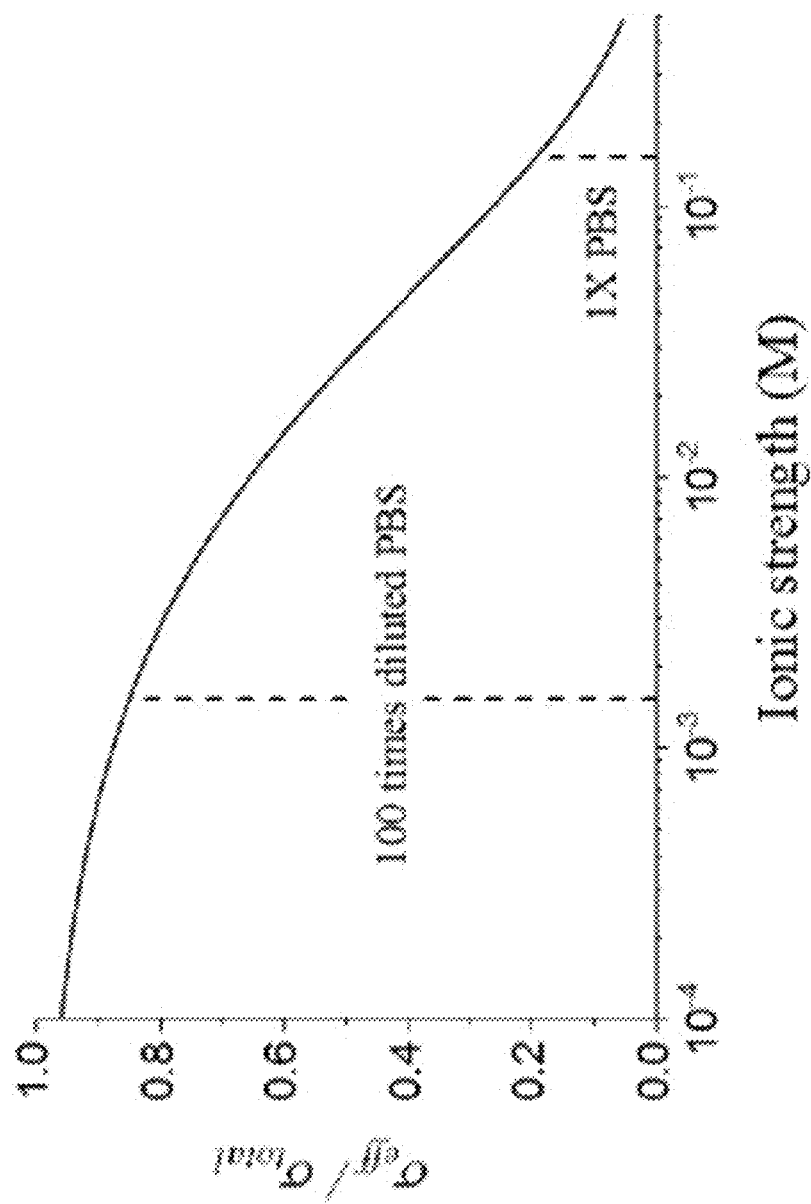
FIG. 11 shows a plot representing an example of charge screening effect.

Referring now to FIG. 11, a plot representing an example of charge screening effect. The inventors measured the zeta potential of lysozyme in 1×PBS and 100 times diluted PBS, which are $\zeta_1$=2.78 mV and $\zeta_2$=13.8 mV, respectively. The corresponding Debye lengths are $\kappa_1^{-1}$=0.789 nm and $\kappa_2^{-1}$=7.89 nm according to Eq. 17, from which the slipping layer thickness for the protein is determined to be 1.4 nm. Using these parameters, the inventors plotted $\sigma_{eff}/\sigma_{total}$ ratio vs. ionic strength, showing that the effective charge is ~20% of total charge for 1×PBS, and ~90% in 100 times diluted PBS.

TABLE 3

Hydrodynamic diameter ($D_H$) of protein reported in literature. *

| Protein | $D_H$ (nm) | Method | Ref. |
|---|---|---|---|
| BSA | 6.6 to 8.6 | DLS | 16 |
|  | 7 | DLS | 17 |
|  | 7.3 | DLS | 18 |
| IgG | 10.58 | Calculation | 19 |
|  | 10.9 | DLS | 20 |
|  | 10.8 to 12.5 | DLS | 21 |
| Lysozyme | 3.7 to 3.9 | DLS | 22 |
|  | 3.7 | DLS | 23 |
|  | 4 | Capillary electrophoresis | 24 |
|  | 4 | NMR | 25 |
| CaM | 4.96 ± 0.18 | NMR | 25 |
|  | 4.4 | Calculation | 26 |
|  | 4.8 | Gel permeation chromatography | 26 |
|  | 5.0 ± 0.2 | DLS | 27 |
|  | 4.44 | SAXS | 28 |
|  | 4.1 | SAXS | 29 |
|  | 4.1 | SAXS | 30 |
| Ca$^{2+}$/CaM | 4.90 ± 0.08 | NMR | 25 |
|  | 6.0 ± 0.2 | DLS | 27 |
|  | 4.3 | SAXS | 29 |

* DLS = dynamic light scattering, SAXS = small-angle X-ray scattering, NMR = nuclear magnetic resonance.

TABLE 4

Mobility ($\mu$) of proteins reported in literature. *

| Protein | $\mu$ (×10$^{-8}$ m$^2$V$^{-1}$s$^{-1}$) | Method | Ref. |
|---|---|---|---|
| BSA | -1.4 | ELS | 16 |
|  | -1.7 | ELS | 31 |
| IgG | -0.8 | Capillary electrophoresis | 20 |
|  | -0.32 | Capillary electrophoresis | 32 |
| Lysozyme | 0.8 | Electrophoresis and simulation | 33 |
|  | 0.15 | ELS | 34 |
|  | 1.8 | Capillary electrophoresis | 24 |
|  | 1.8 | Capillary electrophoresis | 35 |

* Note that mobility is sensitive to pH, ionic strength and ion species, and the mobility measured in literature is not under the same experimental condition as in this work. Thus, small variation could be expected.

TABLE 5

Charge estimation of proteins at pH = 7.4*

| Protein | Charge at pH = 7.4 | |
|---|---|---|
| | Net charge of amino acids | Estimation with zeta potential and size |
| BSA | −14.0 | −8.1 |
| IgG | −0.6 | −5.1 |
| Lysozyme | 8.2 | 2.4 |
| CaM | −24.1 | −6.6 |
| CaM with 4 $Ca^{2+}$ | −16.1 | −4.1 |

*Note that the charge obtained with amino acids could be different from those measured by Zetasizer due to the binding of ions in solution.[36]
**The charge is estimated with Eq. 6 by knowing the zeta potential and size of each protein.

REFERENCES

The contents of the following references are incorporated herein by this reference.

1. Brouhard, G. J. & Rice, L. M. Microtubule dynamics: an interplay of biochemistry and mechanics. *Nature Reviews Molecular Cell Biology* 19, 451-463 (2018).
2. Cournia, Z. et al. Membrane Protein Structure, Function, and Dynamics: a Perspective from Experiments and Theory. *The Journal of membrane biology* 248, 611-640 (2015).
3. Cairns, R. A., Harris, I. S. & Mak, T. W. Regulation of cancer cell metabolism. *Nature Reviews Cancer* 11, 85 (2011).
4. Santos, R. et al. A comprehensive map of molecular drug targets. *Nature Reviews Drug Discovery* 16, 19 (2016).
5. Polanski, M. & Anderson, N. L. A list of candidate cancer biomarkers for targeted proteomics. *Biomarker insights* 1, 1-48 (2007).
6. Borrebaeck, C. A. K. Precision diagnostics: moving towards protein biomarker signatures of clinical utility in cancer. *Nature Reviews Cancer* 17, 199 (2017).
7. Hathout, Y. et al. Large-scale serum protein biomarker discovery in Duchenne muscular dystrophy. *Proceedings of the National Academy of Sciences* 112, 7153-7158 (2015).
8. Olsson, B. et al. CSF and blood biomarkers for the diagnosis of Alzheimer's disease: a systematic review and meta-analysis. *The Lancet Neurology* 15, 673-684 (2016).
9. Schubert, O. T., Röst, H. L., Collins, B. C., Rosenberger, G. & Aebersold, R. Quantitative proteomics: challenges and opportunities in basic and applied research. *Nature Protocols* 12, 1289 (2017).
10. Hughes, A. J. et al. Single-cell western blotting. *Nature Methods* 11, 749 (2014).
11. Chang, L. et al. Identification of protein biomarkers and signaling pathways associated with prostate cancer radioresistance using label-free LC-MS/MS proteomic approach. *Scientific Reports* 7, 41834 (2017).
12. Wilhelm, M. et al. Mass-spectrometry-based draft of the human proteome. *Nature* 509, 582 (2014).
13. Shi, T. et al. Antibody-free, targeted mass-spectrometric approach for quantification of proteins at low picogram per milliliter levels in human plasma/serum. *Proceedings of the National Academy of Sciences*, 201204366 (2012).
14. Gaiduk, A., Yorulmaz, M., Ruijgrok, P. V. & Orrit, M. Room-Temperature Detection of a Single Molecule's Absorption by Photothermal Contrast. *Science* 330, 353-356 (2010).
15. Zijlstra, P., Paulo, P. M. & Orrit, M. Optical detection of single non-absorbing molecules using the surface plasmon resonance of a gold nanorod. *Nature nanotechnology* 7, 379 (2012).
16. Young, G. et al. Quantitative mass imaging of single biological macromolecules. *Science* 360, 423-427 (2018).
17. Ruggeri, F. et al. Single-molecule electrometry. *Nature Nanotechnology* 12, 488 (2017).
18. Shan, X. et al. Detection of Charges and Molecules with Self-Assembled Nano-Oscillators. *Nano Letters* 14, 4151-4157 (2014).
19. Cao, Y., Balamurali, M. M., Sharma, D. & Li, H. A functional single-molecule binding assay via force spectroscopy. *Proceedings of the National Academy of Sciences* 104, 15677-15681 (2007).
20. Yu, H., Shan, X., Wang, S. & Tao, N. Achieving High Spatial Resolution Surface Plasmon Resonance Microscopy with Image Reconstruction. *Analytical Chemistry* 89, 2704-2707 (2017).
21. Hoeflich, K. P. & Ikura, M. Calmodulin in Action: Diversity in Target Recognition and Activation Mechanisms. *Cell* 108, 739-742 (2002).
22. Hall, W. P. et al. A Conformation- and Ion-Sensitive Plasmonic Biosensor. *Nano Letters* 11, 1098-1105 (2011).
23. Saleh, O. A. Perspective: Single polymer mechanics across the force regimes. *The Journal of chemical physics* 142, 194902 (2015).
24. Samorà, P. *Scanning probe microscopies beyond imaging: manipulation of molecules and nanostructures.* (John Wiley & Sons, 2006).
25. Hu, Y. et al. Study of fibrinogen adsorption on poly (ethylene glycol)-modified surfaces using a quartz crystal microbalance with dissipation and a dual polarization interferometry. *Rsc Advances* 4, 7716-7724 (2014).
26. Shan, X. et al. Detection of charges and molecules with self-assembled nano-oscillators. *Nano letters* 14, 4151-4157 (2014).
27. Makino, K. & Ohshima, H. Electrophoretic mobility of a colloidal particle with constant surface charge density. *Langmuir* 26, 18016-18019 (2010).
28. Loeb, A. L., Overbeek, J. T. G., Wiersema, P. & King, C. The electrical double layer around a spherical colloid particle. *Journal of The Electrochemical Society* 108, 269C-269C (1961).
29. Hu, Y. et al. Study of fibrinogen adsorption on poly (ethylene glycol)-modified surfaces using a quartz crystal microbalance with dissipation and a dual polarization interferometry. *RSC Advances* 4, 7716-7724 (2014).
30. Harder, P., Grunze, M., Dahint, R., Whitesides, G. M. & Laibinis, P. E. Molecular Conformation in Oligo(ethylene glycol)-Terminated Self-Assembled Monolayers on Gold and Silver Surfaces Determines Their Ability To Resist Protein Adsorption. *The Journal of Physical Chemistry B* 102, 426-436 (1998).
31. Berger, C. E., Kooyman, R. P. & Greve, J. Surface plasmon propagation near an index step. *Opt. Commun.* 167, 183-189 (1999).
32. Cao, S.-H., Cai, W.-P., Liu, Q. & Li, Y.-Q. Surface Plasmon-Coupled Emission: What Can Directional Fluorescence Bring to the Analytical Sciences? *Annu. Rev. Anal. Chem.* 5, 317-336 (2012).
33. Lakowicz, J. R. Radiative decay engineering 3. Surface plasmon-coupled directional emission. *Anal. Biochem.* 324, 153-169 (2004).
34. Leskova, T. A., Maradudin, A. A. & Zierau, W. Surface plasmon polariton propagation near an index step. *Opt. Commun.* 249, 23-35 (2005).

35. Raether, H. Surface-Plasmons on Smooth and Rough Surfaces and on Gratings. Springer Tracts Mod. Phys. 111, 1-133 (1988).
36. Cole, D., Young, G., Weigel, A., Sebesta, A. & Kukura, P. Label-Free Single-Molecule Imaging with Numerical-Aperture-Shaped Interferometric Scattering Microscopy. ACS Photonics 4, 211-216 (2017).
37. Yu, H., Shan, X., Wang, S. & Tao, N. Achieving High Spatial Resolution Surface Plasmon Resonance Microscopy with Image Reconstruction. Analytical Chemistry 89, 2704-2707 (2017).
38. Jachimska, B., Wasilewska, M. & Adamczyk, Z. Characterization of Globular Protein Solutions by Dynamic Light Scattering, Electrophoretic Mobility, and Viscosity Measurements. Langmuir 24, 6866-6872 (2008).
39. Yu, S. et al. Albumin-coated SPIONs: An experimental and theoretical evaluation of protein conformation, binding affinity and competition with serum proteins. Nanoscale 8, 14393-14405 (2016).
40. Li, Y., Yang, G. & Mei, Z. Spectroscopic and dynamic light scattering studies of the interaction between pterodontic acid and bovine serum albumin. Acta Pharmaceutica Sinica B 2, 53-59 (2012). 17
41. Armstrong, J. K., Wenby, R. B., Meiselman, H. J. & Fisher, T. C. The hydrodynamic radii of macromolecules and their effect on red blood cell aggregation. Biophysical journal 87, 4259-4270 (2004).
42. Bermudez, O. & Forciniti, D. Aggregation and denaturation of antibodies: a capillary electrophoresis, dynamic light scattering, and aqueous two-phase partitioning study. Journal of Chromatography B 807, 17-24 (2004).
43. Sukumar, M., Doyle, B. L., Combs, J. L. & Pekar, A. H. Opalescent appearance of an IgG1 antibody at high concentrations and its relationship to noncovalent association. Pharmaceutical research 21, 1087-1093 (2004).
44. Parmar, A. S. & Muschol, M. Hydration and hydrodynamic interactions of lysozyme: effects of chaotropic versus kosmotropic ions. Biophysical journal 97, 590-598 (2009).
45. Grigsby, J., Blanch, H. & Prausnitz, J. Diffusivities of lysozyme in aqueous MgCl2 solutions from dynamic light-scattering data: effect of protein and salt concentrations. The Journal of Physical Chemistry B 104, 3645-3650 (2000).
46. Sharma, U. & Carbeck, J. D. Hydrodynamic radius ladders of proteins. Electrophoresis 26, 2086-2091 (2005).
47. Weljie, A. M., Yamniuk, A. P., Yoshino, H., Izumi, Y. & Vogel, H. J. Protein conformational changes studied by diffusion NMR spectroscopy: Application to helix-loop-helix calcium binding proteins. Protein Science 12, 228-236 (2003).
48. Sorensen, B. R. & Shea, M. A. Calcium binding decreases the stokes radius of calmodulin and mutants R74A, R90A, and R90G. Biophysical Journal 71, 3407-3420 (1996).
49. Papish, A. L., Tari, L. W. & Vogel, H. J. Dynamic Light Scattering Study of Calmodulin-Target Peptide Complexes. Biophysical Journal 83, 1455-1464 (2002).
50. Majava, V. et al. Interaction between the C-terminal region of human myelin basic protein and calmodulin: analysis of complex formation and solution structure. BMC Structural Biology 8, 10 (2008).
51. Seaton, B., Head, J., Engelman, D. & Richards, F. Calcium-induced increase in the radius of gyration and maximum dimension of calmodulin measured by small-angle X-ray scattering. Biochemistry 24, 6740-6743 (1985).
52. Majava, V. & Kursula, P. Domain Swapping and Different Oligomeric States for the Complex Between Calmodulin and the Calmodulin-Binding Domain of Calcineurin A. PLOS ONE 4, e5402 (2009).
53. Takeda, K. et al. Size and mobility of sodium dodecyl sulfate-bovine serum albumin complex as studied by dynamic light scattering and electrophoretic light scattering. Journal of Colloid and Interface Science 154, 385-392 (1992).
54. Martin, N. et al. Prevention of thermally induced aggregation of IgG antibodies by noncovalent interaction with poly (acrylate) derivatives. Biomacromolecules 15, 2952-2962 (2014).
55. Yamaguchi, A. & Kobayashi, M. Quantitative evaluation of shift of slipping plane and counterion binding to lysozyme by electrophoresis method. Colloid and Polymer Science 294, 1019-1026 (2016).
56. Cugia, F., Monduzzi, M., Ninham, B. W. & Salis, A. Interplay of ion specificity, pH and buffers: insights from electrophoretic mobility and pH measurements of lysozyme solutions. RSC Advances 3, 5882-5888 (2013).
57. Szymariski, J.d. et al. Net charge and electrophoretic mobility of lysozyme charge ladders in solutions of nonionic surfactant. The Journal of Physical Chemistry B 111, 5503-5510 (2007).
58. Yang, D., Kroe-Barrett, R., Singh, S. & Laue, T. IgG Charge. Preprints (2018). 18
59. G. Z. Ma, G-D Syu, X. N. Shan, B. Henson, S. P. Wang, P. Desai, H. Zhu and N. J. Tao, "Measuring ligand binding kinetics to membrane proteins using virion nano-oscillators J. Am. Chem. Soc., 140, 11495-11501(2018).
60. Y Fang, S Chen, W Wang, X Shan, N. J. Tao, "Real time monitoring of phosphorylation kinetics with self-assembled nanooscillators", Angew. Chem. Int. Ed., 54(8), 2538-2542(2015).
61. Xiaonan, Shan, Ymin Fang, Shaopeng Wang, Shaopeng, Yan Guan, Hongyuan Chen, and N. J. Tao, "Detection of charges and molecules with self-assembled nano-oscillators", Nano Lett. 14, 4151-4157(2014).

What is claimed is:
1. A method for optical imaging of single molecules comprising:
tethering a plurality of single molecules via a flexible polymer linker to a conductive surface;
driving the plurality of single molecules into oscillation by applying an alternating electric field to the conductive surface;
directing incident light onto the conductive surface through an objective lens from an angle to generate an evanescent field near the conductive surface, where the evanescent field interacts with the plurality of single molecules driven to oscillation and produces scattered light;
collecting the scattered light;
operating an imager to record a sequence of images of the scattered light;
applying an algorithm to the recorded sequence of images to remove noise at frequencies other than the frequency of the alternating electric field to produce an oscillation amplitude image; and
determining size, charge, and mobility of the plurality of single molecules from the oscillation amplitude image.

2. The method of claim 1 wherein the conductive surface comprises a glass slide having a surface coated with indium tin oxide (ITO).

3. The method of claim 1 wherein the algorithm comprises a Fast Fourier Transform (FFT) filter.

4. The method of claim 3 wherein the Fast Fourier transform (FFT) filter is applied to the time sequence of images to produce an oscillation amplitude image, which resolves single protein molecules of the plurality of single molecules.

5. The method of claim 1 wherein the plurality of single molecules are selected from the group consisting of DNA molecules, RNA molecules and protein molecules.

6. The method of claim 1 wherein applying the alternating electric field comprises using a three-electrode electrochemical configuration to drive the plurality of single molecules into oscillation.

7. The method of claim 1 wherein the flexible polymer linker comprises polyethylene glycol (PEG), which couples proteins of the plurality of single molecules to the conductive surface.

8. The method of claim 7 wherein a value of oscillation is determined by entropic force of the PEG linker and driving force of the alternating electric field, and its oscillation amplitude ($\Delta z_0$) is given by $$\Delta z_0 = \frac{E_0(\Delta z_0, U_0)}{k_{PEG}} q. \qquad (1)$$

where $E_0(\Delta z_0, U_0)$ is the amplitude of the alternating electric field, which is a function of protein-conductive surface distance $\Delta z_0$ and surface potential $U_0$, and $k_{PEG}$ is the entropic spring constant of the PEG linker.

9. The method of claim 1 wherein the sequence of images are recorded at 800 frames/s.

10. The method of claim 1 wherein the evanescent field decays exponentially from the conductive surface into a solution with a decay constant of d and the oscillation amplitude image contrast, where the oscillation amplitude image contrast, $\Delta C\ (\Delta z_0, D_H)$, is given by the formula $$\frac{\Delta C(\Delta z_0, D_H)}{C(0, D_H)} = 1 - \exp\left(-\frac{\Delta z_0}{d}\right), \qquad (2)$$

where $D_H$ is the protein hydrodynamic diameter, $C(0, D_H)$ is a molecule oscillation amplitude image contrast at zero oscillation amplitude ($\Delta z_0=0$), and where $\Delta z$ represents the oscillation amplitude.

11. The method of claim 10 wherein the oscillation amplitude is measured at an electric field strength such that the oscillation amplitude reaches a maximum oscillation amplitude determined by the length of the flexible polymer linker, and the size of the molecule is determined as proportional to the maximum oscillation amplitude.

12. A method for optical imaging of single protein molecules comprising:
tethering a plurality of single protein molecules via a flexible polymer linker to a conductive surface;
driving the plurality of single protein molecules into oscillation by applying an alternating electric field to the conductive surface;
directing incident light onto the conductive surface from an angle to generate an evanescent field so as to produce scattered light from the plurality of single protein molecules and the conductive surface;
collecting and imaging the scattered light;
recording a sequence of images of the scattered light including a plurality of pixels; and
applying an imaging processing algorithm to the recorded sequence of images to produce an oscillation amplitude image yielding size, charge, and mobility of the plurality of single protein molecules.

13. The method of claim 12 wherein applying the alternating electric field comprises using a three-electrode electrochemical configuration to drive the plurality of single protein molecules into oscillation.

14. The method of claim 12 wherein the flexible polymer linker comprises polyethylene glycol (PEG).

15. The method of claim 14 wherein a value of oscillation is determined by entropic force of the PEG linker and driving force of the alternating electric field, and its oscillation amplitude ($\Delta z_0$) is given by $$\Delta z_0 = \frac{E_0(\Delta z_0, U_0)}{k_{PEG}} q. \qquad (1)$$

where $E_0(\Delta z_0, U_0)$ is the amplitude of the alternating electric field, which is a function of protein-conductive surface distance $\Delta z_0$ and surface potential $U_0$, and $k_{PEG}$ is the entropic spring constant of the PEG linker.

16. The method of claim 12 wherein oscillation is imaged at 800 frames/s, where the potential and frequency of the alternating electric field are 8 V and 80 Hz, respectively.

17. The method of claim 12 wherein the Fast Fourier transform (FFT) filter is applied to the sequence of images to produce an oscillation amplitude image which resolves single protein molecules.

18. The method of claim 12 wherein the evanescent field decays exponentially from the conductive surface into a solution with a decay constant of d and the oscillation amplitude image contrast, where the image contrast, $\Delta C\ (\Delta z_0, D_H)$, is given by the formula $$\frac{\Delta C(\Delta z_0, D_H)}{C(0, D_H)} = 1 - \exp\left(-\frac{\Delta z_0}{d}\right), \qquad (2)$$

where $D_H$ is the protein hydrodynamic diameter, $C(0, D_H)$ is a molecule oscillation amplitude image contrast at zero oscillation amplitude ($\Delta z_0=0$), where $\Delta z$ represents the oscillation amplitude and $\Delta C$ represents oscillation amplitude image contrast.

19. The method of claim 12 wherein the oscillation amplitude is measured at an electric field strength such that the oscillation amplitude reaches a maximum determined by the length of the flexible polymer linker, and the size of the molecule is determined as proportional to from this maximum oscillation amplitude.

20. A method for optical imaging of single protein molecules comprising:
tethering a plurality of single protein molecules via a flexible polyethylene glycol (PEG) to a conductive surface;
driving the plurality of single protein molecules into oscillation by applying an alternating electric field to the conductive surface;
directing incident light onto the conductive surface from an angle to generate an evanescent field so as to produce scattered light from the plurality of single protein molecules and the conductive surface;

collecting and imaging the scattered light;

recording a sequence of images of the scattered light;

applying a Fast Fourier transform (FFT) filter to the recorded sequence of images to produce an oscillation amplitude image, which resolves single protein molecules to each pixel of the recorded image sequence to produce an oscillation amplitude image yielding size, charge, and mobility of the plurality of single protein molecules.

21. The method of claim 1 wherein the conductive surface scatters light that interferes with light scattered by the plurality of single protein molecules.

* * * * *